(12) United States Patent
Uda et al.

(10) Patent No.: US 9,492,333 B2
(45) Date of Patent: Nov. 15, 2016

(54) ABSORBENT ARTICLE

(71) Applicant: UNICHARM CORPORATION, Shikokuchuo-shi, Ehime (JP)

(72) Inventors: Masashi Uda, Kanonji (JP); Takashi Maruyama, Kononji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/430,447

(22) PCT Filed: Aug. 19, 2013

(86) PCT No.: PCT/JP2013/072123
§ 371 (c)(1),
(2) Date: Mar. 23, 2015

(87) PCT Pub. No.: WO2014/050360
PCT Pub. Date: Apr. 3, 2014

(65) Prior Publication Data
US 2015/0238370 A1    Aug. 27, 2015

(30) Foreign Application Priority Data

Sep. 28, 2012  (JP) ................................ 2012-218897
Mar. 31, 2013  (JP) ................................ 2013-075540

(51) Int. Cl.
*A61F 13/15*    (2006.01)
*A61F 13/534*   (2006.01)
(Continued)

(52) U.S. Cl.
CPC ....... *A61F 13/534* (2013.01); *A61F 13/15804* (2013.01); *A61F 13/4756* (2013.01);
(Continued)

(58) Field of Classification Search
CPC ............. A61F 13/51113; A61F 13/52; A61F 13/511; A61F 13/513; A61F 2013/51059; A61F 2013/51061; A61F 2013/51066
USPC ......................... 604/367, 364, 378, 381, 382
See application file for complete search history.

(56) References Cited

U.S. PATENT DOCUMENTS 6,001,911 A * 12/1999 Ishizaki ................ A61F 13/531
                                                    521/141
6,617,490 B1   9/2003 Chen et al.
(Continued)

FOREIGN PATENT DOCUMENTS

EP    1568340 A1    8/2005
EP    2837371 A1    2/2015
(Continued)

OTHER PUBLICATIONS

Atsushi Fujita; "Prediction of Organic Compounds and Organic Conceptual Diagram"; Oct. 1957; pp. 719-725; vol. 11, No. 10; Kagaku no Ryoiki (Region of Chemistry).
(Continued)

*Primary Examiner* — Jacqueline Stephens
(74) *Attorney, Agent, or Firm* — Hauptman Ham, LLP

(57) ABSTRACT

The present invention addresses the problem of, in an absorbent article, maintaining at a certain level or lower the difference between the dry flexural rigidity and wet flexural rigidity [(dry flexural rigidity)–(wet flexural rigidity)] at a bonding part. To solve this problem, provided is a sanitary napkin which comprises a top sheet, a back sheet, an absorbent body that is interposed between the top sheet and the back sheet and a compressed part that unites the top sheet and the absorbent body in the thickness direction, wherein: the absorbent body contains a cellulose-based water absorbing fiber and a thermoplastic resin fiber, said thermoplastic resin fiber containing as a monomer component an unsaturated carboxylic acid, an unsaturated carboxylic acid anhydride or a mixture thereof; and the difference between the dry Gurley stiffness and wet Gurley stiffness of the compressed part is maintained at 2.5 mN/12.5 mm or lower.

21 Claims, 7 Drawing Sheets

(51) Int. Cl.
  *A61F 13/475*  (2006.01)
  *A61F 13/539*  (2006.01)
  *A61F 13/511*  (2006.01)
  *A61F 13/51*  (2006.01)
  *A61F 13/513*  (2006.01)
  *A61F 13/53*  (2006.01)

(52) U.S. Cl.
  CPC ............ *A61F13/539* (2013.01); *A61F 13/511* (2013.01); *A61F 13/513* (2013.01); *A61F 13/51113* (2013.01); *A61F 13/52* (2013.01); *A61F 2013/51059* (2013.01); *A61F 2013/51061* (2013.01); *A61F 2013/51066* (2013.01); *A61F 2013/530233* (2013.01)

(56) References Cited

U.S. PATENT DOCUMENTS

| | | | |
|---|---|---|---|
| 2001/0056269 | A1 | 12/2001 | Shimada et al. |
| 2003/0187417 | A1* | 10/2003 | Kudo ................ A61F 13/15699 604/379 |
| 2004/0199134 | A1 | 10/2004 | Mizutani et al. |
| 2008/0010795 | A1 | 1/2008 | Mizutani et al. |
| 2008/0137368 | A1 | 6/2008 | Matsumoto |

FOREIGN PATENT DOCUMENTS

| | | | |
|---|---|---|---|
| JP | 2004-261231 | A | 9/2004 |
| JP | 2004-270041 | A | 9/2004 |
| JP | 2007-130274 | A | 5/2007 |
| JP | 3916852 | B2 | 5/2007 |
| JP | 2008-002034 | A | 1/2008 |
| JP | 2008-130274 | A | 6/2008 |
| JP | 4221849 | B2 | 2/2009 |
| JP | 2011-19896 | A | 2/2011 |

OTHER PUBLICATIONS

International Search Report mailed Sep. 17, 2013 in International Application No. PCT/JP2013/072123 filed Aug. 19, 2013.

* cited by examiner

FIG. 4
(a)
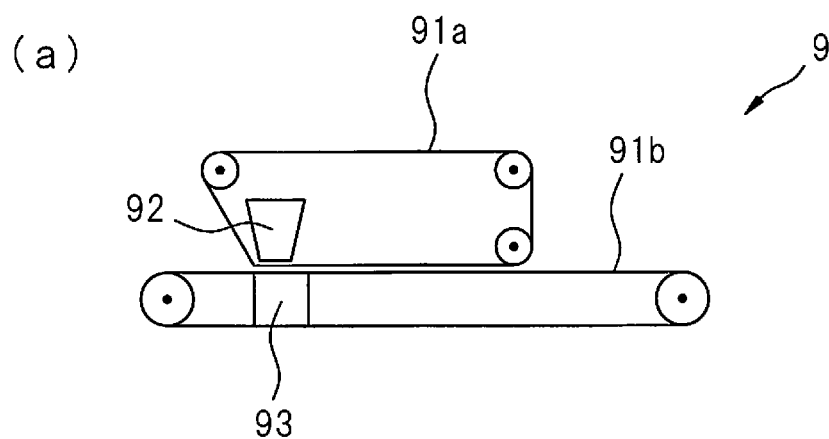
(b)
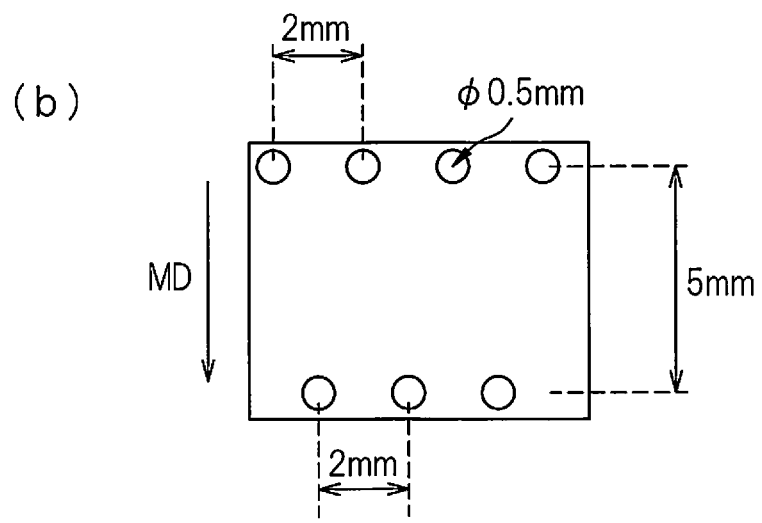

FIG. 6
(a)
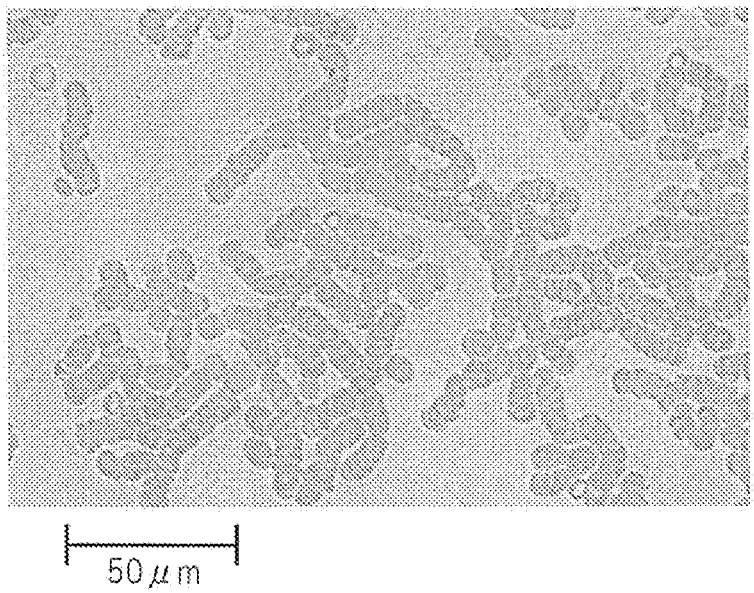
50μm
(b)
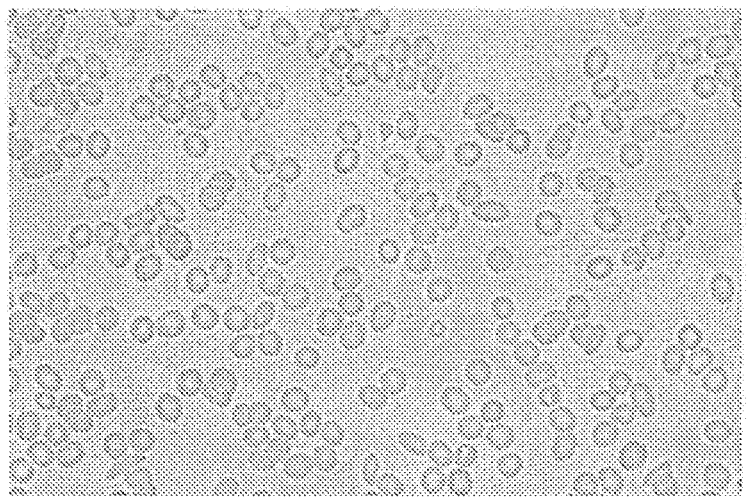
50μm

ABSORBENT ARTICLE

RELATED APPLICATIONS

The present application is a National Phase of International Application Number PCT/JP2013/072123, filed Aug. 19, 2013, which claims priority to Japanese Application Number 2012-218897, filed Sep. 28, 2012 and Japanese Application Number 2013-075540, filed Mar. 31, 2013.

TECHNICAL FIELD

The present invention relates to an absorbent article.

BACKGROUND ART

An absorbent body for an absorbent article is known which has an absorbent retaining layer comprising fluff pulp, a super-absorbent polymer and heat sealable synthetic resin fibers, and a nonwoven fabric layer composed of heat sealable synthetic resin fibers which is situated on the top sheet side of the absorbent retaining layer (PTL 1). In the absorbent body described in PTL 1, the heat sealable synthetic resin fibers in the absorbent retaining layer are tangled or heat-fused together, and the heat sealable synthetic resin fibers in the absorbent retaining layer and the heat sealable synthetic resin fibers in the nonwoven fabric layer are heat-fused, in order to prevent deformation of the absorbent body during use of the absorbent article.

There are also known, as thermal bonding composite fibers for airlaid nonwoven fabrics, core-sheath composite fibers that have as the sheath component a modified polyolefin graft-polymerized with a vinyl monomer comprising an unsaturated carboxylic acid or unsaturated carboxylic anhydride, and as the core component a resin with a higher melting point than the modified polyolefin (PTLs 2 and 3).

CITATION LIST

Patent Literature

PTL 1 Japanese Patent Publication No. 3916852
PTL 2 Japanese Patent Publication No. 4221849
PTL 3 Japanese Unexamined Patent Publication No. 2004-270041

SUMMARY OF INVENTION

Technical Problem

The absorbent body described in PTL 1 is situated between a top sheet and a back sheet, and when a joining section has been formed joining the top sheet and absorbent body (for example, compressed sections that integrate the top sheet and absorbent body in the thickness direction), the flexural rigidity of the joining section when dry (before fluid absorption) (i.e. the dry flexural rigidity) is sufficient. However, since the flexural rigidity of the joining section when in a moist state (after fluid absorption) (i.e. the wet flexural rigidity) is significantly reduced with reduction in the strength of the absorbent body, the difference between the dry flexural rigidity and wet flexural rigidity of the joining section (dry flexural rigidity−wet flexural rigidity) increases. This can lower the adhesiveness of the top sheet on the wearer and produce deformation in the absorbent body, potentially resulting in leakage of fluids and an uncomfortable feeling for the wearer.

The core-sheath composite fibers described in PTLs 2 and 3 are known to have satisfactory adhesion with cellulose-based fibers, but their suitability for use as constituent components for absorbent bodies has not been known.

It is therefore an object of the present invention to provide an absorbent article comprising an absorbent body that contains cellulose-based water-absorbent fibers, and thermoplastic resin fibers including an unsaturated carboxylic acid, unsaturated carboxylic anhydride or its mixture as the monomer component, wherein the difference between the dry flexural rigidity and the wet flexural rigidity of the joining section (dry flexural rigidity−wet flexural rigidity) can be kept to a set value or less.

Solution to Problem

In order to solve the problems described above, the invention provides an absorbent article comprising a liquid-permeable layer, a liquid-impermeable layer, an absorbent body provided between the liquid-permeable layer and the liquid-impermeable layer, and a joining section that joins the liquid-permeable layer and the absorbent body, wherein the absorbent body contains, as constituent fibers, cellulose-based water-absorbent fibers, and thermoplastic resin fibers that include an unsaturated carboxylic acid, an unsaturated carboxylic anhydride or a mixture thereof as the monomer component, the difference between the dry Gurley bending resistance and the wet Gurley bending resistance of the joining section being 2.5 mN/12.5 mm or less.

Advantageous Effects of Invention

According to the invention there is provided an absorbent article comprising an absorbent body that contains cellulose-based water-absorbent fibers, and thermoplastic resin fibers including an unsaturated carboxylic acid, unsaturated carboxylic anhydride or its mixture as the monomer component, wherein the difference between the dry flexural rigidity and the wet flexural rigidity of the joining section can be kept to a set value or less.

BRIEF DESCRIPTION OF DRAWING

FIGS. 4(a) and (b) are diagrams showing an SJ belt press machine as used in the examples.
FIG. 6 is a pair of photomicrographs of menstrual blood containing and not containing a blood slipping agent.

DESCRIPTION OF EMBODIMENTS

Figure 1:
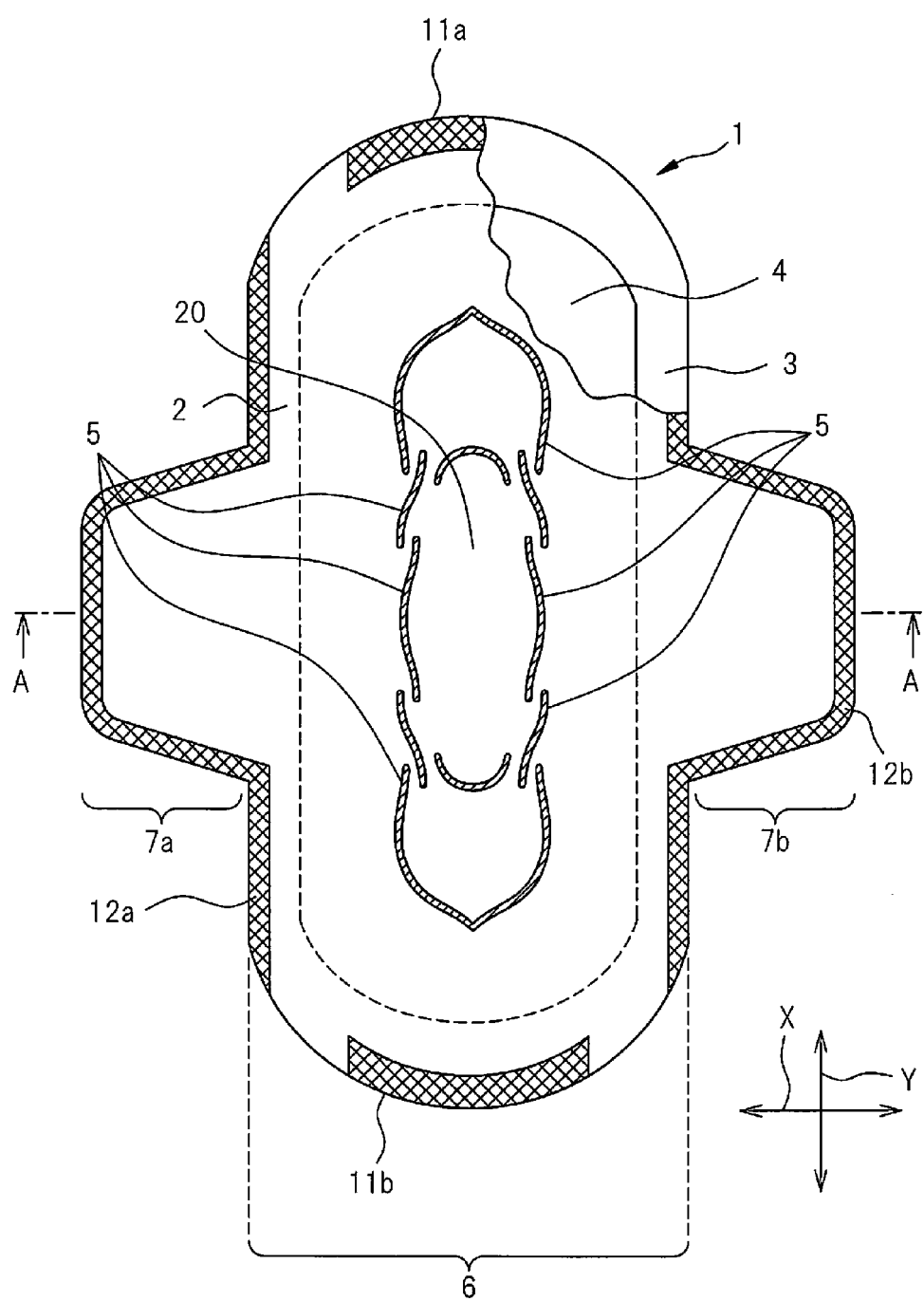
FIG. 1 is a partial cutaway plan view of a sanitary napkin according to an embodiment of the invention.

The absorbent article of the invention will now be described.
The absorbent article according to mode 1 is an absorbent article comprising a liquid-permeable layer, a liquid-impermeable layer, an absorbent body provided between the liquid-permeable layer and the liquid-impermeable layer, and a joining section that joins the liquid-permeable layer and the absorbent body, wherein the absorbent body contains, as constituent fibers, cellulose-based water-absorbent fibers (hereunder also abbreviated as "water-absorbent fibers"), and thermoplastic resin fibers that include an unsaturated carboxylic acid, an unsaturated carboxylic anhydride or a mixture thereof as the monomer component (hereunder also abbreviated as "thermoplastic resin fibers"), the difference between the dry Gurley bending resistance and the wet Gurley bending resistance of the joining section being 2.5 mN/12.5 mm or less.

With the absorbent article of mode 1, sufficient strength is maintained before and after fluid absorption by the absorbent body (this, not only when dry but also when wet), by an intricate network formed between the fibers of the absorbent body, and it is therefore possible to obtain a difference between the dry Gurley bending resistance and wet Gurley bending resistance of the joining section (dry Gurley bending resistance–wet Gurley bending resistance) of 2.5 mN/12.5 mm or smaller. Thus, in an absorbent article according to mode 1, the flexural rigidity of the joining section is maintained at a set value or less, before and after fluid absorption. Therefore, even when fluid is absorbed and the strength of the absorbent body is reduced, resulting in reduced flexural rigidity of the joining section, it is possible to effectively prevent reduction in the adhesiveness of the top sheet on the wearer and deformation of the absorbent body, due to the difference between the dry flexural rigidity and the wet flexural rigidity of the joining section, as well as consequent leakage of fluids or an uncomfortable feeling for the wearer. It is an essential condition for the absorbent body that it contains thermoplastic resin fibers including an unsaturated carboxylic acid, an unsaturated carboxylic anhydride or a mixture thereof as a monomer component, in order to produce a difference of 2.5 mN/12.5 mm or less between the dry Gurley bending resistance and the wet Gurley bending resistance of the joining section.

In a preferred mode (mode 2) of the absorbent article according to mode 1, the mass ratio of the thermoplastic resin fibers is 1/9 to 5/5 with respect to the water-absorbent fibers present in the absorbent body.

For the absorbent article of mode 2, the lower limit of 1/9 is set from the viewpoint of the strength of the absorbent body (especially the wet strength after fluid absorption), while the upper limit of 5/5 is set from the viewpoint of the fluid absorption property of the absorbent body, and if the mass ratio of thermoplastic resin fibers with respect to water-absorbent fibers is 1/9 to 5/5, the absorbent body will have both sufficient strength (especially wet strength after fluid absorption) and a sufficient fluid absorption property.

In a preferred mode (mode 3) of the absorbent article of mode 2, the dry Gurley bending resistance of the joining section is 4.82 to 6.09 mN/12.5 mm, and the wet Gurley bending resistance of the joining section is 2.32 to 3.98 mN/12.5 mm.

Since a dry Gurley bending resistance of 4.82 to 6.09 mN/12.5 mm for the joining section and a wet Gurley bending resistance of 2.32 to 3.98 mN/12.5 mm for the joining section are obtained with the absorbent article of mode 3, the joining section has sufficient dry flexural rigidity and wet flexural rigidity. It is an essential condition for the mass ratio of thermoplastic resin fibers with respect to water-absorbent fibers to be 1/9 to 5/5, in order to obtain a dry Gurley bending resistance of 4.82 to 6.09 mN/12.5 mm for the joining section and a wet Gurley bending resistance of 2.32 to 3.98 mN/12.5 mm for the joining section.

In a preferred mode (mode 4) of the absorbent article of mode 2 or mode 3, the dry bonding strength of the joining section is 1.53 to 7.65 N/25 mm and the wet bonding strength of the joining section is 0.95 to 4.34 N/25 mm.

Since a dry bonding strength of 1.53 to 7.65 N/25 mm for the joining section and a wet bonding strength of 0.95 to 4.34 N/25 mm for the joining section are obtained with the absorbent article of mode 4, it is possible to effectively prevent interfacial peeling between the liquid-permeable layer and the absorbent body even when the absorbent body absorbs fluids and suffers reduction in strength. It is an essential condition for the mass ratio of thermoplastic resin fibers with respect to water-absorbent fibers to be 1/9 to 5/5, in order to obtain a dry bonding strength of 1.53 to 7.65 N/25 mm for the joining section and a wet bonding strength of 0.95 to 4.34 N/25 mm for the joining section.

In a preferred mode (mode 5) of the absorbent article of modes 2 to 4, the density of the absorbent body is 0.06 to 0.14 g/cm$^3$. If the mass ratio of the thermoplastic resin fibers with respect to the water-absorbent fibers in the absorbent body is 1/9 to 5/5, and the density of the absorbent body is 0.06 to 0.14 g/cm$^3$, it will be possible to impart a sufficient fluid absorption property to the absorbent body.

In a preferred mode (mode 6) of the absorbent article of mode 5, the absorbent body is obtained by spraying a mixed material containing the cellulose-based water-absorbent fibers and the thermoplastic resin fibers with high-pressure steam to increase the density.

With the absorbent article of mode 6, the density of the absorbent body is adjusted to within the desired range by increasing the density, utilizing high-pressure steam spraying. When high-pressure steam is sprayed onto a mixed material, water vapor permeates into the mixed material, and the hydrogen bonds (for example, the hydrogen bonds formed between water-absorbent fibers, between thermoplastic resin fibers and between water-absorbent fibers and thermoplastic resin fibers) are broken, thereby softening the mixed material. Thus, less pressure is required to increase the density, and the softened mixed material can be more easily adjusted in density. When the density-adjusted mixed material is dried to reform the hydrogen bonds, elastic recovery (increased bulk) of the fibers is inhibited, and the density of the absorbent body is kept within a fixed range. Mode 6 is particularly suitable when the thermoplastic resin fibers include an unsaturated carboxylic anhydride (for example, maleic anhydride or its derivative) as a monomer component. When unsaturated carboxylic anhydride groups in the thermoplastic resin fibers react with water vapor to produce unsaturated carboxylic acid groups, the number of oxygen atoms that can form hydrogen bonds increases, and therefore elastic recovery of the density-increased fibers (bulk increase) is effectively inhibited.

In a preferred mode (mode 7) of the absorbent article of mode 5 or mode 6, the basis weight of the absorbent body is 40 to 900 g/m$^2$. If the basis weight is less than 40 g/m$^2$, the amount of thermoplastic resin fibers will be insufficient, and the strength of the absorbent body (especially the wet strength after fluid absorption) may be reduced, while if it is greater than 900 g/m$^2$, the amount of thermoplastic resin fibers will become excessive and the rigidity of the absorbent body may become too high.

In a preferred mode (mode 8) of the absorbent article of mode 1 to mode 7, the joining section includes a section extending in the lengthwise direction of the absorbent article, and the dry Gurley bending resistance and wet Gurley bending resistance of the joining section are the dry Gurley bending resistance and wet Gurley bending resistance of the section extending in the lengthwise direction of the absorbent article.

In a preferred mode (mode 9) of the absorbent article according to any of modes 1 to 8, the joining section is a compressed section in which the liquid-permeable layer and the absorbent body are integrated in the thickness direction.

In a preferred mode (mode 10) of the absorbent article according to any one of modes 1 to 9, the constituent fibers of the absorbent body are bonded together. By having the constituent fibers of the absorbent body bonded together in the absorbent article of mode 10, an intricate network is formed between the fibers, so that sufficient strength is retained before and after absorption of fluids by the absorbent body (that is, not only when dry but also when wet). The manner of bonding may be, for example, bonding of thermoplastic resin fibers with thermoplastic resin fibers by heat fusion or between thermoplastic resin fibers and water-absorbent fibers, or bonding between thermoplastic resin fibers, between water-absorbent fibers or between thermoplastic resin fibers and water-absorbent fibers by hydrogen bonding. When the absorbent body includes other fibers, the thermoplastic resin fibers and/or water-absorbent fibers may be bonded with the other fibers.

In a preferred mode (mode 11) of the absorbent article of any one of modes 1 to 10, through-holes passing through the liquid-permeable layer are formed at an open area of 5% to 70%. If the open area of through-holes is less than 5%, it will not be possible to achieve sufficient improvement in liquid permeability of the liquid-permeable layer by forming the through-holes, while if the open area of through-holes is greater than 70%, rewetting of fluid from the absorbent body to the liquid-permeable layer will become notable.

In a preferred mode (mode 12) of the absorbent article of any one of modes 1 to 11, through-holes are formed passing through the liquid-permeable layer and absorbent body. With the absorbent article of mode 12, the absorption and accommodation of highly viscous fluids is increased.

In a preferred mode (mode 13) of the absorbent article according to any one of modes 1 to 12, the thermoplastic resin fibers are core-sheath composite fibers having as the sheath component a modified polyolefin that has been graft-polymerized with a vinyl monomer comprising an unsaturated carboxylic acid, an unsaturated carboxylic anhydride or a mixture thereof, or a polymer blend of the modified polyolefin with another resin, and as the core component a resin with a higher melting point than the modified polyolefin.

In a preferred mode (mode 14) of the absorbent article according to any one of modes 1 to 13, the unsaturated carboxylic acid, unsaturated carboxylic anhydride or mixture thereof is maleic acid or its derivative, maleic anhydride or its derivative, or a mixture thereof.

In a preferred mode (mode 15) of the absorbent article according to any one of modes 1 to 14, the absorbent body contains a high-water-absorbing material. With the absorbent article of mode 15, the fluid absorption property of the absorbent body is improved. Since hydrogen bonds are broken by fluid absorbed into the absorbent body, swelling of the high-water-absorbing material in the absorbent body is not inhibited.

In a preferred mode (mode 16) of the absorbent article according to any one of modes 1 to 15, the thermoplastic resin fibers in the absorbent body are colored. With the absorbent article of mode 16, it is easy to visually confirm whether or not the water-absorbent fibers and the thermoplastic resin fibers are evenly dispersed. The color of the absorbed fluid may also be masked. For example, coloration may be blue when the fluid to be absorbed is urine or it may be green when it is menstrual blood, thereby providing the wearer with a more hygienic feel.

In a preferred mode (mode 17) of the absorbent article according to any one of modes 1 to 16, the liquid-permeable layer and absorbent body are bonded by an adhesive, and the liquid-permeable layer includes a blood slipping agent having a 40° C. kinematic viscosity of 0.01 to 80 mm$^2$/s, a water holding percentage of 0.01 to 4.0 mass % and a weight-average molecular weight of less than 1,000, at least in the excretory opening contact region on the skin contact surface.

With the absorbent article of mode 17, menstrual blood excreted by the wearer and reaching the excretory opening contact region slips down together with the blood slipping agent present in the excretory opening contact region, and migrates through the liquid-permeable layer into the absorbent body. The absorbent article of mode 17 therefore has improved migration of menstrual blood from the liquid-permeable layer to the absorbent body, and reduced residue of menstrual blood in the liquid-permeable layer. This prevents the skin contact surface of the liquid-permeable layer from having a sticky feel, and maintains a smooth feel. This function and effect of the blood slipping agent is exhibited regardless of changes in menstrual blood discharge during menstruation (that is, whether the amount of discharged menstrual blood is large or small).

A blood slipping agent, while exhibiting the function and effect described above, can potentially weaken the adhesive force of the adhesive when it mixes with the adhesive bonding the liquid-permeable layer and the absorbent body. In this regard, with the absorbent article of mode 17, it is possible to maintain bonding between the liquid-permeable layer and the absorbent body by the joining section even when the adhesive force of the adhesive has been weakened by the blood slipping agent.

In a preferred mode (mode 18) of the absorbent article according to mode 17, the IOB of the blood slipping agent is an IOB of 0.00 to 0.60.

In a preferred mode (mode 19) of the absorbent article according to mode 17 or mode 18, the blood slipping agent is selected from the group consisting of following items (i) to (iii), and any combination thereof:

(i) a hydrocarbon;

(ii) a compound having (ii-1) a hydrocarbon moiety and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—), inserted between a C—C single bond of the hydrocarbon moiety, and (iii-3) one or more, same or different groups selected from the group consisting of carboxyl group (—COOH) and hydroxyl group (—OH), substituting a hydrogen on the hydrocarbon moiety;

with the proviso that when two or more oxy groups are inserted in the compound of (ii) or (iii), the oxy groups are not adjacent.

In a preferred mode (mode 20) of the absorbent article of any one of modes 17 to 19, the blood slipping agent is selected from the group consisting of following items (i') to (iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety;

with the proviso that when two or more same or different bonds are inserted in the compound of (ii') or (iii'), the bonds are not adjacent.

In a preferred mode (mode 21) of the absorbent article according to any of modes 17 to 20, the blood slipping agent is selected from the group consisting of following items (A) to (F), as well as any combination thereof:

(A) an ester of (A1) a compound having a chain hydrocarbon moiety and 2-4 hydroxyl groups substituting hydrogens on the chain hydrocarbon moiety, and (A2) a compound having a chain hydrocarbon moiety and one carboxyl group substituting a hydrogen on the chain hydrocarbon moiety;

(B) an ether of (B1) a compound having a chain hydrocarbon moiety and 2-4 hydroxyl groups substituting hydrogens on the chain hydrocarbon moiety, and (B2) a compound having a chain hydrocarbon moiety and one hydroxyl group substituting a hydrogen on the chain hydrocarbon moiety;

(C) an ester of (C1) a carboxylic acid, hydroxy acid, alkoxy acid or oxoacid containing a chain hydrocarbon moiety and 2-4 carboxyl groups substituting hydrogens on the chain hydrocarbon moiety, and (C2) a compound having a chain hydrocarbon moiety and one hydroxyl group substituting a hydrogen on the chain hydrocarbon moiety;

(D) a compound having a chain hydrocarbon moiety, and one bond selected from the group consisting of ether bond (—O—), carbonyl bond (—CO—), ester bond (—COO—) and carbonate bond (—OCOO—), inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

In a preferred mode (mode 22) of the absorbent article according to any of modes 17 to 21, the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycol and at least one fatty acid, ($e_3$) an ether of a polyoxy $C_3$-$C_6$ alkylene glycol and at least one aliphatic monohydric alcohol, and ($f_1$) a chain alkane, as well as any combination thereof.

There are no particular restrictions on the type and usage of the absorbent article of the invention. For example, absorbent articles include sanitary products and sanitary articles, such as sanitary napkins, disposable diapers, panty liners, incontinence pads and perspiration sheets, which may be for humans or animals other than humans, such as pets. There are no particular restrictions on the fluid to be absorbed by the absorbent article, and for example, it may be liquid excreta excreted by the wearer (for example, menstrual blood, urine or vaginal discharge).

Embodiments of the absorbent article of the invention will now be described, using a sanitary napkin as an example, with reference to the accompanying drawings.

Figure 2:
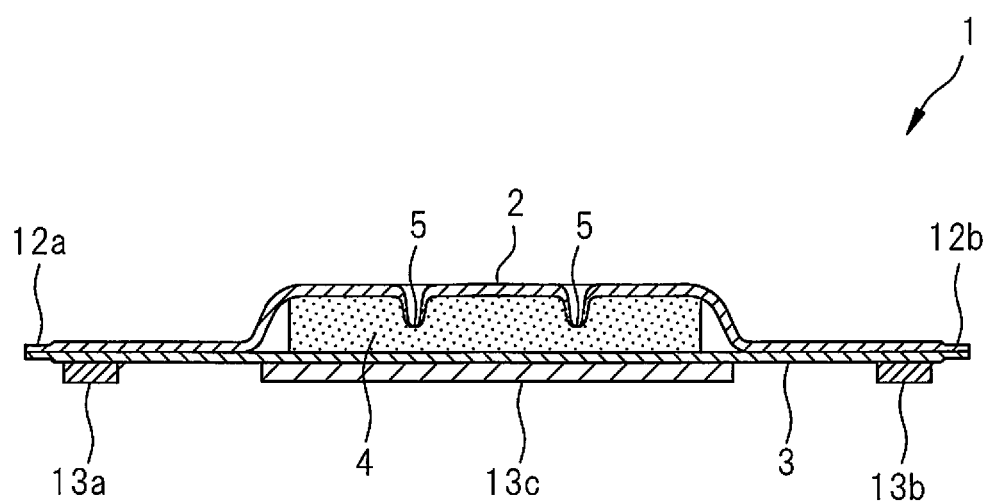
FIG. 2 is a cross-sectional view of FIG. 1 along line A-A.

As shown in FIG. 1 and FIG. 2, the sanitary napkin 1 according to one embodiment of the invention comprises a liquid-permeable top sheet 2, a liquid-impermeable back sheet 3, an absorbent body 4 formed between the top sheet 2 and the back sheet 3, and compressed sections 5 integrating the top sheet 2 and absorbent body 4 in the thickness direction. In FIG. 1, the X-axial direction is the widthwise direction of the sanitary napkin 1, the Y-axial direction is the lengthwise direction of the sanitary napkin 1, and the direction of the plane extending in the X-axial and Y-axial directions corresponds to the planar direction of the sanitary napkin 1. The same applies to the other drawings as well.

The sanitary napkin 1 is worn to absorb liquid excreta (such as menstrual blood) excreted by the wearer. It is worn in such a manner that the top sheet 2 is on the skin side of the wearer, and the back sheet 3 is located on the side of the clothing (underwear) of the wearer. The liquid excreta excreted by the wearer permeates the top sheet 2 and reaches the absorbent body 4, and is absorbed and retained in the absorbent body 4. Leakage of liquid excreta that has been absorbed and retained in the absorbent body 4 is prevented by the back sheet 3.

As shown in FIG. 1, the top sheet 2 and back sheet 3 have their edges bonded together in the lengthwise direction by seal sections 11a, 11b, forming the body section 6, while having their edges bonded together in the widthwise direction by seal sections 12a, 12b, forming essentially rectangular wing sections 7a, 7b that extend out in the widthwise direction from the body section 6.

The shape of the body section 6 may be appropriately modified within a range suitable for the female body and underwear, and for example, it may be roughly rectangular, roughly elliptical or roughly gourd-shaped. The dimensions in the lengthwise direction of the body section 6 will usually be 100 to 500 mm and preferably 150 to 350 mm, while the dimensions in the widthwise direction of the body section 6 will usually be 30 to 200 mm and preferably 40 to 180 mm.

The bonding method for the seal sections 11a, 11b, 12a, 12b may be embossing, ultrasonic waves or a hot-melt adhesive. In order to increase the bonding strength, two or more different bonding methods may be combined (for example, bonding with a hot-melt adhesive followed by embossing).

As an example of embossing, the top sheet 2 and back sheet 3 may be passed together between an embossing roll, having heights corresponding to the emboss pattern to be formed, and a flat roll, for embossing (a method known as round sealing). By heating the embossing roll and/or flat roll by this method, each sheet is softened so that the seal sections become more distinct. Examples of emboss patterns include lattice-like patterns, zigzag patterns and wavy patterns. In order to impede bending of the sanitary napkin 1 at the borders of the seal sections, the emboss pattern is preferably intermittently elongated.

Examples of hot-melt adhesives include pressure-sensitive adhesives and heat-sensitive adhesives composed mainly of rubber-based compounds, such as styrene-ethylene-butadiene-styrene (SEBS), styrene-butadiene-styrene (SBS) or styrene-isoprene-styrene (SIS), or composed mainly of olefin-based compounds, such as linear low-density polyethylene; and water-sensitive adhesives comprising water-soluble polymers (such as polyvinyl alcohol, carboxylmethyl cellulose and gelatin) or water-swelling polymers (such as polyvinyl acetate and sodium polyacrylate). Examples of adhesive coating methods include spiral coating application, coater application, curtain coater application and summit-gun coating.

As shown in FIG. 2, pressure-sensitive adhesive sections 13a, 13b are provided on the clothing side of the back sheet 3 forming the wing sections 7a, 7b, and a pressure-sensitive adhesive section 13c is provided on the clothing side of the back sheet 3 forming the body section 6. The pressure-sensitive adhesive section 13c is attached to the crotch section of underwear, while the wing sections 7a, 7b are folded toward the outer wall of the underwear and the pressure-sensitive adhesive sections 13a, 13b are attached to the crotch section of the underwear, thereby stably anchoring the sanitary napkin 1 to the underwear.

Examples of pressure-sensitive adhesives to be used in the pressure-sensitive adhesive sections 13a, 13b, 13c include styrene-based polymers, such as styrene-ethylene-butylene-styrene block copolymer, styrene-butylene polymer, styrene-butylene-styrene block copolymer and styrene-isobutylene-styrene copolymer; tackifiers, such as C5 petroleum resins, C9 petroleum resins, dicyclopentadiene-based petroleum resins, rosin-based petroleum resins, polyterpene resins and terpenephenol resins; monomer plasticizers, such as tricresyl phosphate, dibutyl phthalate and dioctyl phthalate, and polymer plasticizers, such as vinyl polymer and polyester.

The top sheet 2 is a sheet that allows permeation of liquid excreta excreted by the wearer, an example thereof being a liquid-permeable layer. One side of the top sheet 2 is the side in contact with the skin of the wearer.

The top sheet 2 is not particularly restricted so long as it allows permeation of liquid excreta excreted by the wearer. Examples for the top sheet 2 include nonwoven fabrics, woven fabrics, liquid permeation hole-formed synthetic resin films and meshed net-like sheets, with nonwoven fabrics being preferred among these.

Examples of fibers used to form nonwoven fabrics include natural fibers (wool, cotton and the like), regenerated fibers (for example, rayon, acetate and the like), inorganic fibers (for example, glass fibers, carbon fibers and the like), synthetic resin fibers (for example, polyolefins, such as polyethylene, polypropylene, polybutylene, ethylene-vinyl acetate copolymer, ethylene-ethyl acrylate copolymer, ethylene-acrylic acid copolymer, and ionomer resins; polyesters, such as polyethylene terephthalate, polybutylene terephthalate, polytrimethylene terephthalate and polylactic acid, and polyamides, such as nylon). The nonwoven fabric may be combined with composite fibers, such as core/sheath fibers, side-by-side fibers and sea/island fibers, hollow type fibers; irregularly shaped fibers, such as flat fibers, Y-shaped fibers or C-shaped fibers; solid crimped fibers, such as latent crimped or developed crimped fibers, or split fibers that have been split by a physical load, such as a water stream, heat, embossing or the like.

Examples for the method of producing a nonwoven fabric include forming a web (fleece) and physically or chemically bonding the fibers together, where methods for forming a web include spunbond methods, dry methods (carding methods, spunbond methods, meltblown methods and airlaid methods), and wet methods, and bonding methods include thermal bond methods, chemical bond methods, needle punching methods, stitch bond methods and spunlace methods. Instead of a nonwoven fabric produced as described above, spunlace formed into a sheet by a hydroentangling method may be used as the top sheet 2. There may also be used for the top sheet 2 a nonwoven fabric having concavoconvexities on the skin side (for example, a nonwoven fabric having a lower layer side with heat-shrinkable fibers or the like, which contracts to form concavoconvexities on the upper layer side, or a nonwoven fabric in which concavoconvexities are formed by applying air during web formation). Forming irregularities on the skin side in this manner can reduce the contact area between the top sheet 2 and the skin.

The top sheet 2 preferably has through-holes running through the top sheet 2. When the top sheet 2 has through-holes (for example, a porous film or porous nonwoven fabric), the open area of the through-holes (the total proportion of the area of the through-holes with respect to the area of the top sheet 2) is preferably 5 to 70% and more preferably 10% to 40%. If the open area of through-holes is less than 5%, it will not be possible to achieve sufficient improvement in liquid permeability of the top sheet 2, while if the open area of through-holes is greater than 70%, rewetting of fluid from the absorbent body 4 to the top sheet 2 will become notable. The diameters of the through-holes are preferably 0.01 to 5 mm and more preferably 0.5 to 3 mm, and the spacing of the through-holes is preferably 0.02 to 20 mm and more preferably 1 to 10 mm.

The thickness, basis weight and density of the top sheet 2 can be appropriately adjusted in ranges that allow permeation of liquid excreta excreted by the wearer. When a nonwoven fabric is used as the top sheet 2, the size, fiber length and density of the fibers composing the nonwoven fabric and the basis weight and thickness of the nonwoven fabric may be appropriately adjusted from the viewpoint of permeability of liquid excreta and feel on the skin.

From the viewpoint of increasing the concealing property of the top sheet 2, an inorganic filler, such as titanium oxide, barium sulfate or calcium carbonate may be added to the nonwoven fabric used as the top sheet 2. When the nonwoven fabric fibers are core-sheath type composite fibers, the inorganic filler may be added only to the core or only to the sheath.

In addition to the top sheet 2, the sanitary napkin 1 may be provided with a second sheet positioned between the top sheet 2 and the absorbent body 4, as a liquid-permeable layer. The second sheet used may be a sheet, such as a nonwoven fabric described for the top sheet 2, selected as appropriate.

The back sheet 3 is a sheet that does not allow permeation of liquid excreta excreted by the wearer, an example thereof being a liquid-impermeable layer. One side of the back sheet is the side that contacts with the clothing (underwear) of the wearer. The back sheet 3 is preferably moisture-permeable in addition to being liquid-impermeable, in order to reduce mustiness during wear.

The back sheet 3 is not particularly restricted so long as it does not allow permeation of liquid excreta excreted by the wearer. Examples for the back sheet 3 include waterproof treated nonwoven fabrics, films of synthetic resins (such as polyethylene, polypropylene and polyethylene terephthalate), composite sheets comprising nonwoven fabrics and synthetic resin films (such as composite films having an air permeable synthetic resin film bonded to a spunbond or spunlace nonwoven fabric), and SMS nonwoven fabrics comprising a highly water-resistant meltblown nonwoven fabric sandwiched between high-strength spunbond nonwoven fabrics.

An adhesive (for example a hot-melt adhesive) is coated at the interface between the top sheet 2 and the absorbent body 4, and the interface between the back sheet 3 and the absorbent body 4, and the top sheet 2 is bonded on the one side of the absorbent body 4 while the back sheet 3 is bonded on the other side. From the viewpoint of liquid permeability from the top sheet 2 to the absorbent body 4, the adhesive is not coated over the entire interface between the top sheet 2 and the absorbent body 4, and for example, it is coated in a dotted, spiral, stripe or other pattern. Examples of adhesives include pressure-sensitive adhesives and heat-sensitive adhesives composed mainly of rubber-based compounds, such as styrene-ethylene-butadiene-styrene (SEBS), styrene-butadiene-styrene (SBS) or styrene-isoprene-styrene (SIS), or composed mainly of olefin-based compounds, such as linear low-density polyethylene; and water-sensitive adhesives comprising water-soluble polymers (such as polyvinyl alcohol, carboxylmethyl cellulose and gelatin) or water-swelling polymers (such as polyvinyl acetate and sodium polyacrylate). Examples of adhesive coating methods include spiral coating application, coater application, curtain coater application and summit-gun coating. The coating amount (basis weight) of the adhesive will usually be 0.5 to 20 $g/m^2$ and is preferably 2 to 10 $g/m^2$.

The absorbent body 4 comprises, as constituent fibers, cellulose-based water-absorbent fibers (hereunder also abbreviated as "water-absorbent fibers"), and thermoplastic resin fibers that include an unsaturated carboxylic acid, an unsaturated carboxylic anhydride or a mixture thereof as the monomer component (hereunder also abbreviated as "thermoplastic resin fibers"). The water-absorbent fibers mainly contribute to the fluid absorption property and retention of the absorbent body 4, while the thermoplastic resin fibers contribute mainly to the strength of the absorbent body 4 (especially the wet strength after fluid absorption).

The water-absorbent fibers and thermoplastic resin fibers are present in the absorbent body 4 in a mixed state. The intersections between the fibers (for example, the intersections between the thermoplastic resin fibers or the intersections between the thermoplastic resin fibers and the water-absorbent fibers) are bonded by heat fusion of the thermoplastic resin fibers. This improves the strength of the absorbent body 4 (especially the wet strength after fluid absorption). The fibers are also forcefully tangled, and bonded by hydrogen bonds formed between the thermoplastic resin fibers, between the water-absorbent fibers or between the thermoplastic resin fibers and water-absorbent fibers. When the absorbent body 4 includes other fibers, the thermoplastic resin fibers and/or water-absorbent fibers may be bonded with the other fibers.

The heat fusion is accomplished, for example, by heating the mixed material comprising the water-absorbent fibers and thermoplastic resin fibers at a temperature above the melting point of the thermoplastic resin fibers. The heating temperature may be appropriately adjusted depending on the type of thermoplastic resin fibers. The temperature above the melting point of the thermoplastic resin fibers may be any that is above the temperature at which a portion of the thermoplastic resin fibers melt, and when the thermoplastic resin fibers are core-sheath composite fibers, for example, it may be above the temperature at which the sheath component melts.

Heat fusion may be carried out, for example, by blasting a mixed material containing water-absorbent fibers and thermoplastic resin fibers with hot air at 130° C. to 220° C. and preferably 140° C. to 180° C., for 0.5 to 60 seconds and preferably 5 to 30 seconds at an airflow rate of 2.5 to 30 m/sec and preferably 5 to 20 m/sec. The hot air blasting can be accomplished with an air-through system, for example. Hot air blasting is merely an example of heat treatment. The heat treatment is not particularly restricted so long as it allows heating to or above the melting point of the thermoplastic resin fibers. The heat treatment can be carried out using hot air, or another heating medium, such as microwaves, steam or infrared rays.

The absorbent body 4 may be in a form in which a core containing water-absorbent fibers and thermoplastic resin fibers is coated with a core wrap. The core wrap is not particularly restricted so long as it has liquid permeability and absorbent body retentivity. Examples for the core wrap include nonwoven fabrics, woven fabrics, liquid permeation hole-formed synthetic resin films and meshed net-like sheets.

The mass ratio of the thermoplastic resin fibers with respect to the water-absorbent fibers in the absorbent body 4 (thermoplastic resin fibers/water-absorbent fibers) is preferably 1/9 or greater. The lower limit of 1/9 is set from the viewpoint of the strength of the absorbent body 4 (especially the wet strength after fluid absorption), and if the mass ratio of thermoplastic resin fibers with respect to water-absorbent fibers is at least 1/9, the absorbent body 4 will maintain sufficient strength before and after fluid absorption (that is, not only when dry but also when wet).

A larger mass ratio of thermoplastic resin fibers with respect to water-absorbent fibers in the absorbent body 4 (thermoplastic resin fibers/water-absorbent fibers) will result in greater strength of the absorbent body 4. For example, the strength of the absorbent body 4 increases as the mass ratio of the thermoplastic resin fibers with respect to the water-absorbent fibers increases from 1/9, 1.5/8.5, 2/8, 2.5/7.5, 3/7, 3.5/6.5, 4/6 to 4.5/5.5. Thus, considering that mass ratios of 1/9, 1.5/8.5, 2/8, 2.5/7.5, 3/7, 3.5/6.5, 4/6 and 4.5/5.5 correspond to increasing strength of the absorbent body 4, significance may be found in the lower limit for the mass ratio of the thermoplastic resin fibers with respect to the water-absorbent fibers.

The upper limit for the mass ratio of the thermoplastic resin fibers with respect to the water-absorbent fibers in the absorbent body 4 (thermoplastic resin fibers/water-absorbent fibers) is preferably 5/5. The upper limit of 5/5 is set from the viewpoint of the fluid absorption property of the absorbent body 4, and if the mass ratio of thermoplastic resin fibers with respect to water-absorbent fibers is 5/5 or less, the absorbent body 4 will also have a sufficient fluid absorption property.

A smaller mass ratio of thermoplastic resin fibers with respect to water-absorbent fibers in the absorbent body 4 (thermoplastic resin fibers/water-absorbent fibers) will result in a weaker influence of the hydrophobicity of the thermoplastic resin fibers, and a greater fluid absorption property of the absorbent body 4. For example, the fluid absorption property of the absorbent body 4 increases as the mass ratio of the thermoplastic resin fibers with respect to the water-absorbent fibers decreases from 5/5, 4.5/5.5, 4/6, 3.5/6.5, 3/7, 2.5/7.5, 2/8 to 1.5/8.5. Thus, considering that mass ratios of 5/5, 4.5/5.5, 4/6, 3.5/6.5, 3/7, 2.5/7.5, 2/8 and 1.5/8.5 correspond to an increasing fluid absorption property of the absorbent body 4, significance may be found in the upper limit for the mass ratio of the thermoplastic resin fibers with respect to the water-absorbent fibers.

The mass ratio of the thermoplastic resin fibers with respect to the water-absorbent fibers in the absorbent body 4 (thermoplastic resin fibers/water-absorbent fibers) is preferably 1/9 to 5/5 and more preferably 2/8 to 4/6, from the viewpoint of the strength of the absorbent body 4 (especially the wet strength after fluid absorption) and the fluid absorption property. This will allow the absorbent body 4 to have sufficient strength (especially wet strength after fluid absorption) and a sufficient fluid absorption property.

The density of the absorbent body 4 is preferably 0.06 to 0.14 g/cm$^3$, more preferably 0.07 to 0.12 g/cm$^3$ and even more preferably 0.08 to 0.1 g/cm$^3$. If the mass ratio of the thermoplastic resin fibers with respect to the water-absorbent fibers in the absorbent body 4 is 1/9 to 5/5, and the density of the absorbent body 4 is 0.06 to 0.14 g/cm$^3$, it will be possible to impart a sufficient fluid absorption property to the absorbent body 4.

The density of the absorbent body 4 is calculated by the following formula.

$$D(\text{g/cm}^3)=B(\text{g/m}^2)/T(\text{mm})\times10^{-3}$$

wherein D, B and T represent the density, basis weight and thickness, respectively, of the absorbent body 4.

The basis weight (g/m$^2$) of the absorbent body 4 is calculated by the following formula.

Three 100 mm×100 mm sample pieces are cut out from the absorbent body 4, the mass of each sample piece is measured under standard conditions (temperature: 23±2° C., relative humidity: 50±5%) using a digital balance (for example, electronic scale HF-300 by Kensei Co., Ltd.), and the mass per unit area (g/m$^2$) of the absorbent body 4 calculated from the average of the three measured values is recorded as the basis weight of the absorbent body 4.

Any measuring conditions not specified above for measurement of the basis weight of the absorbent body 4, are the measuring conditions described in ISO 9073-1 or JIS L 1913 6.2.

Measurement of the thickness (mm) of the absorbent body 4 is conducted in the following manner.

Using a thickness gauge (for example, an FS-60DS by Daiei Kagaku Seiki Mfg. Co., Ltd., measuring surface: 44 mm (diameter), measuring pressure: 3 g/cm$^2$), five different locations of the absorbent body 4 (a diameter of 44 mm for each site when an FS-60DS thickness gauge is used) are pressed at a constant pressure of 3 g/cm$^2$ under standard conditions (temperature: 23±2° C., relative humidity: 50±5%), the thickness is measured after 10 seconds of pressing at each site, and the mean value of the five measured values is recorded as the thickness of the absorbent body 4.

The density of the absorbent body 4 may be adjusted to the prescribed range by increasing the density of a mixed material comprising the water-absorbent fibers and thermoplastic resin fibers. In order to maintain a fixed range for the density of the absorbent body 4, it is necessary to minimize elastic recovery of the fibers and maintain a fixed range for the bulk of the absorbent body 4. This allows hydrogen bonding (for example, hydrogen bonding formed between water-absorbent fibers, between thermoplastic resin fibers and between the water-absorbent fibers/thermoplastic resin fibers) to contribute to maintaining the bulk of the absorbent body 4. Hydrogen bonds are formed, for example, between the oxygen atoms of the thermoplastic resin fibers (for example, the oxygen atoms of carboxyl, acyl and ether bonds) and the hydrogens of cellulose (for example, hydroxyl hydrogens). Since the hydrogen bonds are broken by liquid absorbed into the absorbent body 4, they do not inhibit swelling of the absorbent material present in the absorbent body 4 (the water-absorbent fibers, as an essential component, and the high-water-absorbing material, as an optional component).

The dry maximum tensile strength of the absorbent body 4 (the maximum tensile strength for a basis weight of 200 g/m$^2$) is preferably between 3 and 36 N/25 mm and more preferably between 8 and 20 N/25 mm, and the wet maximum tensile strength of the absorbent body 4 (the maximum tensile strength for a basis weight of 200 g/m$^2$) is preferably between 2 and 32 N/25 mm and more preferably between 5 and 15 N/25 mm. This will allow the absorbent body 4 to maintain sufficient strength before and after fluid absorption (that is, not only when dry but also when wet). It is an essential condition for the mass ratio of the thermoplastic resin fibers with respect to the water-absorbent fibers in the absorbent body 4 to be at least 1/9 in order to achieve such strength for the absorbent body 4.

As regards the maximum tensile strength of the absorbent body 4, "N/25 mm" means the maximum tensile strength (N) per 25 mm width in the planar direction of the absorbent body 4, the planar direction of the absorbent body 4 being, for example, the machine direction (MD direction) during production of the absorbent body 4 or the direction perpendicular to the MD direction (the CD direction), but preferably the MD direction.

Measurement of the dry maximum tensile strength of the absorbent body 4 is conducted in the following manner.

A sample piece (150 mm length×25 mm width) was mounted on a tensile tester (AG-1kNI by Shimadzu Corp.) under standard conditions (environment temperature: 20° C., humidity: 60%), with a grip spacing of 100 mm, a load (maximum point load) was applied at a pull rate of 100 mm/min until the sample piece was severed, and the maximum tensile strength (N/25 mm) was measured. The denotation "N/25 mm" means the maximum tensile strength (N) per 25 mm width in the lengthwise direction of the sample piece.

Measurement of the wet maximum tensile strength of the absorbent body 4 is conducted in the following manner.

The maximum tensile strength (N/25 mm) is measured in the same manner as the dry maximum tensile strength, after dipping a sample piece (150 mm length×25 mm width) in ion-exchanged water until it sinks under its own weight, or after immersing the sample piece in water for 1 hour or longer. The denotation "N/25 mm" means the maximum tensile strength (N) per 25 mm width in the lengthwise direction of the sample piece.

Any measuring conditions not specified for measurement of the dry and wet maximum tensile strengths are the measuring conditions described in ISO 9073-3 or JIS L 1913 6.3.

The difference between the dry maximum tensile strength and the wet maximum tensile strength of the absorbent body 4 (dry maximum tensile strength−wet maximum tensile strength) is preferably 1 to 5 N/25 mm and more preferably 2 to 4 N/25 mm. This will allow the absorbent body 4 to maintain sufficient strength before and after fluid absorption (that is, not only when dry but also when wet). It is an essential condition for the mass ratio of the thermoplastic resin fibers with respect to the water-absorbent fibers in the absorbent body 4 to be at least 1/9 in order to achieve such strength for the absorbent body 4. Since the hydrogen bonds formed during dryness are broken when wet, the difference between the dry maximum tensile strength and the wet maximum tensile strength is an indicator of the extent of hydrogen bonding.

Examples of cellulose-based water-absorbent fibers to be contained in the absorbent body 4 include wood pulp obtained using conifers or broadleaf trees as starting materials (for example, mechanical pulp, such as groundwood pulp, refiner ground pulp, thermomechanical pulp and chemithermomechanical pulp; chemical pulp, such as Kraft pulp, sulfide pulp and alkaline pulp; and semichemical pulp); mercerized pulp or crosslinked pulp obtained by chemical treatment of wood pulp; nonwood pulp, such as bagasse, kenaf, bamboo, hemp and cotton (for example, cotton linter); and regenerated fiber, such as rayon fiber.

The thermoplastic resin fibers in the absorbent body 4 are not particularly restricted so long as they are thermoplastic resin fibers comprising an unsaturated carboxylic acid, an unsaturated carboxylic anhydride or a mixture thereof as the monomer component, and they may be appropriately selected from the viewpoint of strength, hydrogen bonding properties and heat sealability.

Examples of thermoplastic resin fibers to be contained in the absorbent body 4 include core-sheath composite fibers having as the sheath component a modified polyolefin that has been graft-polymerized with a vinyl monomer comprising an unsaturated carboxylic acid, an unsaturated carboxylic anhydride or a mixture thereof, or a polymer blend of the modified polyolefin with another resin, and as the core component a resin with a higher melting point than the modified polyolefin.

Examples of unsaturated carboxylic acids or unsaturated carboxylic anhydrides include vinyl monomers, such as maleic acid and its derivatives, maleic anhydride and its derivatives, fumaric acid and its derivatives, malonic acid and its unsaturated derivatives and unsaturated derivatives of succinic acid, and other vinyl monomers including radical-polymerizing general purpose monomers, for example, styrenes, such as styrene and α-methylstyrene; and (meth) acrylic acid esters, such as methyl (meth)acrylate, ethyl (meth)acrylate, 2-hydroxyethyl (meth)acrylate and dimethylaminoethyl (meth)acrylate. Examples of maleic acid derivatives and maleic anhydride derivatives include citraconic acid, citraconic anhydride and pyrocinchonic anhydride, examples of fumaric acid derivatives and malonic acid unsaturated derivatives include 3-butene-1,1-dicarboxylic acid, benzylidenemalonic acid and isopropylidenemalonic acid, and examples of succinic acid unsaturated derivatives include itaconic acid and itaconic anhydride.

The trunk polymer of a modified polyolefin may be straight-chain low-density polyethylene (LLDPE), low-density polyethylene (LDPE), medium-density polyethylene (MDPE), high-density polyethylene (HDPE), polypropylene, polybutylene, or a copolymer composed mainly of the foregoing (for example, ethylene-vinyl acetate copolymer (EVA), ethylene-ethyl acrylate copolymer (EEA), ethylene-acrylic acid copolymer (EAA) or an ionomer resin).

Graft polymerization of a vinyl monomer on a trunk polymer may be accomplished by a common method, for example, by a method of using a radical initiator, mixing an unsaturated carboxylic acid or unsaturated carboxylic anhydride and a vinyl monomer with a polyolefin and introducing side chains of a random copolymer, or a method of successively polymerizing different monomers and introducing side chains of a block copolymer.

The sheath component may be a modified polyolefin alone, or it may be a polymer blend of a modified polyolefin and another resin. The other resin is preferably a polyolefin, and more preferably the same polyolefin as the trunk polymer of the modified polyolefin. For example, when the trunk polymer is polyethylene the other resin is preferably also polyethylene.

The resin to be used as the core component is not particularly restricted so long as it is a resin with a higher melting point than the modified polyolefin, and for example, it may be a polyamide, such as 6-nylon or 6,6-nylon; a polyester of a straight-chain or branched polyhydroxyalkane acid up to C20, such as polyethylene terephthalate (PET), polytrimethylene terephthalate (PTT), polybutylene terephthalate (PBT), polylactic acid or polyglycolic acid, or a copolymer composed mainly thereof, or a copolymerized polyester composed mainly of an alkylene terephthalate copolymerized with a small amount of another component. PET is preferred from the viewpoint of its elastic repulsion and high cushioning properties, as well as from an economical viewpoint, since it can be commercially obtained at low cost.

Spinning can be accomplished if the composite ratio of the sheath component with respect to the core component is in the range of 10/90 to 90/10, and preferably 30/70 to 70/30. If the sheath component ratio is excessively reduced the heat sealability will be lowered, and if it is excessively increased the spinnability will be lowered.

Additives, such as antioxidants, light stabilizers, ultraviolet absorbers, neutralizers, nucleating agents, epoxy stabilizers, lubricants, antimicrobial agents, flame retardants, antistatic agents, pigments or plasticizers may also be added to the thermoplastic resin fibers in the absorbent body 4, if necessary. The thermoplastic resin fibers are preferably subjected to hydrophilicizing treatment with a surfactant, hydrophilic agent or the like.

The fiber lengths of the thermoplastic resin fibers in the absorbent body 4 are not particularly restricted, but they are preferably 3 to 70 mm and more preferably 5 to 20 mm when they are to be mixed with pulp by an airlaid system. Below this range, the number of bonding points with the water-absorbent fibers will be reduced, making it impossible to impart sufficient strength to the absorbent body 4. Above this range, the defibration property will be notably reduced, generating numerous non-defibrated fibers, and thus resulting in fabric irregularities and reduced uniformity of the absorbent body 4. The size of the thermoplastic resin fibers is preferably 0.5 to 10 dtex and more preferably 1.5 to 5 dtex. If the size is less than 0.5 dtex the defibration property will be reduced, and if it is greater than 10 dtex the number of fibers will be reduced, lowering the strength.

A three-dimensional crimped form may also be added to the thermoplastic resin fibers in the absorbent body 4. This will allow the buckling strength of the fibers to act in the thickness direction and inhibit collapse under external pressure, even when the fiber orientation is in the planar direction. The three-dimensional crimped form may be, for example, a zig-zag, Ω-shaped or spiral form, and the method of creating the three-dimensional crimped form may be, for example, shaping by machine-texturing or heat shrinkage. Machine-texturing can be controlled by circumferential speed differences in the line speed, and by the heat and pressure, for continuous linear fibers after spinning, and a greater number of crimps per unit length will increase the buckling strength against external pressure. The number of crimps will usually be 5 to 35/inch, and is preferably 15 to 30/inch. For creation of a form by heat shrinkage, for example, heat may be applied to fibers composed of two or more different resins with different melting points, to accomplish three-dimensional crimping utilizing the difference in heat shrinkage produced by the differences in melting points. The fiber cross-sectional shape may be, for example, that of eccentric type or side-by-side type core-sheath composite fibers. The heat shrinkage factor of such fibers is preferably 5-900 and more preferably 10-80%.

The absorbent body 4 preferably comprises a high-water-absorbing material (such as a high water-absorbent resin or high water-absorbent fibers) in addition to water-absorbent fibers and thermoplastic resin fibers. The content of the high-water-absorbing material will usually be 5 to 80 mass %, preferably 10 to 60 mass % and more preferably 20 to 40 mass % of the absorbent body 4. Examples of high-water-absorbing materials include starch-based, cellulose-based and synthetic polymer high-water-absorbing materials. Examples of starch-based or cellulose-based high-water-absorbing materials include starch-acrylic acid (acrylate) graft copolymer, saponified starch-acrylonitrile copolymer and crosslinked sodium carboxymethyl cellulose, and examples of synthetic polymer-based high-water-absorbing materials include polyacrylic acid salt-based, polysulfonic acid salt-based, maleic anhydride salt-based, polyacrylamide-based, polyvinyl alcohol-based, polyethylene oxide-based, polyaspartic acid salt-based, polyglutamic acid salt-based, polyalginic acid salt-based, starch-based and cellulose-based high water-absorbent resins (Superabsorbent Polymers: SAP), among which polyacrylic acid salt-based (especially sodium polyacrylate-based) high water-absorbent resins are preferred. Examples of high-water-absorbing material forms include particulate, filamentous and scaly forms, and in the case of particulates, the particle size is preferably 50 to 1000 μm and more preferably 100 to 600 μm. Measurement of the particle diameter is carried out according to the screening test method described in JIS R 6002:1998.

The thickness and basis weight of the absorbent body 4 can be appropriately adjusted according to the properties desired for the sanitary napkin 1 (for example, absorption property, strength and lightweight property). The thickness of the absorbent body 4 will usually be 0.1 to 15 mm, and is preferably 1 to 10 mm and more preferably 2 to 5 mm, while the basis weight will usually be 20 to 1000 g/m², and is preferably 40 to 900 g/m² and more preferably 100 to 400 g/m². If the basis weight is less than 40 g/m², the amount of thermoplastic resin fibers will be insufficient, and it may not be possible to retain the strength of the absorbent body 4 (especially the wet strength after fluid absorption), while if it is greater than 900 g/m², the amount of thermoplastic resin fibers will become excessive and the rigidity of the absorbent body 4 may become too high. The thickness and basis weight of the absorbent body 4 may be constant across the entire absorbent body 4, or it may partially differ.

The absorbent body 4 may be integrated with the top sheet 2 by through-holes running through the top sheet 2 and the absorbent body 4. This improves the absorption property and accommodating property for highly viscous fluids (such as menstrual blood). The open area of through-holes running through the top sheet 2 and the absorbent body 4 (the total area of through-holes with respect to the area of the top sheet 2) is preferably 0.1 to 20% and more preferably 1 to 10%, the diameters of the through-holes are preferably 0.1 to 5 mm and more preferably 0.5 to 3 mm, and the spacing of the through-holes is preferably 0.2 to 30 mm and more preferably 5 to 20 mm.

The thermoplastic resin fibers in the absorbent body 4 may be colored with a pigment or the like. This will facilitate visual confirmation of whether or not the water-absorbent fibers and the thermoplastic resin fibers are evenly dispersed. The color of the absorbed fluid may also be masked. For example, coloration may be blue when the fluid to be absorbed is urine or it may be green when it is menstrual blood, thereby providing the wearer with a more hygienic feel.

In order to impart the desired function to the absorbent body 4, there may be added silver, copper, zinc, silica, active carbon, aluminosilicate compounds, zeolite, or the like. These can impart functions, such as deodorant, antibacterial or heat-absorbing effects.

As shown in FIG. 1, the compressed sections 5 are formed intermittently on the marginal edge or surrounding portion of the excretory opening contact region 20, on the skin contact surface of the top sheet 2. The formation pattern of the compressed sections 5 may be modified as appropriate, and for example, the formation pattern when the top sheet 2 is viewed flat may be straight linear, curved linear, annular, dotted or the like.

The excretory opening contact region 20 is the region in which the excretory opening of the wearer (for example, the labia minora, labia majora, etc.) contact when the sanitary napkin 1 is worn. The excretory opening contact region 20 is defined as being essentially at the center of the absorbent body placement region. The absorbent body placement region is the region in which the absorbent body 4 overlaps the top sheet 2 when the absorbent body 4 has been projected onto the top sheet 2. The location and area of the excretory opening contact region 20 may be adjusted as appropriate. The excretory opening contact region 20 may be set to be essentially the same region as the region that actually contacts with the excretory opening, or it may be set as a larger region, but from the viewpoint of preventing leakage of liquid excreta, such as menstrual blood to the exterior, it is preferably set as a region larger than the region that actually contacts with the excretory opening. The length of the excretory opening contact region 20 will usually be 50 to 200 mm and is preferably 70 to 150 mm, and the width will usually be 10 to 80 mm and is preferably 20 to 50 mm.

The compressed sections 5 are recesses formed by heat embossing treatment. The compressed sections 5 for this embodiment are examples of joining sections that join the liquid-permeable layer and the absorbent body. The joining sections that join the liquid-permeable layer and the absorbent body may be formed by a joining method other than heat embossing treatment, such as ultrasonic embossing, hot fluid spray treatment (for example, high-pressure steam spray treatment, heated air spray treatment or the like) or a similar joining method.

In the heat embossing treatment, prescribed locations on the skin contact surface of the top sheet 2 are compressed in the thickness direction of the absorbent body 4, while being heated. This forms compressed sections 5 integrating the top sheet 2 and the absorbent body 4 in the thickness direction, as recesses.

The heat embossing treatment is carried out, for example, by a method in which the top sheet 2 and absorbent body 4 are passed together between an embossing roll with projections on the outer peripheral surface, and a flat roll having a smooth outer peripheral surface, for embossing. Heating can be accomplished during compression by heating the embossing roll and/or flat roll in this method. The heights of the embossing roll are formed to correspond to the shapes and arrangement pattern of the compressed grooves 5. The heating temperature will usually be 80° C. to 180° C. and is preferably 120° C. to 160° C., the pressure will usually be 10-3000 N/mm and is preferably 50-500 N/mm, and the treatment time will usually be 0.0001 to 5 seconds and is preferably 0.005 to 2 seconds.

With heat embossing treatment, the thermoplastic resin fibers in the absorbent body 4 undergo heat fusion with the material composing the top sheet 2, thereby integrating the top sheet 2 and the absorbent body 4. This increases the interfacial peel strength between the top sheet 2 and the absorbent body 4.

The difference between the dry Gurley bending resistance and the wet Gurley bending resistance of the compressed sections 5 (dry Gurley bending resistance-wet Gurley bending resistance) is 2.5 mN/12.5 mm or less. The sanitary napkin 1 retains sufficient strength before and after fluid absorption by the absorbent body 4 (that is, not only when dry but also when wet), due to the difference of 2.5 mN/12.5 mm or less between the dry Gurley bending resistance and the wet Gurley bending resistance of the compressed sections 5. Therefore, in the sanitary napkin 1, the flexural rigidity of the compressed sections 5 is kept to a set value or less before and after absorption of liquid excreta. As a result, even when liquid excreta is absorbed and the strength of the absorbent body 4 is reduced, resulting in reduced flexural rigidity of the compressed sections 5, it is possible to effectively prevent reduction in the adhesiveness of the top sheet 2 on the wearer and deformation of the absorbent body, due to the difference between the dry flexural rigidity and the wet flexural rigidity of the compressed sections 5, as well as the consequent leakage of liquid excreta and an uncomfortable feeling for the wearer. It is an essential condition for the absorbent body 4 that it contains thermoplastic resin fibers including an unsaturated carboxylic acid, an unsaturated carboxylic anhydride, or a mixture thereof as a monomer component, in order to produce such a difference between the dry Gurley bending resistance and the wet Gurley bending resistance of the compressed sections 5.

In regard to the Gurley bending resistance of the compressed sections 5, "mN/12.5 mm" means the Gurley bending resistance (mN) per 12.5 mm width in the extending direction of the compressed sections 5, the extending direction of the compressed sections 5 being, for example, the lengthwise direction of the sanitary napkin 1 (the machine direction (MD direction) during production) or the widthwise direction of the sanitary napkin 1 (the direction perpendicular to the MD direction (CD direction)), but it is preferably the lengthwise direction (MD direction) of the sanitary napkin 1. Thus, the dry and wet Gurley bending resistances of the compressed sections 5 are preferably the dry and wet Gurley bending resistances at the sections of the compressed sections 5 extending in the lengthwise direction of the sanitary napkin 1.

The dry Gurley bending resistance of the compressed sections 5 is preferably 4.82 mN/12.5 mm or greater, and the wet Gurley bending resistance of the compressed sections 5 is preferably 2.32 mN/12.5 mm or greater. The compressed sections 5 will thus have sufficient dry and wet Gurley bending resistance. It is an essential condition for the mass ratio of thermoplastic resin fibers with respect to water-absorbent fibers to be 1/9 or greater, in order to obtain such dry and wet Gurley bending resistances for the compressed sections 5.

If the mass ratio of the thermoplastic resin fibers with respect to the water-absorbent fibers in the absorbent body 4 (thermoplastic resin fibers/water-absorbent fibers) is 1/9 to 5/5, it will be possible to obtain a dry Gurley bending resistance of 4.82 to 6.09 mN/12.5 mm for the compressed sections 5, and a wet Gurley bending resistance of 2.32 to 3.98 mN/12.5 mm for the compressed sections 5.

The dry bonding strength of the compressed sections 5 is preferably 1.53 N/25 mm or greater, and the wet bonding strength of the compressed sections 5 is preferably 0.95 N/25 mm or greater. Therefore, the wet bonding strength of the compressed sections 5 is preferably 0.95 N/25 mm or greater. The sanitary napkin 1 can therefore effectively prevent interfacial peeling between the top sheet 2 and the absorbent body 4, even when liquid excreta are absorbed and the strength of the absorbent body 4 is reduced. It is an essential condition for the mass ratio of thermoplastic resin fibers with respect to water-absorbent fibers to be 1/9 or greater, in order to obtain such bonding strength for the compressed sections 5.

In regard to the bonding strength of the compressed sections 5, "N/25 mm" means the bonding strength (N) per 25 mm width in the extending direction of the compressed sections 5, the extending direction of the compressed sections 5 being, for example, the lengthwise direction of the sanitary napkin 1 (the machine direction (MD direction) during production) or the widthwise direction of the sanitary napkin 1 (the direction perpendicular to the MD direction (CD direction)), but it is preferably the lengthwise direction (MD direction) of the sanitary napkin 1. Thus, the dry and wet bonding strengths of the compressed sections 5 are preferably the dry and wet bonding strengths at the sections of the compressed sections 5 extending in the lengthwise direction of the sanitary napkin 1.

If the mass ratio of the thermoplastic resin fibers with respect to the water-absorbent fibers in the absorbent body 4 (thermoplastic resin fibers/water-absorbent fibers) is 1/9 to 5/5, it will be possible to obtain a dry bonding strength of 1.53 to 7.65 N/25 mm for the compressed sections 5, and a wet bonding strength of 0.95 to 4.34 N/25 mm for the compressed sections 5.

The desired dry and wet Gurley bending resistances and the desired dry and wet bonding strengths can be obtained by appropriately adjusting the heat embossing treatment conditions and the presence and type of thermoplastic resin fibers in the top sheet 2, after including in the absorbent body 4 thermoplastic resin fibers containing an unsaturated carboxylic acid, unsaturated carboxylic anhydride or its mixture as a monomer component (if necessary, also with a mass ratio of at least 1/9 for the thermoplastic resin fibers with respect to the water-absorbent fibers).

Measurement of the Gurley bending resistance of the compressed sections 5 is accomplished in the following manner.

A No. 311 Gurley flexibility tester (product of Yasuda Seiki Seisakusho Co., Ltd.) is used for measurement of the Gurley bending resistance. The tester is one that measures the flexibility (bending repulsion) of a sample piece according to JIS-L1096, the sample piece being mounted on a moving arm chuck and rotated at a fixed speed in the left-right direction, with the scale being read when the bottom edge of the sample piece separates from the pendulum, and the bending resistance S (mN) being calculated by the following formula.

$$S = R \times (D_1 W_1 + D_2 W_2 + D_3 W_3) \times (L - 12.7)^2 / b \times 3.375 \times 10^{-5}$$

wherein R is the value read from the scale pointer, $D_1$, $D_2$ and $D_3$ are the distances from the pendulum fulcrum to the weight mounting positions (25.4 mm (1 in.), 50.8 mm (2 in.), 101.6 mm (4 in.)), $W_1$, $W_2$ and $W_3$ are the masses (g) of the weights mounted at holes of $D_1$, $D_2$ and $D_3$, L is the length (mm) of the sample piece, and b is the width (mm) of the sample piece.

In this manner, the Gurley bending resistance (mN) per 12.5 mm width is measured in the lengthwise direction of the sample piece. The lengthwise direction of the sample piece may be, for example, the lengthwise direction of the sanitary napkin 1 (the machine direction (MD direction) during production) or the widthwise direction of the sanitary napkin 1 (the direction perpendicular to the MD direction (CD direction)), but it is preferably the MD direction.

For measurement of the dry Gurley bending resistance, a standard sample piece is used (environment temperature: 20° C., humidity: 60%), and for measurement of the wet Gurley bending resistance, there is used a sample piece that has been dipped in ion-exchanged water until it sinks under its own weight, or a sample piece that has been immersed in water for 1 hour or longer.

The sample piece to be used for measurement of the Gurley bending resistance is cut from the sanitary napkin 1 in such a manner as to include some of the compressed sections 5. For example, the sample piece is cut from the sanitary napkin 1 in such a manner as to include a portion of the compressed sections 5 extending in the lengthwise direction of the sanitary napkin 1. The sample piece cut out in this manner preferably has its lengthwise direction corresponding to the direction in which the compressed sections 5 extend. For example, if the sanitary napkin 1 is cut out perpendicular to the compressed sections 5 extending in the lengthwise direction, it is possible to create a sample piece having its lengthwise direction corresponding to the direction in which the compressed sections 5 extend (for example, 40 mm length×12.5 mm width). The sample piece may include or not include a portion of the back sheet 3, but from the viewpoint of increasing the measuring precision for the Gurley bending resistance of the compressed sections 5, it preferably does not include a portion of the back sheet 3.

Measurement of the dry bonding strength of the compressed sections 5 is carried out in the following manner.

A sample piece (50 mm length×25 mm width) is mounted on a tensile tester (for example, AG-1kNI by Shimadzu Corp.) under standard conditions (environment temperature: 20° C., humidity: 60%), with a grip spacing of 20 mm, the absorbent body is mounted on the upper grip and the top sheet on the lower grip, a load (maximum point load) is applied at a pull rate of 100 mm/min until the top sheet and absorbent body completely separate, and the bonding strength (N/25 mm) of the compressed sections is measured. The denotation "N/25 mm" means the bonding strength (N) per 25 mm width of the sample piece, when the lengthwise direction is oriented in the direction of tension of the sample piece.

Measurement of the wet bonding strength of the compressed sections 5 is carried out in the following manner.

This is measured in the same manner as when dry, after dipping a sample piece (50 mm length×25 mm width) in ion-exchanged water until it sinks under its own weight, or after immersing the sample piece in water for 1 hour or longer. The denotation "N/25 mm" means the bonding strength (N) per 25 mm width of the sample piece, when the lengthwise direction is oriented in the direction of tension of the sample piece.

Any measuring conditions not specified for measurement of the dry and wet bonding strengths are the measuring conditions described in ISO 9073-3 or JIS L 1913 6.3.

The sample piece used for measurement of the bonding strength is cut out from the sanitary napkin 1 in such a manner as to include compressed sections 5. For example, the sample piece is cut from the sanitary napkin 1 in such a manner as to include a portion of the compressed sections 5 extending in the lengthwise direction of the sanitary napkin 1. The sample piece cut out in this manner preferably has its lengthwise direction corresponding to the direction in which the compressed sections 5 extend. For example, if the sanitary napkin 1 is cut out perpendicular to the compressed sections 5 extending in the lengthwise direction, it is possible to create a sample piece having its lengthwise direction corresponding to the direction in which the compressed sections 5 extend (for example, 50 mm length×25 mm width).

From the viewpoint of further reinforcing the interfacial peel strength between the top sheet 2 and the absorbent body 4, the top sheet 2 preferably contains one or more different types of thermoplastic resin fibers.

The thermoplastic resin fibers in the top sheet 2 are not particularly restricted so long as the intersections between the fibers can be heat-fused. The thermoplastic resin composing the thermoplastic resin fibers may be a polyolefin, polyester, polyamide or the like.

Examples of polyolefins include straight-chain low-density polyethylene (LLDPE), low-density polyethylene (LDPE), medium-density polyethylene (MDPE), high-density polyethylene (HDPE), polypropylene, polybutylene, and copolymers composed mainly of the foregoing (for example, ethylene-vinyl acetate copolymer (EVA), ethylene-ethyl acrylate copolymer (EEA), ethylene-acrylic acid copolymer (EAA) or an ionomer resin). Polyethylene, and especially HDPE, is preferred from the viewpoint of thermal processing properties since it has a relatively low softening point of around 100° C., and also has low rigidity and a pliable feel.

Examples of polyesters include polyesters of straight-chain or branched polyhydroxyalkane acids up to C20, such as polyethylene terephthalate (PET), polytrimethylene terephthalate (PTT), polybutylene terephthalate (PBT), polylactic acid and polyglycolic acid, copolymers composed mainly thereof, and copolymerized polyesters composed mainly of alkylene terephthalates copolymerized with a small amount of another component. PET is preferred from the viewpoint of its elastic repulsion which allows formation of fibers and nonwoven fabrics with high cushioning properties, as well as from an economical viewpoint, since it can be commercially obtained at low cost.

Examples of polyamides include 6-nylon and 6,6-nylon.

The top sheet 2 may be composed of one or more different types of thermoplastic resin fibers, or it may contain other fibers that do not heat-fuse with thermoplastic resin fibers. Examples of other fibers that do not heat-fuse with thermoplastic resin fibers include regenerated fibers, such as rayon; semisynthetic fibers, such as acetate; natural fibers, such as cotton and wool; and synthetic fibers, such as polypropylene, polyethylene, polyester, nylon, polyvinyl chloride and vinylon. The amount of other fibers that do not heat-fuse with thermoplastic resin fibers will usually be 5 to 70 mass % and preferably 10 to 30 mass % of the top sheet 2.

The form of the thermoplastic resin fibers in the top sheet 2 may be, for example, core/sheath, side-by-side, or island/sea fibers. From the viewpoint of thermal bonding properties, composite fibers composed of a core and sheath are preferred. The shape of core cross-sections for core-sheath composite fibers may be, for example, circular, triangular, quadrilateral, star-shaped or the like, and the core sections may be hollow or porous. The cross-sectional area of the core/sheath structure is not particularly restricted, but is preferably 80/20 to 20/80 and even more preferably 60/40 to 40/60.

A three-dimensional crimped form may also be added to the thermoplastic resin fibers in the top sheet 2. This will allow the buckling strength of the fibers to act in the thickness direction and inhibit collapse under external pressure, even when the fiber orientation is in the planar direction. The three-dimensional crimped form may be, for example, a zig-zag, Ω-shaped or spiral form, and the method of creating the three-dimensional crimped form may be, for example, shaping by machine-texturing or heat shrinkage. Machine-texturing can be controlled by circumferential speed differences in the line speed, and by the heat and pressure, for continuous linear fibers after spinning, and a greater number of crimps per unit length will increase the buckling strength against external pressure. The number of crimps will usually be 5 to 35/inch, and is preferably 15 to 30/inch. For creation of a form by heat shrinkage, for example, heat may be applied to fibers composed of two or more different resins with different melting points, to accomplish three-dimensional crimping utilizing the difference in heat shrinkage produced by the differences in melting points. The fiber cross-sectional shape may be, for example, that of eccentric type or side-by-side type core-sheath composite fibers. The heat shrinkage factor of such fibers is preferably 5-90% and more preferably 10-80%.

The absorbent body 4 may have increased density by spraying high-pressure steam onto the mixed material containing the water-absorbent fibers and thermoplastic resin fibers. The density of the absorbent body 4 may be adjusted to within the desired range by increasing the density, utilizing high-pressure steam spraying. When high-pressure steam is sprayed onto a mixed material, water vapor permeates into the mixed material, and the hydrogen bonds (for example, the hydrogen bonds formed between water-absorbent fibers, between thermoplastic resin fibers and between water-absorbent fibers and thermoplastic resin fibers) are broken, thereby softening the mixed material. Thus, less pressure is required to increase the density, and the softened mixed material can be more easily adjusted in density. When the density-adjusted mixed material is dried to reform the hydrogen bonds, elastic recovery (increased bulk) of the fibers is inhibited, and the density of the absorbent body 4 is kept within a fixed range.

The density increase by spraying of high-pressure steam is particularly suitable when the thermoplastic resin fibers include an unsaturated carboxylic anhydride (for example, maleic anhydride or its derivative) as a monomer component. When unsaturated carboxylic anhydride groups in the thermoplastic resin fibers react with water vapor to produce unsaturated carboxylic acid groups, the number of oxygen atoms that can form hydrogen bonds increases, and therefore elastic recovery of the density-adjusted fibers (bulk increase) is effectively inhibited.

Density increase by spraying of high-pressure steam is carried out, for example, after the thermoplastic resin fibers have been bonded to the water-absorbent fibers. The temperature and vapor pressure of the high-pressure steam is appropriately adjusted depending on the desired fiber density range. The temperature of the high-pressure steam is preferably lower than the melting point of the thermoplastic resin fibers (for example, the melting point of the sheath component when the thermoplastic resin fibers are core-sheath composite fibers). The high-pressure steam is preferably sprayed at 0.03 kg/m$^2$ to 1.23 kg/m$^2$ per unit surface area. The vapor pressure of the high-pressure steam will usually be 0.1 to 2 Mpa and is preferably 0.3 to 0.8 Mpa.

When the density is to be increased by spraying high-pressure steam, the basis weight of the absorbent body 4 is preferably 40 to 900 g/m$^2$ and more preferably 100 to 400 g/m$^2$. If the basis weight is less than 40 g/m$^2$, the amount of fibers will be too low making it difficult to increase the density by spraying of high-pressure steam, while if it is greater than 900 g/m$^2$, the amount of fibers will be too great making it difficult for water vapor to permeate to the interior.

Spraying of high-pressure steam can form ridges and furrows on the surface of the absorbent body 4. The number of ridges and furrows and their spacing vary according to the number of nozzles spraying the high-pressure steam, and their pitch. The section where the high-pressure steam is sprayed become the furrows. The ridges and furrows may be formed on the top sheet 2 side of the absorbent body 4, or they may be formed on the back sheet 3 side of the absorbent body 4.

The ridges and furrows may be formed extending in the lengthwise direction (Y-axial direction) of the sanitary napkin 1, and being alternately disposed in the widthwise direction (X-axial direction) of the sanitary napkin 1. The ridges and furrows may also extend continuously in the lengthwise direction (Y-axial direction) of the sanitary napkin 1, or they may extend intermittently, lacking some sections. For example, the ridges and furrows may extend intermittently so that the missing sections of the ridges and furrows form rectangles or zigzags in a planar view.

Also, the ridges and furrows may be formed extending in the lengthwise direction (Y-axial direction) of the sanitary napkin 1, and be alternately disposed in the widthwise direction (X-axial direction) of the sanitary napkin 1. The ridges and furrows may also extend continuously in the widthwise direction (X-axial direction) of the sanitary napkin 1, or they may extend intermittently, lacking some sections. For example, the ridges or furrows may extend intermittently so that the missing sections of the ridges or furrows form rectangles or zigzags in a planar view. When a plurality of ridges and furrows are formed on the surface of the top sheet side or the surface of the back sheet 3 side in the absorbent body 4, extending in the widthwise direction of the sanitary napkin 1 (the X-axial direction), the absorbent body 4 is resistant to slipping even when force is applied in the widthwise direction of the absorbent body 4, and the absorbent body 4 easily deforms to a curve along the shape of the wearer's body. It therefore produces less of an uncomfortable feeling for the wearer.

There are no particular restrictions on the shapes of the ridges. For example, the top sections and sides of the ridges may be curved surfaces, and the cross-sectional shapes of the ridges may be approximately inverted U-shapes along the top sheet or back sheet. The cross-sectional shapes of the ridges may be appropriately modified, and for example, they may be dome-shaped, trapezoidal, triangular or Ω-shaped quadrilaterals. The widths of the ridges preferably narrow from the bottom sections toward the top sections so that the spaces of the furrows are maintained even if force is applied to the absorbent body 4 causing the ridges to collapse.

The widths of the ridges are preferably 0.5 to 10 mm and more preferably 2 to 5 mm, from the viewpoint of fluid migration from the top sheet 2. From the same viewpoint, the widths of the furrows are preferably 0.1 to 10 mm and more preferably 1 to 5 mm.

When a plurality of ridges are formed, the widths of the ridges may be essentially equal, or they may differ. For example, a plurality of ridges may be formed in such a manner that the width of one ridge differs from the width of another ridge but is essentially equal to the width of yet another ridge. This also applies to cases where a plurality of furrows are formed.

The high-pressure steam may be sprayed over the entire mixed material, or only a portion thereof. The temperature and vapor pressure for the sprayed high-pressure steam may be varied for different sections of the mixed material. By partially spraying the high-pressure steam on the mixed material, or by altering the temperature and vapor pressure of the sprayed high-pressure steam, it is possible to vary the fiber density distribution of the absorbent body 4 at different sections of the mixed material.

The high-pressure steam may be sprayed while pressing the mixed material, or it may be sprayed without pressing. By spraying the high-pressure steam on a section of the mixed material while pressing, and spraying the high-pressure steam on the other sections without pressing, it is possible to vary the fiber density distribution of the absorbent body 4. For example, when high-pressure steam is sprayed on the mixed material while passing through mesh conveyor belts that have partial openings, the high-pressure steam directly contacts it without pressing at the open sections of the mesh conveyor belt, while the high-pressure steam is contacted while pressing at the non-open sections of the mesh conveyor belt, and therefore it is possible to vary the fiber density distribution.

Density increase by spraying of high-pressure steam is advantageous over other methods in the following aspects. When a mixed material is increased in density by press roll-molding, it must be highly compacted to impart bonding strength between the fibers and overcome repulsion between the fibers. Once compressed by high compaction, the fibers undergo elastic recovery and are restored to their original bulk. On the other hand, when a mixed material is increased in density by combining press rolling with water spraying, a basis weight of 100 $g/m^2$ or less will allow moisture to permeate to the interior of the mixed material, whereas a basis weight of greater than 100 $g/m^2$ will make it difficult for moisture to permeate to the interior of the mixed material and will not allow formation of hydrogen bonds inside the mixed material. If excess moisture is applied, the moisture will be able to permeate to the interior of the mixed material, but excessive heat and time will be required for the moisture to evaporate off, and thus productivity will be reduced. However, when the density is to be increased by spraying of high-pressure steam, water vapor permeates into the mixed material, and the hydrogen bonds (for example, the hydrogen bonds formed between water-absorbent fibers, between thermoplastic resin fibers and between water-absorbent fibers and thermoplastic resin fibers) are broken, thereby softening the mixed material. Consequently, less pressure is required to increase the density, and the softened mixed material can be more easily adjusted in density. In addition, the water vapor easily evaporates resulting in a shorter drying time, and improving productivity.

Figure 3:
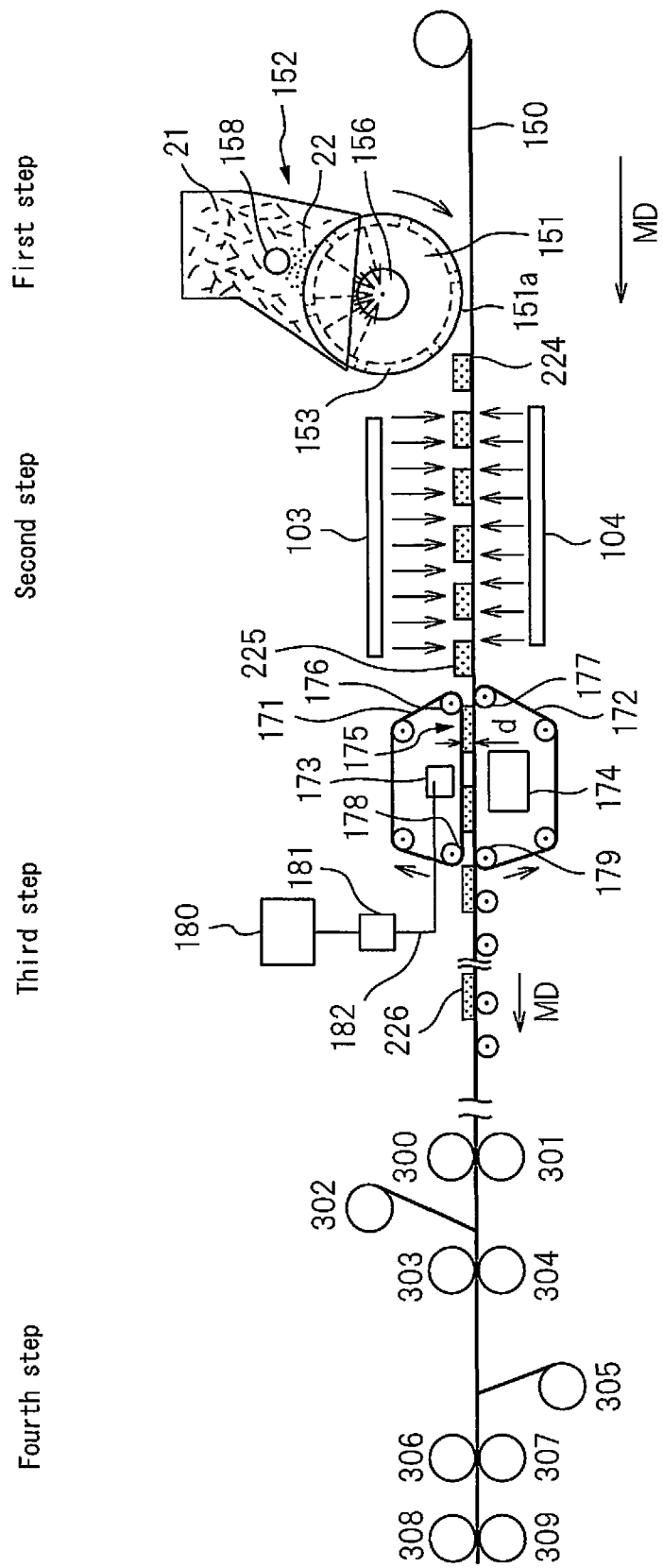
FIG. 3 is a diagram showing the production steps for a sanitary napkin according to an embodiment of the invention.

A concrete example of production steps for a sanitary napkin 1 will now be described with reference to FIG. 3.

[First Step]

Recesses 153 are formed at a prescribed pitch in the circumferential direction on the peripheral surface 151a of a suction drum 151 rotating in the machine direction MD, as a molding form in which the absorbent material is to be packed. When the suction drum 151 is rotated and the recesses 153 approach the material feeder 152, the suction section 156 acts on the recesses 153 and the absorbent material supplied from the material feeder 152 is vacuum suctioned into the recesses 153.

The hooded material feeder 152 is formed so as to cover the suction drum 151, and the material feeder 152 supplies a mixed material 21 comprising cellulose-based water-absorbent fibers and thermoplastic resin fibers into the recesses 153 by air transport. The material feeder 152 is also provided with a particle feeder 158 that supplies super-absorbent polymer particles 22, so that super-absorbent polymer particles 22 are supplied to the recesses 153. The cellulose-based water-absorbent fibers, thermoplastic resin fibers and super-absorbent polymer particles are supplied in a mixed state to the recesses 153, and an absorbent material layer 224 is formed in the recesses 153. The absorbent material layer 224 formed in the recesses 153 is transferred onto a carrier sheet 150 advancing in the machine direction MD.

[Second Step]

The absorbent material layer 224 that has been transferred onto the carrier sheet 150 separates from the peripheral surface 151a of the suction drum 151 and is transported in the machine direction MD. The uncompressed absorbent material layer 224 is arranged intermittently in the machine direction MD on the carrier sheet 150. A heating section 103 blasts air heated to 135° C. at a wind speed of 5 m/sec onto the top side of the absorbent material layer 224 while a heating section 104 blasts it onto the bottom side of the absorbent material layer 224. This melts the thermoplastic resin fibers in the absorbent material layer 224, forming an absorbent material layer 225 in which the thermoplastic resin fibers, the thermoplastic resin fibers/pulp and the thermoplastic resin fibers/super-absorbent polymer particles are bonded (heat fused). The conditions for the heated air blasted onto the absorbent material layer 224 (the temperature, wind speed and heating time) are appropriately controlled depending on the production rate.

[Third Step]

The air-permeable mesh conveyor belts 171, 172 disposed above and below, forming a pair, transport the absorbent material layer 225 on the carrier sheet 150 in the machine direction MD, while compacting it. The dimensions in the vertical direction d for the parallel traveling section 175 (the distance between the mesh conveyor belts 171, 172) are set to prescribed values by adjusting the gap between the upstream end upper roll 176 and the upstream end lower roll 177, and the gap between the downstream end upper roll 178 and the downstream end lower roll 179, which rotate in the machine direction MD, and the absorbent material layer 225 is compacted to a prescribed thickness by the mesh conveyor belts 171, 172. At the parallel traveling section 175 that extends horizontally, as shown in FIG. 3, a steam spraying section 173 and a steam suction section 174 are disposed facing and sandwiching the mesh conveyor belts 171, 172. At the steam spraying section 173, nozzles of 0.1-2 mm caliber (not shown) are disposed in the crossing direction CD (not shown) which runs perpendicular to the machine direction MD and the vertical direction TD, transversing the absorbent material layer 225 at a pitch of 0.5 to 10 mm, preferably 0.5 to 5 mm and more preferably 0.5 to 3 mm, and each nozzle has water vapor at a temperature above the boiling point of the water, generated at a steam boiler 180, which is converted to high-pressure steam adjusted to a vapor pressure of 0.1 to 2.0 MPa, for example, by a pressure control valve 181, and supplied through a tube 182. From each nozzle there is sprayed high-pressure steam through the mesh conveyor belt 171, onto an absorbent material layer 225 which is in a compacted state by the mesh conveyor belts 171, 172. The amount of high-pressure steam sprayed onto the absorbent material layer 225 is adjusted according to the running speed of the mesh conveyor belts 171, 172, and preferably when the mesh conveyor belts 171, 172 are traveling at 5-500 m/min, spraying is in a range of 1.23 kg/m$^2$ to 0.03 kg/m$^2$ on the surface area of the absorbent material layer 225 facing the mesh conveyor belt 171. The water vapor passes through the mesh conveyor belt 171, the absorbent material layer 225 and the mesh conveyor belt 172 in that order in the thickness direction of the absorbent material layer 225, and is collected by vacuum pressure suction action at the steam suction section 174. The absorbent material layer 225 on which the high-pressure steam has been sprayed advances in the machine direction MD and separates from the mesh conveyor belts 171, 172, proceeding to the fourth step. Ridges and furrows are formed on the surface of the absorbent material layer 225 on which the high-pressure steam has been sprayed. By adjusting the number of nozzles and their pitch in the steam spraying section 173, it is possible to adjust the number of ridges and furrows and their spacings. The sections where the high-pressure steam has been sprayed become the furrows.

Either or both of the mesh conveyor belts 171, 172 has a flexible property so as to easily deform in the vertical direction TD, so that the absorbent material layer 225 is not locally compacted by the mesh conveyor belts 171, 172 in the third step. The mesh conveyor belts 171, 172 used may be metal wire mesh belts formed of stainless steel alloy or bronze, or plastic mesh belts formed of polyester fiber or aramid fiber, or alternatively, metal belts formed of perforated metal plates may be used instead of mesh belts. If inclusion of metal powder in the absorbent material layer 225 is to be maximally avoided, it is preferred to use a plastic mesh belt. Also, when high heat resistance is desired for a plastic mesh belt, it is preferred to use a mesh belt made of a polyphenylene sulfide resin. A 10 to 75 mesh plain weave mesh belt using a polyphenylene sulfide resin is a particularly preferred example of a mesh belt which has flexibility and can be used for both the mesh conveyor belt 171 and the mesh conveyor belt 172. The steam spraying section 173 and the tubing 182 are preferably heat-insulated as appropriate, and are preferably also provided with a draining mechanism. This can prevent drain from the steam spraying section 173 from being sprayed from the nozzle and causing excessive moisture to be incorporated into the absorbent material layer 225. The water vapor sprayed toward the absorbent material layer 225 will be sometimes dry vapor containing no liquid moisture, sometimes saturated vapor, and sometimes wet vapor containing moisture. When the water vapor is wet vapor or saturated vapor it is easier to wet the pulp to allow shaping. Dry vapor can gasify the moisture in the pulp, and allows shaping of the pulp to be easily accomplished with the gasified moisture. If the pulp is thermoplastic synthetic fiber, the heat of the dry vapor can facilitate shaping of the thermoplastic synthetic fibers. The steam spraying section 173 has a heating mechanism provided in it, and it can convert the water vapor to superheated steam and spray it. The steam suction section 174 preferably has tubing that directs toward an exhaust blower (not shown) after the aspirated high-pressure steam has passed through a steam separator. Incidentally, the positioning of the steam spraying section 173 and the steam suction section 174 may be switched, i.e. the steam spraying section 173 may be below and the steam suction section 174 above. When the high-pressure steam does not need to be recovered, the process may be carried out without provision of the steam suction 174 section.

When it is not necessary to increase the density by spraying with high-pressure steam, the third step may be omitted.

[Fourth Step]

The fourth step is an example of a common step for producing a sanitary napkin. A pair of rolls 300, 301 cut out the absorbent material layer 226 obtained by the third step into a prescribed shape (or when the third step is omitted, the absorbent material layer 225 obtained in the second step), to form an absorbent body. A top sheet is supplied from a roll 302 and sealed with hot embossers 303, 304 having high compression section and a low compression section, and the top sheet and absorbent body are integrated. Next, a back sheet is supplied from the roll 305, and with the absorbent body sandwiched between the top sheet and the back sheet, the product perimeter is subjected to hot embossing for sealing and passed to steps 306 and 307, and finally cut into the product shape by steps 308 and 309.

Preferably a blood slipping agent having a 40° C. kinematic viscosity of 0.01 to 80 mm$^2$/s, a water holding percentage of 0.01 to 4.0 mass % and a weight-average molecular weight of less than 1,000 is coated onto at least the excretory opening contact region 20 on the skin contact surface of the top sheet 2. The blood slipping agent will be described in detail in a separate section.

The blood slipping agent may also be coated onto regions other than the excretory opening contact region 20 on the skin contact surface of the top sheet 2 (for example, the perimeter region of the excretory opening contact region 20). For example, the blood slipping agent may be coated essentially over the entire skin contact surface or essentially over the entire absorbent body placement region. The absorbent body placement region is the region in which the absorbent body 4 overlaps the top sheet 2 when the absorbent body 4 has been projected onto the top sheet 2. The excretory opening contact region 20 is set as a virtual region at essentially the center of the absorbent body placement region, but it may instead be set as a visually recognizable region. Visual recognition may be produced, for example, by coloration of the excretory opening contact region 20, or by formation of recesses in a continuous or intermittent fashion along the periphery of the excretory opening contact region 20 (for example, recesses formed by heat embossing treatment).

If the blood slipping agent is coated on the excretory opening contact region 20, the following function and effect will be exhibited. Menstrual blood excreted by the wearer and reaching the excretory opening contact region 20 contacts the blood slipping agent present in the excretory opening contact region 20, passing through the top sheet 2 and migrating into the absorbent body 4. Therefore, the sanitary napkin 1 has improved migration of menstrual blood from the top sheet 2 to the absorbent body 4, and can reduce residue of menstrual blood in the top sheet 2. This prevents the skin contact surface of the top sheet 2 from having a sticky feel, and maintains a smooth feel. This function and effect of the blood slipping agent is exhibited regardless of changes in menstrual blood discharge during menstruation (that is, whether the amount of discharged menstrual blood is large or small). Incidentally, since the blood slipping agent functions as a lubricating agent to reduce friction between fibers, it can improve the flexibility of the top sheet 2 as a whole.

A blood slipping agent, while exhibiting the function and effect described above, can potentially weaken the adhesive force of the adhesive when it mixes with the adhesive bonding the top sheet 2 and the absorbent body 4. In this regard, with the sanitary napkin 1, it is possible to maintain bonding between the top sheet 2 and the absorbent body 4 by the compressed sections 5 even when the adhesive force of the adhesive has been weakened by the blood slipping agent.

The sanitary napkin 1 does not require components, such as emollients and immobilizing agents, unlike in known absorbent articles containing skin care compositions, lotion compositions and the like, and the blood slipping agent alone may be applied to the top sheet 2.

The basis weight of the blood slipping agent may usually be about 1 to 30 g/m$^2$, preferably about 2 to 20 g/m$^2$ and even more preferably about 3 to 10 g/m$^2$. If the basis weight of the blood slipping agent is lower than about 1 g/m$^2$, menstrual blood will tend to remain in the top sheet 2, while if the basis weight of the blood slipping agent is greater than about 30 g/m$^2$, there will tend to be an increase in the sticky feel during wear.

The basis weight of the blood slipping agent can be measured by the following method, for example.

(1) The region of the top sheet that is to be measured is cut out using a sharp blade, such as a cutter replacement blade, while minimizing any alteration in thickness, to obtain a sample.

(2) The area of the sample: SA (m$^2$) and the mass: $SM_0$ (g) are measured.

(3) The sample is stirred for at least 3 minutes in a solvent that can dissolve the blood slipping agent, such as ethanol or acetone, to dissolve the blood slipping agent in the solvent.

(4) The sample is filtered on mass-measured filter paper, and the sample is thoroughly rinsed with the solvent on the filter paper. The sample on the filter paper is dried in an oven at 60° C.

(5) The masses of the filter paper and sample are measured, and the mass of the filter paper is subtracted to calculate the dry sample mass: $SM_{41}$ (g).

(6) The basis weight BBS (g/m$^2$) of the blood slipping agent is calculated by the following formula.

$$BBS(g/m^2)=[SM_0(g)-SM_1(g)]/SA(m^2)$$

In order to minimize error, multiple samples are taken from multiple absorbent articles, without the total area of the sample exceeding 100 cm$^2$, conducting several repeated measurements and taking the average value.

The blood slipping agent is preferably coated without obstructing the voids between the fibers of the top sheet 2. For example, the blood slipping agent may be adhering as droplets or particulates on the surfaces of the fibers of the top sheet 2, or covering the surfaces of the fibers.

The blood slipping agent is preferably coated so that the surface area is increased. This will increase the contact area between the blood slipping agent and the menstrual blood and facilitate slipping of the blood slipping agent together with the menstrual blood. When the blood slipping agent is present as droplets or particulates, the particle diameters can be reduced to increase the surface area.

Examples of methods for coating the blood slipping agent include methods that employ coating applicators (for example, non-contact coaters, such as spiral coaters, curtain coaters, spray coaters and dip coaters. and contact coaters). Non-contact coaters are preferred coating applicators. This will allow the droplets or particulate blood slipping agent to evenly disperse over the entirety, while reducing damage to the top sheet 2.

The blood slipping agent may, if desired, be applied as a coating solution containing a volatile solvent, such as an alcohol-based solvent, ester-based solvent or aromatic solvent. If the coating solution includes a volatile solvent, the viscosity of the coating solution containing the blood slipping agent will be lowered, thereby allowing the application steps to be simplified, facilitating application and making heating during application unnecessary.

The blood slipping agent may be coated directly, if it is a liquid at room temperature, or it may be heated to lower the viscosity, and when it is a solid at room temperature, it may be heated to liquefaction and coated with a control seam HMA (Hot Melt Adhesive) gun. By increasing the air pressure of the control seam HMA gun, it is possible to coat the blood slipping agent as fine particulates. The coating amount of the blood slipping agent can be adjusted, for example, by adjusting the discharged amount from a control seam HMA gun.

The blood slipping agent may be coated during production of the top sheet 2, or it may be coated in the manufacturing line for the sanitary napkin 1. From the viewpoint of minimizing equipment investment, the blood slipping agent is preferably coated in the manufacturing line for the sanitary napkin 1, and in order to prevent shedding of the blood slipping agent which may contaminate the line, the blood slipping agent or its composition is preferably coated during a step downstream from the manufacturing line, and specifically, immediately before encapsulation of the product in an individual package.

<Blood Slipping Agent>

The blood slipping agent has a kinematic viscosity of about 0.01 to about 80 mm$^2$/s at 40° C., a water holding percentage of about 0.05 to about 4.0 mass %, and a weight-average molecular weight of less than about 1,000.

The 40° C. kinematic viscosity of the blood slipping agent may be appropriately adjusted in the range of about 0 to about 80 mm$^2$/s, but it is preferably about 1 to about 70 mm$^2$/s, more preferably about 3 to about 60 mm$^2$/s, even more preferably about 5 to about 50 mm$^2$/s and yet more preferably about 7 to about 45 mm$^2$/s. As used herein, the "40° C. kinematic viscosity" may be referred to simply as "kinematic viscosity".

The kinematic viscosity tends to be higher with a) a larger molecular weight of the blood slipping agent, b) a higher percentage of polar groups, such as carbonyl bonds (—CO—), ether bonds (—O—), carboxyl groups (—COOH) and hydroxyl groups (—OH), and c) a larger IOB.

In order to have a kinematic viscosity of about 0 to about 80 mm$^2$/s at 40° C., the melting point of the blood slipping agent is preferably 45° C. or less. This is because the kinematic viscosity will tend to be higher if the blood slipping agent contains crystals at 40° C.

The significance of the kinematic viscosity of the blood slipping agent will be explained below, but a kinematic viscosity exceeding about 80 mm$^2$/s will tend to result in high viscosity of the blood slipping agent, such that it will not as easily slip down from the projections to the recesses together with menstrual blood that has reached the skin contact surface of the top sheet, and subsequently migrate into the absorbent body.

The kinematic viscosity can be measured according to JIS K 2283:2000, "5. Kinematic Viscosity Test Method", using a Cannon-Fenske reverse-flow viscometer, at a testing temperature of 40° C.

The water holding percentage of the blood slipping agent may be appropriately adjusted in the range of about 0.01 to about 4.0 mass %, but it is preferably about 0.02 to about 3.5 mass %, more preferably about 0.03 to about 3.0 mass %, even more preferably about 0.04 to about 2.5 mass % and yet more preferably about 0.05 to about 2.0 mass %.

As used herein, "water holding percentage" means the percentage (mass) of water that can be held by a substance, and it may be measured in the following manner.

(1) A 20 mL test tube, a rubber stopper, the substance to be measured and deionized water are allowed to stand for a day and a night in a thermostatic chamber at 40° C.

(2) Into the test tube in the thermostatic chamber there are charged 5.0 g of the substance to be measured and 5.0 g of deionized water.

(3) The mouth of the test tube is closed with the rubber stopper in the thermostatic chamber, and the test tube is rotated once and allowed to stand for 5 minutes.

(4) A 3.0 g portion of the layer of the substance to be measured (usually the upper layer) is sampled into a glass dish with a diameter of 90 mm and a mass of $W_0$ (g), in the thermostatic chamber.

(5) The dish is heated at 105° C. for 3 hours in an oven to evaporate off the moisture, and the mass $W_1$ (g) of each dish is measured.

(6) The water holding percentage is calculated by the following formula.

$$\text{Water holding percentage (mass \%)} = 100 \times [W_0(g) - W_1(g)]/3.0(g)$$

The measurement is conducted three times, and the average value is recorded.

The significance of the water holding percentage of the blood slipping agent will be explained below, but basically a low water holding percentage will tend to lower the affinity between the blood slipping agent and menstrual blood, thus impeding its migration into the absorbent body together with menstrual blood that has reached the skin contact surface of the top sheet. If the water holding percentage is high, on the other hand, the affinity between menstrual blood and the blood modifying agent will become very high, similar to a surfactant, and absorbed menstrual blood will tend to remain on the skin contact surface of the top sheet, resulting in more red coloration of the skin contact surface of the top sheet.

The water holding percentage tends to be a larger value with a) a smaller molecular weight of the blood slipping agent, and b) a higher percentage of polar groups, such as carbonyl bonds (—CO—), ether bonds (—O—), carboxyl groups (—COOH) and hydroxyl groups (—OH). This is because the blood slipping agent has greater hydrophilicity. The water holding percentage will tend to have a larger value with a greater IOB, i.e. with a higher inorganic value or with a lower organic value. This is also because the blood slipping agent has greater hydrophilicity.

The significance of the kinematic viscosity and water holding percentage of the blood slipping agent will now be explained.

Menstrual blood excreted by the wearer and reaching the excretory opening contact region contacts the blood slipping agent in the projections and slips down together with it into the recesses, passing through the top sheet and migrating into the absorbent body.

More specifically, since the blood slipping agent with a kinematic viscosity of about 0.01 to about 80 mm$^2$/s at 40° C. has very low viscosity near the body temperature of the wearer and has a constant affinity with the menstrual blood, it slips down from the projections to the recesses together with the menstrual blood, and utilizing the energy during sliding, the menstrual blood is able to pass through the recesses of the top sheet to rapidly migrate into the absorbent body. Also, since the blood slipping agent present in the projections has a water holding percentage of about 0.01 to about 4.0 mass %, presumably it has no affinity with the hydrophilic component (blood plasma, etc.) in the menstrual blood, and therefore the menstrual blood does not easily remain on the top sheet.

When the menstrual blood discharged by the wearer is a large amount of menstrual blood, the menstrual blood easily migrates into the absorbent body, even when the kinetic energy of the menstrual blood itself is high and the kinematic viscosity of the blood slipping agent is relatively high so that it does not easily slip down together with the menstrual blood, or when the water holding percentage value is relatively high so that affinity with the hydrophilic components of the menstrual blood is high, or when the weight-average molecular weight value is relatively high so that it does not easily slip down together with the menstrual blood, or when the skin contact surface of the top sheet does not have an irregular structure.

When the menstrual blood discharge by the wearer is a small amount of menstrual blood, on the other hand, the kinetic energy of the menstrual blood is low, and menstrual blood that has reached the skin contact surface of the top sheet tends to easily pool in such cases. Consequently, the blood slipping agent slips down from the heights into the recesses together with the menstrual blood, and the menstrual blood is drawn into the top sheet and then drawn into the absorbent body, so that the menstrual blood can rapidly migrate into the absorbent body.

The blood slipping agent has a weight-average molecular weight of less than about 1,000, and preferably a weight-average molecular weight of less than about 900. This is because if the weight-average molecular weight is about 1,000 or higher, tack may be produced in the blood slipping agent itself, tending to create a feeling of discomfort for the wearer. If the weight-average molecular weight increases, the viscosity of the blood slipping agent will tend to increase, and it will therefore be difficult to lower the viscosity of the blood slipping agent by heating to a viscosity suitable for coating, and as a result, the blood slipping agent may need to be diluted with a solvent.

The blood slipping agent preferably has a weight-average molecular weight of about 100 or greater, and more preferably it has a weight-average molecular weight of about 200 or greater. This is because if the weight-average molecular weight is low, the vapor pressure of the blood slipping agent may be increased, gasification may occur during storage and the amount may be reduced, often leading to problems, such as odor during wear.

As used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 . . . ), it refers to $M_w$ determined by the following formula.

$$M_w = \Sigma N_i M_i^2 / \Sigma N_i M_i$$

The weight-average molecular weights used throughout the present specification are the values measured by gel permeation chromatography (GPC), based on polystyrene.

The GPC measuring conditions may be the following, for example.

Device: Lachrom Elite high-speed liquid chromatogram by Hitachi High-Technologies Corp.
Columns: SHODEX KF-801, KF-803 and KF-804, by Showa Denko K.K.
Eluent: THF
Flow rate: 1.0 mL/min
Driving volume: 100 μL
Detection: RI (differential refractometer)

The weight-average molecular weights listed in the examples of the present specification were measured under the conditions described below.

The blood slipping agent may have an IOB of about 0.00 to about 0.60.

The IOB (Inorganic Organic Balance) is an indicator of the hydrophilic-lipophilic balance, and as used herein, it is the value calculated by the following formula by Oda et al.:

IOB=Inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| CH$_2$ | 0 | 20 |
| iso branching | 0 | −10 |
| tert branching | 0 | −20 |
| Light metal (salts) | ≥500 | 0 |

For example, in the case of an ester of tetradecanoic acid which has 14 carbon atoms and dodecyl alcohol which has 12 carbon atoms, the organic value is 520 (CH$_2$, 20×26) and the inorganic value is 60 (—COOR, 60×1), and therefore IOB=0.12.

The IOB of the blood slipping agent is preferably between about 0.00 and 0.60, more preferably between about 0.00 and 0.50, even more preferably between about 0.00 and 0.40 and most preferably between about 0.00 and 0.30. If the IOB is within this range, it will be easier to meet the aforementioned conditions for the water-holding capacity and kinematic viscosity.

The blood slipping agent preferably has a melting point of 45° C. or less, and more preferably it has a melting point of 40° C. or less. If the blood slipping agent has a melting point of 45° C. or less, the blood slipping agent will more easily exhibit a kinematic viscosity in the aforementioned range.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood slipping agent has a melting point of about 45° C. or less, it may be either liquid or solid at room temperature (about 25° C.), or in other words, the melting point may be either about 25° C. or higher or below about 25° C., and for example, it may have a melting point of about −5° C. or about −20° C.

The blood slipping agent does not have a lower limit for its melting point, but its vapor pressure is preferably low. The vapor pressure of the blood slipping agent is preferably between about 0 and about 200 Pa, more preferably between about 0 and about 100 Pa, more preferably between about 0 and about 10 Pa, even more preferably between about 0 and about 1 Pa and yet more preferably between about 0.0 and about 0.1 Pa, at 25° C. (1 atmosphere).

Considering that the absorbent article of the present disclosure is to be used in contact with the human body, the vapor pressure is preferably between about 0 and about 700 Pa, more preferably between about 0 and about 100 Pa, more preferably between about 0 and about 10 Pa, even more preferably between about 0 and about 1 Pa and yet more preferably between about 0.0 and about 0.1 Pa, at 40° C. (1 atmosphere). If the vapor pressure of the blood slipping agent is high, gasification may occur during storage and the amount may be reduced, often creating problems, such as odor during wear.

The melting point of the blood slipping agent may be selected depending on the weather or duration of wear. For example, in regions with a mean atmospheric temperature of about 10° C. or less, using a blood slipping agent with a melting point of about 10° C. or less may help the blood slipping agent function after excretion of menstrual blood, even if it has been cooled by the ambient temperature.

Also, when the absorbent article is to be used for a prolonged period of time, the melting point of the blood slipping agent is preferably at the high end of the range of about 45° C. or less. This is so that the blood slipping agent will not be easily affected by sweat or friction during wearing, and will not easily become biased even during prolonged wearing.

In the technical field, the skin contact surfaces of top sheets are coated with surfactants in order to alter the surface tension of menstrual blood and promote rapid absorption of menstrual blood. However, the top sheet coated with the surfactant has very high affinity for the hydrophilic components (blood plasma, etc.) in menstrual blood, and acts to attract them, tending to cause menstrual blood instead to remain on the top sheet. The blood slipping agent, unlike conventionally known surfactants, has low affinity with menstrual blood and therefore does not cause residue of menstrual blood on the top sheet and allows rapid migration into the absorbent body.

The blood slipping agent is preferably selected from the group consisting of following items (i) to (iii), and any combination thereof:

(i) a hydrocarbon;

(ii) a compound having (ii-1) a hydrocarbon moiety and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—), inserted between a C—C single bond of the hydrocarbon moiety, and (iii-3) one or more, same or different groups selected from the group consisting of carboxyl group (—COOH) and hydroxyl group (—OH), substituting a hydrogen on the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as "alkane"), an olefin-based hydrocarbon (containing one double bond, also referred to as "alkene"), an acetylene-based hydrocarbon (containing one triple bond, also referred to as "alkyne"), or a hydrocarbon or cyclic hydrocarbon comprising two or more bonds selected from the group consisting of double bonds or triple bonds, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include straight-chain hydrocarbons and branched-chain hydrocarbons.

When two or more oxy groups (—O—) are inserted in the compounds of (ii) and (iii) above, the oxy groups (—O—) are not adjacent. Thus, compounds (ii) and (iii) do not include compounds with continuous oxy groups (i.e. peroxides).

In the compounds of (iii), compounds in which at least one hydrogen on the hydrocarbon moiety is substituted with a hydroxyl group (—OH) are preferred over compounds in which at least one hydrogen on the hydrocarbon moiety is substituted with a carboxyl group (—COOH). This is because the carboxyl groups bond with metals and the like in menstrual blood, increasing the water holding percentage of the blood slipping agent, which may sometimes exceed the prescribed range. The same is true from the viewpoint of the IOB as well. As shown in Table 1, the carboxyl groups bond with metals and the like in menstrual blood, drastically increasing the inorganic value from 150 to 400 or greater, and therefore a blood slipping agent with carboxyl groups can increase the IOB value to more than about 0.60 during use.

The blood slipping agent is more preferably selected from the group consisting of following items (i') to (iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety.

When 2 or more identical or different bonds are inserted in a compound of (ii') or (iii'), that is, when 2 or more identical or different bonds selected from among carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood slipping agent more preferably has no more than about 1.8 carbonyl bonds (—CO—), no more than two ester bonds (—COO—), no more than about 1.5 carbonate bonds (—OCOO—), no more than about 6 ether bonds (—O—), no more than about 0.8 carboxyl groups (—COOH) and/or no more than about 1.2 hydroxyl groups (—OH), per 10 carbon atoms in the hydrocarbon moiety.

The blood slipping agent is even more preferably selected from the group consisting of following items (A) to (F), as well as any combination thereof:

(A) an ester of (A1) a compound having a chain hydrocarbon moiety and 2-4 hydroxyl groups substituting hydrogens on the chain hydrocarbon moiety, and (A2) a compound having a chain hydrocarbon moiety and one carboxyl group substituting a hydrogen on the chain hydrocarbon moiety;

(B) an ether of (B1) a compound having a chain hydrocarbon moiety and 2-4 hydroxyl groups substituting hydrogens on the chain hydrocarbon moiety, and (B2) a compound having a chain hydrocarbon moiety and one hydroxyl group substituting a hydrogen on the chain hydrocarbon moiety;

(C) an ester of (C1) a carboxylic acid, hydroxy acid, alkoxy acid or oxoacid containing a chain hydrocarbon moiety and 2-4 carboxyl groups substituting hydrogens on the chain hydrocarbon moiety, and (C2) a compound having a chain hydrocarbon moiety and one hydroxyl group substituting a hydrogen on the chain hydrocarbon moiety;

(D) a compound having a chain hydrocarbon moiety, and one bond selected from the group consisting of ether bond (—O—), carbonyl bond (—CO—), ester bond (—COO—) and carbonate bond (—OCOO—), inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

The blood slipping agent according to (A) to (F) will now be explained in detail.

[(A) Ester of (A1) a Compound Having a Chain Hydrocarbon Moiety and 2-4 Hydroxyl Groups Substituting for Hydrogens on the Chain Hydrocarbon Moiety, and (A2) a Compound Having a Chain Hydrocarbon Moiety and 1 Carboxyl Group Substituting for a Hydrogen on the Chain Hydrocarbon Moiety]

In the (A) ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety (hereunder also referred to as "compound (A)"), it is not necessary for all of the hydroxyl groups to be esterified so long as the kinematic viscosity, water holding percentage and weight-average molecular weight are within the aforementioned ranges.

Examples for the (A1) compound having a chain hydrocarbon moiety and 2-4 hydroxyl groups substituting at hydrogens of the chain hydrocarbon moiety (hereunder also referred to as "compound (A1)") include chain hydrocarbon tetraols, such as alkanetetraols including pentaerythritol, chain hydrocarbon triols, such as alkanetriols including glycerin, and chain hydrocarbon diols, such as alkanediols including glycols.

Compounds for the (A2) compound having a chain hydrocarbon moiety and one carboxyl group substituting at a hydrogen of the chain hydrocarbon moiety include compounds in which one hydrogen on the hydrocarbon is substituted with one carboxyl group (—COOH), such as fatty acids.

Examples for compound (A) include ($a_1$) an ester of a chain hydrocarbon tetraol and at least one fatty acid, ($a_2$) an ester of a chain hydrocarbon triol and at least one fatty acid, and (a₃) an ester of a chain hydrocarbon diol and at least one fatty acids.

[(a₁) Esters of a Chain Hydrocarbon Tetraol and at Least One Fatty Acid]

Examples of esters of a chain hydrocarbon tetraol and at least one fatty acid include tetraesters of pentaerythritols and fatty acids, represented by the following formula (1):

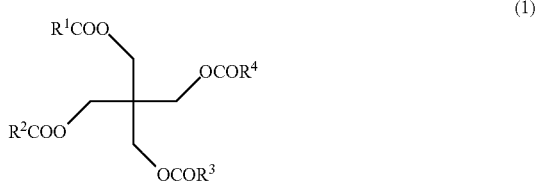

(1)

triesters of pentaerythritol and fatty acids, represented by the following formula (2):

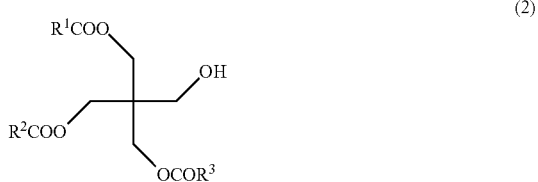

(2)

diesters of pentaerythritol and fatty acids, represented by the following formula (3):

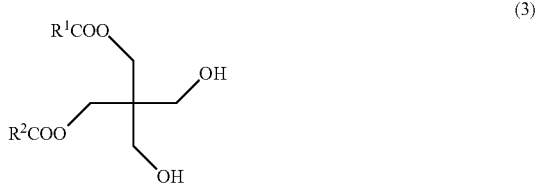

(3)

and monoesters of pentaerythritol and fatty acids, represented by the following formula (4).

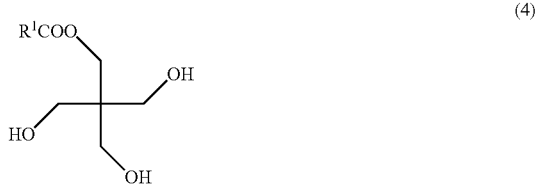

(4)

In the formulas, $R^1$ to $R^4$ each represent a chain hydrocarbon.

The fatty acids composing the esters of pentaerythritol and fatty acids ($R^1COOH$, $R^2COOH$, $R^3COOH$, and $R^4COOH$) are not particularly restricted so long as the pentaerythritol and fatty acid esters satisfy the conditions for the kinematic viscosity, water holding percentage and weight-average molecular weight, and for example, there may be mentioned saturated fatty acids, such as a $C_2$-$C_{30}$ saturated fatty acids, including acetic acid ($C_2$) ($C_2$ representing the number of carbons, corresponding to the number of carbons of $R^1C$, $R^2C$, $R^3C$ or $R^4C$, same hereunder), propanoic acid ($C_3$), butanoic acid ($C_4$) and its isomers, such as 2-methylpropanoic acid ($C_4$), pentanoic acid ($C_5$) and its isomers, such as 2-methylbutanoic acid ($C_5$) and 2,2-dimethylpropanoic acid ($C_5$), hexanoic acid ($C_6$), heptanoic acid ($C_7$), octanoic acid ($C_8$) and its isomers, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$) and triacontanoic acid ($C_{30}$), as well as isomers of the foregoing that have not been mentioned.

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), as well as partial hydrogen adducts of the foregoing.

Considering the potential for degradation by oxidation and the like, the ester of pentaerythritol and a fatty acid is preferably an ester of pentaerythritol and a fatty acid derived from a saturated fatty acid, or in other words, an ester of pentaerythritol and a saturated fatty acid.

Also, in order to lower the water holding percentage value, the ester of pentaerythritol and a fatty acid is preferably a diester, triester or tetraester, more preferably a triester or tetraester, and most preferably a tetraester.

From the viewpoint of the IOB being from about 0.00 to about 0.60, for a tetraester of pentaerythritol and a fatty acid, the total number of carbons of the fatty acid composing the tetraester of the pentaerythritol and fatty acid, i.e. the total number of carbons of the $R^1C$, $R^2C$, $R^3C$ and $R^4C$ portions in formula (1), is preferably about 15 (the IOB is 0.60 when the total number of carbon atoms is 15).

Examples of tetraesters of pentaerythritol and fatty acids include tetraesters of pentaerythritol with hexanoic acid ($C_6$), heptanoic acid ($C_7$), octanoic acid ($C_8$), such as 2-ethylhexanoic acid ($C_8$), nonanoic acid ($C_9$), decanoic acid ($C_{10}$) and/or dodecanoic acid ($C_{12}$).

From the viewpoint of the IOB being from about 0.00 to about 0.60, in a triester of pentaerythritol and a fatty acid, the total number of carbons of the fatty acid composing the triester of the pentaerythritol and fatty acid, i.e. the total number of carbons of the $R^1C$, $R^2C$ and $R^3C$ portions in formula (2), is preferably about 19 or greater (the IOB is 0.58 when the number of carbon atoms is 19).

From the viewpoint of the IOB being from about 0.00 to about 0.60, in a diester of pentaerythritol and a fatty acid, the total number of carbons of the fatty acid composing the diester of the pentaerythritol and fatty acid, i.e. the total number of carbons of the $R^1C$ and $R^2C$ portion in formula (3), is preferably about 22 or greater (the IOB is 0.59 when the number of carbon atoms is 22).

From the viewpoint of the IOB being from about 0.00 to about 0.60, in a monoester of pentaerythritol and a fatty acid, the total number of carbons of the fatty acid composing the monoester of the pentaerythritol and fatty acid, i.e. the number of carbons of the $R^1C$ portion in formula (4), is preferably about 25 or greater (the IOB is 0.60 when the number of carbon atoms is 25).

The effects of double bonds, triple bonds, iso-branches and tert-branches are not considered in this calculation of the IOB (same hereunder).

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

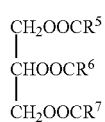

(5)

diesters of glycerin and fatty acids, represented by the following formula (6):

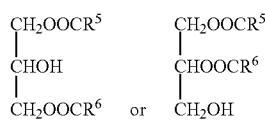

(6)

and monoesters of glycerin and fatty acids, represented by the following formula (7):

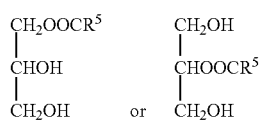

(7)

wherein $R^5$-$R^7$ each represent a chain hydrocarbon.

The fatty acid composing the ester of glycerin and a fatty acid ($R^5COOH$, $R^6COOH$ and $R^7COOH$) is not particularly restricted so long as the ester of glycerin and a fatty acid satisfies the conditions for the kinematic viscosity, water holding percentage and weight-average molecular weight, and for example, there may be mentioned the fatty acids mentioned for the "($a_1$) Ester of chain hydrocarbon tetraol and at least one fatty acid", namely saturated fatty acids and unsaturated fatty acids, and in consideration of the potential for degradation by oxidation and the like, the ester is preferably a glycerin and fatty acid ester derived from a saturated fatty acid, or in other words, an ester of glycerin and a saturated fatty acid.

Also, from the viewpoint of lowering the water holding percentage value, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

Considered from the viewpoint of obtaining a melting point of about 45° C. or less, the triester of glycerin and a fatty acid preferably has a total number of carbon atoms in the fatty acid composing the triester of glycerin and a fatty acid, i.e. a total number of carbons in the $R^5C$, $R^6C$ and $R^7C$ portions in formula (5), of about 40 or less.

From the viewpoint of the IOB being from about 0.00 to about 0.60, in a triester of glycerin and a fatty acid, the total number of carbons of the fatty acid composing the triester of the glycerin and fatty acid, i.e. the total number of carbons of the $R^5C$, $R^6C$ and $R^7C$ portions in formula (5), is preferably about 12 or greater (the IOB is 0.60 when the total number of carbon atoms is 12).

Triesters of glycerin and fatty acids, being aliphatic and therefore potential constituent components of the human body, are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 different fatty acids, and mixtures of the foregoing.

From the viewpoint of the IOB being from about 0.00 to about 0.60, in a diester of glycerin and a fatty acid, the total number of carbons of the fatty acid composing the diester of the glycerin and fatty acid, i.e. the total number of carbons of the $R^5C$ and $R^6C$ portions in formula (6), is preferably about 16 or greater (the IOB is 0.58 when the total number of carbon atoms is 16).

Monoesters of glycerin and fatty acids are also known as monoglycerides, and examples include glycerin and octadecanoic acid ($C_{18}$) monoester, and glycerin and docosanoic acid ($C_{22}$) monoester.

From the viewpoint of the IOB being from about 0.00 to about 0.60, in a monoester of glycerin and a fatty acid, the total number of carbons of the fatty acid composing the monoester of the glycerin and fatty acid, i.e. the number of carbons of the $R^5C$ portion in formula (7), is preferably about 19 or greater (the IOB is 0.59 when the number of carbon atoms is 19).

[($a_3$) Ester of a Chain Hydrocarbon Diol and at Least One Fatty Acid]

Examples of esters of a chain hydrocarbon diol and at least one fatty acid include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of esters of a chain hydrocarbon diol and at least one fatty acid include diesters of $C_2$-$C_6$ glycols and fatty acids, represented by the following formula (8):

wherein k represents an integer of 2 to 6, and $R^8$ and $R^9$ each represent a chain hydrocarbon,
and monoesters of $C_2$-$C_6$ glycols and fatty acids, represented by the following formula (9):

wherein k represents an integer of 2 to 6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the kinematic viscosity, water holding percentage and weight-average molecular weight, and for example, there may be mentioned the fatty acids mentioned above for the "($a_1$) Ester of chain hydrocarbon tetraol and at least one fatty acid", namely saturated fatty acids and unsaturated fatty acids, and in consideration of the potential for degradation by oxidation and the like, it is preferably a saturated fatty acid.

From the viewpoint of the IOB being from about 0.00 to about 0.60, in a diester of butylene glycol represented by formula (8) (k=4) and a fatty acid, the total number of carbons of the $R^8C$ and $R^9C$ portions is preferably about 6 or greater (the IOB is 0.60 when the total number of carbon atoms is 6).

From the viewpoint of the IOB being from about 0.00 to about 0.60, in a monoester of ethylene glycol represented by formula (9) (k=2) and a fatty acid, the number of carbons of the $R^8C$ portion is preferably about 12 or greater (the IOB is 0.57 when the number of carbon atoms is 12).

Considering the potential for degradation by oxidation and the like, the ester of the $C_2$-$C_6$ glycol and fatty acid is preferably a $C_2$-$C_6$ glycol and fatty acid ester derived from a saturated fatty acid, or in other words, an ester of a $C_2$-$C_6$ glycol and a saturated fatty acid.

Also, from the viewpoint of lowering the water holding percentage value, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, from the viewpoint of lowering the water holding percentage value, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a Compound Having a Chain Hydrocarbon Moiety and 2-4 Hydroxyl Groups Substituting for Hydrogens on the Chain Hydrocarbon Moiety and (B2) a Compound Having a Chain Hydrocarbon Moiety and 1 Hydroxyl Group Substituting for a Hydrogen on the Chain Hydrocarbon Moiety]

In the (B) ether of (B1) a compound having a chain hydrocarbon moiety and 2-4 hydroxyl groups substituting for hydrogens on the chain hydrocarbon moiety and (B2) a compound having a chain hydrocarbon moiety and 1 hydroxyl group substituting for a hydrogen on the chain hydrocarbon moiety (hereunder also referred to as "compound (B)"), it is not necessary for all of the hydroxyl groups to be etherified so long as the kinematic viscosity, water holding percentage and weight-average molecular weight are within the aforementioned ranges.

The (B1) compound having a chain hydrocarbon moiety and 2-4 hydroxyl groups substituting at hydrogens of the chain hydrocarbon moiety (hereunder also referred to as "compound (B1)"), may be pentaerythritol, glycerin or glycol, for example, mentioned as compound (A1) for "compound (A)".

The (B2) compound having a chain hydrocarbon moiety and one hydroxyl group substituting at a hydrogen of the chain hydrocarbon moiety (hereunder also referred to as "compound (B2)") may be, for example, a compound in which one hydrogen of the hydrocarbon is substituted with one hydroxyl group (—OH), such as an aliphatic monohydric alcohol, which may be a saturated aliphatic monohydric alcohol or an unsaturated aliphatic monohydric alcohol.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and its isomers, including isopropyl alcohol ($C_3$), butyl alcohol ($C_4$) and its isomers, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and its isomers, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein one C—C single bond of a saturated aliphatic monohydric alcohol mentioned above is replaced with a C=C double bond, such as oleyl alcohol, and for example, such alcohols are commercially available by New Japan Chemical Co., Ltd. as the RIKACOL Series and UNJECOL Series.

Examples for compound (B) include ($b_1$) ethers of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, ($b_2$) ethers of a chain hydrocarbon triol and at least one aliphatic monohydric alcohol, such as monoethers, diethers and triethers, preferably diethers and triethers and more preferably triethers, and ($b_3$) ethers of a chain hydrocarbon diol and at least one aliphatic monohydric alcohol, such as monoethers and diethers, and preferably diethers.

Examples of ethers of a chain hydrocarbon tetraol and at least one aliphatic monohydric alcohol include tetraethers, triethers, diethers and monoethers of pentaerythritol and aliphatic monohydric alcohols, represented by the following formulas (10) to (13):

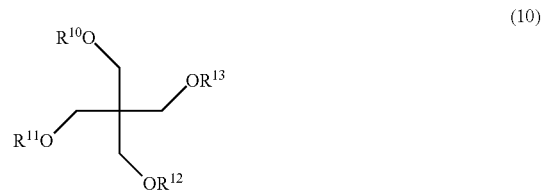

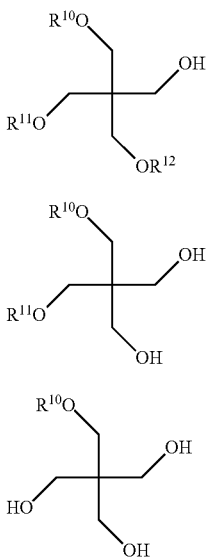

wherein $R^{10}$-$R^{13}$ each represent a chain hydrocarbon.

Examples of ethers of a chain hydrocarbon triol and at least one aliphatic monohydric alcohol include triethers, diethers and monoethers of glycerin and aliphatic monohydric alcohols, represented by the following formulas (14) to (16):

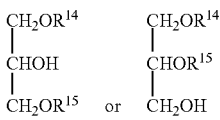

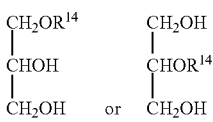

wherein $R^{14}$-$R^{16}$ each represent a chain hydrocarbon.

Ethers of a chain hydrocarbon diol and at least one aliphatic monohydric alcohol include diethers of $C_2$-$C_6$ glycols and aliphatic monohydric alcohols, represented by the following formula (17):

 (17)

wherein n is an integer of 2 to 6, and $R^{17}$ and $R^{18}$ are each a chain hydrocarbon, and monoethers of $C_2$-$C_6$ glycols and aliphatic monohydric alcohols, represented by the following formula (18):

 (18)

wherein n is an integer of 2 to 6, and $R^{17}$ is a chain hydrocarbon.

From the viewpoint of the IOB being between about 0.00 and about 0.60, in a tetraether of pentaerythritol and an aliphatic monohydric alcohol, the total number of carbon atoms of the aliphatic monohydric alcohol composing the tetraether of pentaerythritol and the aliphatic monohydric alcohol, i.e. the total number of carbon atoms of the $R^{10}$, $R^{11}$, $R^{12}$ and $R^{13}$ portions in formula (10), is preferably about 4 or greater (the IOB is 0.44 when the total number of carbon atoms is 4).

From the viewpoint of the IOB being between about 0.00 and about 0.60, in a triether of pentaerythritol and an aliphatic monohydric alcohol, the total number of carbon atoms of the aliphatic monohydric alcohol composing the triether of pentaerythritol and the aliphatic monohydric alcohol, i.e. the total number of carbon atoms of the $R^{10}$, $R^{11}$ and $R^{12}$ portions in formula (11), is preferably about 9 or greater (the IOB is 0.57 when the total number of carbon atoms is 9).

From the viewpoint of the IOB being between about 0.00 and about 0.60, in a diether of pentaerythritol and an aliphatic monohydric alcohol, the total number of carbon atoms of the aliphatic monohydric alcohol composing the diether of pentaerythritol and the aliphatic monohydric alcohol, i.e. the total number of carbon atoms of the $R^{10}$ and $R^{11}$ portions in formula (12), is preferably about 15 or greater (the IOB is 0.60 when the total number of carbon atoms is 15).

From the viewpoint of the IOB being between about 0.00 and about 0.60, in a monoether of pentaerythritol and an aliphatic monohydric alcohol, the number of carbon atoms of the aliphatic monohydric alcohol composing the monoether of pentaerythritol and the aliphatic monohydric alcohol, i.e. the number of carbon atoms of the $R^{10}$ portion in formula (13), is preferably about 22 or greater (the IOB is 0.59 when the number of carbon atoms is 22).

From the viewpoint of the IOB being between about 0.00 and about 0.60, in a triether of glycerin and an aliphatic monohydric alcohol, the total number of carbon atoms of the aliphatic monohydric alcohol composing the triether of glycerin and the aliphatic monohydric alcohol, i.e. the total number of carbon atoms of the $R^{14}$, $R^{15}$ and $R^{16}$ portions in formula (14), is preferably about 3 or greater (the IOB is 0.50 when the total number of carbon atoms is 3).

From the viewpoint of the IOB being between about 0.00 and about 0.60, in a diether of glycerin and an aliphatic monohydric alcohol, the total number of carbon atoms of the aliphatic monohydric alcohol composing the diether of glycerin and the aliphatic monohydric alcohol, i.e. the total number of carbon atoms of the $R^{14}$ and $R^{15}$ portions in formula (15), is preferably about 9 or greater (the IOB is 0.58 when the total number of carbon atoms is 9).

From the viewpoint of the IOB being between about 0.00 and about 0.60, in a monoether of glycerin and an aliphatic monohydric alcohol, the number of carbon atoms of the aliphatic monohydric alcohol composing the monoether of glycerin and the aliphatic monohydric alcohol, i.e. the number of carbon atoms of the $R^{14}$ portion in formula (16), is preferably 16 or greater (the IOB is 0.58 when the number of carbon atoms is 16).

From the viewpoint of the IOB being from about 0.00 to about 0.60, in a diether of butylene glycol represented by formula (17) (n=4) and an aliphatic monohydric alcohol, the total number of carbon atoms of the $R^{17}$ and $R^{18}$ portions is preferably about 2 or greater (the IOB is 0.33 when the total number of carbon atoms is 2).

From the viewpoint of the IOB being from about 0.00 to about 0.60, in a monoether of ethylene glycol represented by formula (18) (n=2) and an aliphatic monohydric alcohol, the number of carbon atoms of the $R^{17}$ portion is preferably about 8 or greater (the IOB is 0.60 when the number of carbon atoms is 8).

Compound (B) can be produced by dehydrating condensation of compound (B1) and compound (B2) in the presence of an acid catalyst.

[(C) Ester of (C1) a Carboxylic Acid, Hydroxy Acid, Alkoxy Acid or Oxoacid Comprising a Chain Hydrocarbon Moiety and 2-4 Carboxyl Groups Substituting for Hydrogens on the Chain Hydrocarbon Moiety and (C2) a Compound Having a Chain Hydrocarbon Moiety and 1 Hydroxyl Group Substituting for a Hydrogen on the Chain Hydrocarbon Moiety]

In the (C) ester of (C1) a carboxylic acid, hydroxy acid, alkoxy acid or oxoacid comprising a chain hydrocarbon moiety and 2-4 carboxyl groups substituting for hydrogens on the chain hydrocarbon moiety and (C2) a compound having a chain hydrocarbon moiety and 1 hydroxyl group substituting for a hydrogen on the chain hydrocarbon moiety (hereunder also referred to as "compound (C)"), it is not necessary for all of the carboxyl groups to be esterified so long as the kinematic viscosity, water holding percentage and weight-average molecular weight are within the aforementioned ranges.

Examples for the (C1) carboxylic acid, hydroxy acid, alkoxy acid or oxoacid including a chain hydrocarbon moiety and 2-4 carboxyl groups substituting hydrogens of the chain hydrocarbon moiety (hereunder also referred to as "compound (C1)") include chain hydrocarbon carboxylic acids with 2-4 carboxyl groups, for example, chain hydrocarbon dicarboxylic acids, which include alkanedicarboxylic acids, such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, which include alkanetricarboxylic acids, such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, which include alkanetetracarboxylic acids, such as butanetetraoic acid, pentanetetraoic acid, hexanetetraoic acid, heptanetetraoic acid, octanetetraoic acid, nonanetetraoic acid and decanetetraoic acid.

Also, compound (C1) includes chain hydrocarbon hydroxy acids with 2-4 carboxyl groups, for example, chain hydrocarbon alkoxy acids with 2-4 carboxyl groups, such as malic acid, tartaric acid, citric acid and isocitric acid, and O-acetylcitric acid or chain hydrocarbon oxoacids with 2-4 carboxyl groups.

The (C2) compound with a chain hydrocarbon moiety and one hydroxyl group substituting at a hydrogen of the chain hydrocarbon moiety may be any of those mentioned for "compound (B)", such as an aliphatic monohydric alcohol.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or ($c_3$) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate and tributyl O-acetylcitrate, of which commercially available products exist.

[(D) Compound Having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted Between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") may be ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, or ($d_4$) a dialkyl carbonate.

[($d_1$) Ether of an Aliphatic Monohydric Alcohol and an Aliphatic Monohydric Alcohol]

Ethers of aliphatic monohydric alcohols and aliphatic monohydric alcohols include compounds having the following formula (19):

$$R^{19}OR^{20} \qquad (19)$$

wherein $R^{19}$ and $R^{20}$ each represent a chain hydrocarbon.

The aliphatic monohydric alcohol composing the ether (corresponding to $R^{19}OH$ and $R^{20}OH$ in formula (19)) is not particularly restricted so long as the ether satisfies the conditions for the kinematic viscosity, water holding percentage and weight-average molecular weight, and for example, it may be one of the aliphatic monohydric alcohols mentioned for "compound (B)".

[($d_2$) Dialkyl Ketone]

The dialkyl ketone may be a compound of the following formula (20):

$$R^{21}COR^{22} \qquad (20)$$

wherein $R^{21}$ and $R^{22}$ are each an alkyl group.

The dialkyl ketone may be a commercially available product, or it may be obtained by a known method, such as by oxidation of a secondary alcohol with chromic acid or the like.

[($d_3$) Ester of a Fatty Acid and an Aliphatic Monohydric Alcohol]

Examples of esters of fatty acids and aliphatic monohydric alcohols include compounds having the following formula (21):

$$R^{23}COOR^{24} \qquad (21)$$

wherein $R^{23}$ and $R^{24}$ each represent a chain hydrocarbon.

Examples of fatty acids composing esters (corresponding to $R^{23}COOH$ in formula (21)) include the fatty acids mentioned for the "($a_1$) esters of chain hydrocarbon tetraols and fatty acids", and specifically these include saturated fatty acids and unsaturated fatty acids, with saturated fatty acids being preferred in consideration of the potential for degradation by oxidation and the like. The aliphatic monohydric alcohol composing the ester (corresponding to $R^{24}OH$ in formula (21)) may be one of the aliphatic monohydric alcohols mentioned for "compound (B)".

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[(d₄) Dialkyl Carbonate]

The dialkyl carbonate may be a compound of the following formula (22):

$$R^{25}OC(=O)OR^{26} \qquad (22)$$

wherein $R^{25}$ and $R^{26}$ are each an alkyl group.

The dialkyl carbonate may be a commercially available product, or it may be synthesized by reaction between phosgene and an alcohol, reaction between formic chloride ester and an alcohol or alcoholate, or reaction between silver carbonate and an alkyl iodide.

From the viewpoint of the water holding percentage and vapor pressure, the weight-average molecular weight is preferably about 100 or greater and more preferably about 200 or greater, for (d₁) an ether of an aliphatic monohydric alcohol and an aliphatic monohydric alcohol, (d₂) a dialkyl ketone, (d₃) an ester of a fatty acid and an aliphatic monohydric alcohol, and (d₄) a dialkyl carbonate.

If the total number of carbon atoms is about 8 in a (d₂) dialkyl ketone, the melting point will be approximately −50° C. and the vapor pressure will be about 230 Pa at 20° C., in the case of 5-nonanone, for example.

[(E) Polyoxy $C_3$-$C_6$ Alkylene Glycol, or Alkyl Ester or Alkyl Ether Thereof]

The (E) polyoxy $C_3$-$C_6$ alkylene glycol, or alkyl ester or alkyl ether thereof (hereunder also referred to as "compound (E)") may be (e₁) a polyoxy $C_3$-$C_6$ alkylene glycol, (e₂) an ester of a polyoxy $C_3$-$C_6$ alkylene glycol and at least one fatty acid, or (e₃) an ether of a polyoxy $C_3$-$C_6$ alkylene glycol and at least one aliphatic monohydric alcohol. These will now be explained.

[(e₁) Polyoxy $C_3$-$C_6$ Alkylene Glycol]

The polyoxy $C_3$-$C_6$ alkylene glycol is i) a homopolymer having one backbone selected from the group consisting of oxy $C_3$-$C_6$ alkylene backbones, i.e. oxyethylene backbone, oxypropylene backbone, oxybutylene backbone, oxypentylene backbone and oxyhexylene backbone, and having hydroxy groups at both ends, ii) a block copolymer having a backbone of two or more selected from among the aforementioned group and having hydroxy groups at both ends, or iii) a random copolymer having a backbone of two or more selected from among the aforementioned group and having hydroxy groups at both ends.

A polyoxy $C_3$-$C_6$ alkylene glycol is represented by the following formula (23):

$$HO-(C_mH_{2m}O)_n-H \qquad (23)$$

wherein m is an integer of 3-6.

The present inventors have found that with polypropylene glycol (corresponding to a homopolymer of formula (23) where m=3), the condition for the water holding percentage is not satisfied when the weight-average molecular weight is less than about 1,000. Therefore, polypropylene glycol homopolymer is not included in the scope of the blood slipping agent described above, and propylene glycol should be included in the (e₁) polyoxy $C_3$-$C_6$ alkylene glycol only as a copolymer or random polymer with another glycol.

Incidentally, investigation by the present inventors suggests that with polyethylene glycol (corresponding to a homopolymer of formula (23) where m=2), the condition for the kinematic viscosity and water holding percentage cannot be satisfied when the weight-average molecular weight is less than about 1,000.

From the viewpoint of the IOB being about 0.00 to about 0.60, when formula (23) is polybutylene glycol (a homopolymer where m=4), for example, preferably n≥about 7 (when n=7, the IOB is 0.57).

Examples of commercial products of poly $C_3$-$C_6$ alkylene glycols include UNIOL™ PB-500 and PB-700 (all products of NOF Corp.).

[(e₂) Ester of a Polyoxy $C_3$-$C_6$ Alkylene Glycol and at Least One Fatty Acid]

The ester of a polyoxy $C_3$-$C_6$ alkylene glycol and at least one fatty acid may be one wherein one or both of the OH ends of a polyoxy $C_3$-$C_6$ alkylene glycol mentioned above under "(e₁) Polyoxy $C_3$-$C_6$ alkylene glycol" are esterified by a fatty acid, i.e. a monoester or a diester.

Examples of fatty acids to be esterified in the ester of a polyoxy $C_3$-$C_6$ alkylene glycol and at least one fatty acid include the fatty acids mentioned above under "(a₁) Ester of chain hydrocarbon tetraol and at least one fatty acid", and specifically these include saturated fatty acids and unsaturated fatty acids, with saturated fatty acids being preferred in consideration of the potential for degradation by oxidation and the like.

[(e₃) Ether of a Polyoxy $C_3$-$C_6$ Alkylene Glycol and at Least One Aliphatic Monohydric Alcohol]

The ether of a polyoxy $C_3$-$C_6$ alkylene glycol and at least one aliphatic monohydric alcohol may be one wherein one or both of the OH ends of a polyoxy $C_3$-$C_6$ alkylene glycol mentioned above under "(e₁) Polyoxy $C_3$-$C_6$ alkylene glycol" are etherified by an aliphatic monohydric alcohol, i.e. a monoether or diether.

In an ether of a polyoxy $C_3$-$C_6$ alkylene glycol and at least one aliphatic monohydric alcohol, the aliphatic monohydric alcohol to be etherified may be an aliphatic monohydric alcohol among those mentioned for "compound (B)".

[(F) Chain Hydrocarbon]

Examples of chain hydrocarbons include (f₁) chain alkanes, such as straight-chain alkanes and branched chain alkanes. Straight-chain alkanes with melting points of about 45° C. or less have up to about 22 carbon atoms, and at a vapor pressure of 1 atmosphere and about 0.01 Pa or less at 25° C., the number of carbon atoms is 13 or greater. Branched chain alkanes tend to have lower melting points than straight-chain alkanes, given the same number of carbon atoms. Branched chain alkanes may therefore include those with 22 and more carbon atoms, even with melting points of below about 45° C.

Examples of commercially available hydrocarbon products include PARLEAM 6 (NOF Corp.).

At least the projections 8 of the excretory opening contact region 20 may be coated with the blood slipping agent alone, or with a blood slipping agent-containing composition comprising the blood slipping agent and at least one other component.

Such a blood slipping agent-containing composition will now be described. Coating of the blood slipping agent-containing composition is the same as coating of the blood slipping agent, and explanation thereof will therefore be omitted.

[Blood Slipping Agent-Containing Composition]

The blood slipping agent-containing composition contains the aforementioned blood slipping agent and at least one other component. The other component is not particularly restricted so long as it does not inhibit the function and effect of the blood slipping agent, and it may be any one commonly employed in absorbent articles of the field, and especially top sheets.

Examples for the other component(s) include silicone oils, silicones, silicone-based resins and the like.

Examples for the other component(s) also include antioxidants, such as BHT (2,6-di-t-butyl-p-cresol), BHA (butylated hydroxyanisole) and propyl gallate.

Further examples for the other component(s) include vitamins, such as natural vitamins and synthetic vitamins. Examples of vitamins include water-soluble vitamins, such as group B vitamins, including $B_1$, vitamin $B_2$, vitamin $B_3$, vitamin $B_5$, vitamin $B_6$, vitamin $B_7$, vitamin $B_9$ and vitamin $B_{12}$, and vitamin C.

Other examples of vitamins include fat-soluble vitamins, such as group A vitamins, group D vitamins, group E vitamins and group K vitamins. The derivatives of these vitamins are also included.

Examples for the other component(s) include amino acids, such as alanine, arginine, lysine, histidine, proline and hydroxyproline, and peptides.

Other examples for the other component(s) include zeolite, such as natural zeolite, examples of which include analcite, chabazite, heulandite, natrolite, stilbite and thomosonite, and synthetic zeolite.

Still other examples for the other component(s) include cholesterol, hyaluronic acid, lecithin and ceramide.

Yet other examples for the other component(s) include drugs, such as skin astringents, anti-pimple medications, anti-wrinkle agents, anti-cellulite agents, skin whiteners, antimicrobial agents and antifungal agents.

Examples of skin astringents include zinc oxide, aluminum sulfate, tannic acid and the like, and oil-soluble skin astringents, such as fat-soluble polyphenols. Fat-soluble polyphenols include natural fat-soluble polyphenols, such as barley extract, otogiriso extract, white deadnettle extract, chamomilla extract, burdock extract, *salvia* extract, linden extract, common lime extract, white birch extract, common horsetail extract, sage extract, *salvia* extract, walnut (*J. regia* L. var. *orientalis*) extract, hibiscus extract, loquat leaf extract, Miquel's linden extract, hop extract, common horsechestnut extract and *coix* seed extract.

Examples of anti-pimple medications include salicylic acid, benzoyl peroxide, resorcinol, sulfur, erythromycin and zinc.

Examples of anti-wrinkle agents include lactic acid, salicylic acid, salicylic acid derivatives, glycolic acid, phytic acid, lipoic acid and lysophosphatidic acid.

Examples of anti-cellulite agents include xanthine compounds, such as aminophylline, caffeine, theophylline and theobromine.

Examples of skin whiteners include niacinamide, kojic acid, arbutin, glucosamine and its derivatives, phytosterol derivatives, and ascorbic acid and its derivatives, as well as mulberry extract and placenta extract.

Examples for the other component(s) also include anti-inflammatory components, pH regulators, antimicrobial agents, humectants, aromatics, pigments, dyes, pigments and plant extracts.

Examples of anti-inflammatory components include naturally-derived anti-inflammatory drugs, such as peony, golden grass, otogiriso, chamomile, licorice, peach leaf, Japanese mugwort and *perilla* extract, and synthetic anti-inflammatory drugs, such as allantoin and dipotassium glycyrrhizinate.

Examples of pH regulators include those that keep the skin weakly acidic, such as malic acid, succinic acid, citric acid, tartaric acid and lactic acid.

Titanium oxide is an example of a pigment.

The blood slipping agent-containing composition contains the blood slipping agent and the one or more other components at preferably about 50 to about 99 mass % and about 1 to about 50 mass %, respectively, more preferably about 60 to about 99 mass % and about 1 to about 40 mass %, respectively, even more preferably about 70 to about 99 mass % and about 1 to about 30 mass %, respectively, yet more preferably about 80 to about 99 mass % and about 1 to about 20 mass %, respectively, even yet more preferably about 90 to 99 mass % and about 1 to about 10 mass %, respectively, and even yet more preferably about 95 to 99 mass % and about 1 to about 5 mass %, respectively. This is from the viewpoint of the functions and effects of the blood slipping agent and the other components.

The blood slipping agent-containing composition preferably contains a surfactant in not greater than the amount from hydrophilicizing treatment of the top sheet or second sheet. More specifically, the blood slipping agent-containing composition contains a surfactant in a basis weight range of preferably about 0.0 to about 1.0 g/m$^2$, more preferably about 0.0 to about 0.8 g/m$^2$, even more preferably about 0.1 to about 0.5 g/m$^2$, and yet more preferably about 0.1 to about 0.3 g/m$^2$.

This is because when the amount of surfactant is increased, menstrual blood will tend to be retained in the top sheet. The surfactant, incidentally, has no water holding percentage. This is because there is no layer of the substance to be measured due to its mixture with water.

The blood slipping agent-containing composition contains water in a basis weight range of preferably about 0.0 to about 1.0 g/m$^2$, more preferably about 0.0 to about 0.8 g/m$^2$, even more preferably about 0.1 to about 0.5 g/m$^2$, and yet more preferably about 0.1 to about 0.3 g/m$^2$. Since water lowers the absorption performance of the absorbent article, the amount is preferably low.

Similar to the blood slipping agent, the blood slipping agent-containing composition, as a composition, has at 40° C., a kinematic viscosity of preferably about 0 to about 80 mm$^2$/s, more preferably a kinematic viscosity of about 1 to about 70 mm$^2$/s, even more preferably a kinematic viscosity of about 3 to about 60 mm$^2$/s, yet more preferably a kinematic viscosity of about 5 to about 50 mm$^2$/s, and even yet more preferably a kinematic viscosity of about 7 to about 45 mm$^2$/s.

If the kinematic viscosity of the blood slipping agent-containing composition exceeds 80 mm$^2$/s, the viscosity will increase and the blood slipping agent composition may not slide down into the interior of the absorbent article as easily with menstrual blood that has reached the skin contact surface of the top sheet.

When the blood slipping agent-containing composition contains a component that is miscible with the blood slipping agent, as at least one other component, the other component preferably has a weight-average molecular weight of less than about 1,000, and more preferably a weight-average molecular weight of less than about 900. This is because if the weight-average molecular weight is about 1,000 or higher, tack may result in the blood slipping agent-containing composition itself, tending to create a feeling of discomfort for the wearer. If the weight-average molecular weight increases, the viscosity of the blood slipping agent-containing composition will tend to increase, and it will therefore be difficult to lower the viscosity of the blood slipping agent composition by heating to a viscosity suitable for coating, and as a result, the blood slipping agent may need to be diluted with a solvent.

The blood slipping agent-containing composition, as a composition, has a water holding percentage of about 0.01 to about 4.0 mass %, preferably it has a water holding percentage of about 0.02 to about 3.5 mass %, more preferably it has a water holding percentage of about 0.03 to about 3.0 mass %, even more preferably it has a water holding percentage of about 0.04 to about 2.5 mass %, and yet more preferably it has a water holding percentage of about 0.05 to about 2.0 mass %.

A low water holding percentage value will tend to lower the affinity between the blood slipping agent composition and menstrual blood, thus inhibiting it from slipping down into the interior of the absorbent article with menstrual blood that has reached the skin contact surface of the top sheet.

When the blood slipping agent-containing composition contains solid matter, it is preferably removed by filtration for measurement of the kinematic viscosity and water holding percentage.

EXAMPLES

The invention will now be further explained by production examples and test examples, with the understanding that the invention is not limited to the production examples and test examples.

In the following production examples and test examples, the fiber materials and absorbent bodies produced using heat sealable composite fibers A (hereunder referred to as "composite fibers A") are each referred to as "fiber material A" and "absorbent body A", respectively, and the fiber materials and absorbent bodies produced using heat sealable composite fibers B (hereunder referred to as "composite fibers B") are referred to as "fiber material B" and "absorbent body B", respectively. Also, the absorbent bodies produced using fiber materials A1 to A8 having different mass mixing ratios for the composite fibers A with respect to the pulp are referred to as "absorbent bodies A1 to A8", and the absorbent bodies produced using fiber materials B1 to B8 having different mass mixing ratios for the composite fibers B with respect to the pulp are referred to as "absorbent bodies B1 to B8".

Production Example 1

Production of Absorbent Bodies A (A1 to A8) and B (B1 to B8)

(1) Production of Fiber Materials A (A1 to A8)

Pulp (NB416 by Warehouser) and composite fibers A were blended and layered in pulp:composite fiber A mass ratios of 9.5:0.5 (A1), 9:1 (A2), 8:2 (A3), 6.5:3.5 (A4), 5:5 (A5), 3.5:6.5 (A6), 2:8 (A7) and 0:10 (A8), to prepare fiber materials A1 to A8 (basis weight: 200 g/m²).

The composite fibers A were core-sheath composite fibers having polyethylene terephthalate (PET) as the core component and high-density polyethylene (HDPE), graft polymerized with a maleic anhydride-containing vinyl polymer, as the sheath component. The core-sheath ratio of the composite fibers A was 50:50 (mass ratio), the titanium oxide content of the core component was 0.7 mass %, the size was 2.2 dtex and the fiber length was 6 mm.

(2) Production of Fiber Materials B (B1 to B8)

Pulp (NB416 by Warehouser) and composite fibers B were blended and layered in pulp:composite fiber B mass ratios of 10:0 (B1), 9:1 (B2), 8:2 (B3), 6.5:3.5 (B4), 5:5 (B5), 3.5:6.5 (B6), 2:8 (B7) and 0:10 (B8), to prepare fiber materials B1 to B8 (basis weight: 200 g/m²).

The composite fibers B were core-sheath composite fibers having polyethylene terephthalate (PET) as the core component and ordinary high-density polyethylene (HDPE) as the sheath component. The core-sheath ratio of the composite fibers B was 50:50 (mass ratio), the titanium oxide content of the core component was 0.7 mass %, the size was 2.2 dtex and the fiber length was 6 mm.

(3) Production of Absorbent Bodies A (A1 to A8) and B (B1 to B8)

Fiber materials A1 to A8 and B1 to B8 were bonded by a common through-air method, and the composite fibers A and B were heat fused to produce absorbent bodies A1 to A8 and B1 to B8. The heating temperature was 135° C., the airflow rate was 5 m/sec and the heating time was 20 seconds.

The compositions and physical properties of absorbent bodies A1 to A8 and B1 to B8 are shown in Table 2.

Measurement of the basis weight, thickness and density of each absorbent body was carried out in the following manner.

The density of each absorbent body was calculated by the following formula.

$$D(\text{g/cm}^3) = B(\text{g/m}^2)/T(\text{mm}) \times 10^{-3}$$

wherein D, B and T represent the density, basis weight and thickness, respectively, of the absorbent body.

Measurement of the basis weight (g/m²) of the absorbent body was carried out in the following manner.

Three 100 mm×100 mm test pieces are cut out from the absorbent body, the mass of each test piece is measured under standard conditions (temperature: 23±2° C., relative humidity: 50±5%) using a digital balance (electronic scale HF-300 by Kensei Co., Ltd.), and the mass per unit area (g/m²) of the absorbent body calculated from the average of the three measured values is recorded as the basis weight of the absorbent body.

Any measuring conditions not specified above for measurement of the basis weight of the absorbent body, were the measuring conditions described in ISO 9073-1 or JIS L 1913 6.2.

Measurement of the thickness (mm) of the absorbent body was conducted in the following manner.

Using a thickness gauge (an FS-60DS by Daiei Kagaku Seiki Mfg. Co., Ltd., measuring surface: 44 mm (diameter), measuring pressure: 3 g/cm²), five different locations of the absorbent body (a diameter of 44 mm for each site) are pressed at a constant pressure of 3 g/cm² under standard conditions (temperature: 23±2° C., relative humidity: 50±5%), the thickness is measured after 10 seconds of pressing at each site, and the mean value of the five measured values is recorded as the thickness of the absorbent body.

Measurement of the basis weight, thickness and density of the absorbent bodies for the other production examples and test examples were carried out in the same manner.

TABLE 2

| | | Composition | | | Physical properties after heat treatment | | |
|---|---|---|---|---|---|---|---|
| | | Pulp basis weight (g/m²) | Composite fiber basis weight (g/m²) | Mass mixing ratio (pulp:composite fiber) | Actual basis weight (g/m²) | Thickness (mm) | Density (g/cm³) |
| Absorbent body | A1 | 190 | 10 | 9.5:0.5 | 203 | 8.68 | 0.0234 |
| | A2 | 180 | 20 | 9:1 | 210 | 8.92 | 0.0235 |
| | A3 | 160 | 40 | 8:2 | 197 | 8.76 | 0.0225 |
| | A4 | 130 | 70 | 6.5:3.5 | 206 | 9.53 | 0.0216 |
| | A5 | 100 | 100 | 5:5 | 215 | 9.27 | 0.0232 |
| | A6 | 70 | 130 | 3.5:6.5 | 219 | 8.54 | 0.0256 |
| | A7 | 40 | 160 | 2:8 | 223 | 6.87 | 0.0325 |
| | A8 | 0 | 200 | 0:10 | 222 | 6.47 | 0.0344 |
| | B1 | 200 | 0 | 10:0 | — | — | — |
| | B2 | 180 | 20 | 9:1 | 205 | 8.66 | 0.0237 |
| | B3 | 160 | 40 | 8:2 | 206 | 8.21 | 0.0251 |
| | B4 | 130 | 70 | 6.5:3.5 | 215 | 9.07 | 0.0237 |
| | B5 | 100 | 100 | 5:5 | 214 | 9.02 | 0.0237 |
| | B6 | 70 | 130 | 3.5:6.5 | 222 | 9.07 | 0.0245 |
| | B7 | 40 | 160 | 2:8 | 223 | 7.97 | 0.0280 |
| | B8 | 0 | 200 | 0:10 | 218 | 5.63 | 0.0387 |

Production Example 2

Production of Absorbent Articles A (A1 to A5) and B (B1 to B5)

The air-blasted side of an air-through nonwoven fabric (basis weight: 30 g/m², size: 100 mm length (MD direction)×80 mm width (CD direction)), was coated with a hot-melt adhesive (HMA) to a basis weight of 5 g/m² using a spiral spray gun (product of Nordson, KK.), and then each of absorbent bodies A1 to A5 and B1 to B5 (basis weight: 200 g, size: 100 mm length (MD direction)×80 mm width (CD direction) was attached thereto. This was followed by heat embossing treatment to form embossed sections partially joining the nonwoven fabric and absorbent body, to produce absorbent articles A1 to A5 and B1 to B5.

The nonwoven fabric used was a nonwoven fabric with a two-layer structure, having an upper layer and a lower layer. The upper layer was composed of core-sheath composite fibers with polyethylene terephthalate (PET) as the core component (titanium oxide content of 4 mass % in the core component) and high-density polyethylene (HDPE) as the sheath component (size: 2.8 dtex, fiber length: 44 mm) (basis weight: 20 g/m²), and the lower layer was composed of core-sheath composite fibers with polyethylene terephthalate (PET) as the core component (titanium oxide content of 4 mass % in the core component) and high-density polyethylene (HDPE) as the sheath component (size: 2.2 dtex, fiber length: 44 mm) (basis weight: 10 g/m²), and the basis weight of the nonwoven fabric as a whole was 30 g/m². The strength of the nonwoven fabric (maximum point strength) was 24.7 N/25 mm in the MD direction and 3.93 N/25 mm in the CD direction.

The nonwoven fabric was produced by laminating the upper layer and lower layer with a carding machine, carrying out hot air treatment, and then subjecting the surface to hydrophilicizing treatment with a surfactant.

As the HMA there was used a common HMA having a pressure-sensitive adhesive component added to a thermoplastic elastomer (SIS-based or SBS-based). The HMA used had a viscosity of 40500 cps at 120° C., 11000 cps at 140° C., 4100 cps at 160° C. and 2000 cps at 180° C.

The heat embossing treatment was conducted using an embossing plate (heating temperature: 110° C.) having projections formed thereon as the plate on the nonwoven fabric side (top), and using a flat plate (heating temperature: 110° C.) as the plate on the absorbent body sample side (bottom). The embossing treatment time was 3 seconds and the embossing pressure was 5 MPa (5 kPa/mm²). By heat embossing treatment, embossed sections were formed extending in the lengthwise direction of the absorbent article, when the absorbent article was viewed flat from the nonwoven fabric side. The embossed sections contained low compression sections and high compression sections, the area of the low compression sections being 803.01 mm² and the area of the high compression sections being 188.65 mm².

Production Example 3

Production of Density-Increased Absorbent Bodies A (A2 to A8) and B (B1 to B8)

A carrier sheet (tissue basis weight: 14 g/m², product of UCKN) was mounted on each of fiber materials A2 to A8 (see Production Example 1) and bonded by a common through-air method, and after heat fusion of composite fibers A (heating temperature: 135° C., airflow rate: 5 m/sec, heating time: 20 sec), the density was adjusted to approximately 0.08 g/cm³ (0.0793 to 0.0817 g/cm³) with a steam jet (SJ) belt press machine, to produce density-increased absorbent bodies A2 to A8 (120 mm×120 mm, 3 samples each).

Fiber materials B1 to B8 (see Production Example 1) were used to produce density-increased absorbent bodies B1 to B8 (120 mm×120 mm, 3 samples each), in the same manner.

The construction of the SJ belt press machine used is illustrated in FIG. 4.

As shown in FIG. 4(a), the SJ belt press machine 9 comprises mesh conveyor belts 91a, 91b, a steam nozzle 92 and a suction box 93, and an absorbent body sandwiched between the pair of mesh conveyor belts 91a, 91b is transported between a mutually opposing steam nozzle 92 and suction box 93, spraying high-pressure steam toward the absorbent body through the steam nozzle 92, thereby compacting the absorbent body. The water vapor that has passed through the absorbent body is aspirated by the suction box 93 and ejected. The thickness of the absorbent body can be adjusted by varying the spacing between the pair of mesh conveyor belts 91a, 91b.

The mesh conveyor belts 91a, 91b are plain weave mesh conveyors made of polyphenylene sulfide (product of Nippon Filcon Co., Ltd.), having a longitudinal/transverse line size of 0.37 mm, with 34 longitudinal lines/inch and 32 transverse lines/inch. The distance between the mesh conveyor belts 91a, 91b was adjusted to 1 mm or 0.2 mm, and the line speed was 200 m/sec.

The steam nozzle 92 had 0.5 mm caliber open holes formed with a hole pitch of 2 mm/5 mm, as shown in FIG. 4(b), the vapor pressure of the sprayed water vapor was 0.7 MPa, and the steam treatment volume was 1.27 kg/m² per unit area.

The compositions and physical properties of density-increased absorbent bodies A2 to A8 and B1 to B8 are shown in Table 3.

TABLE 3

|  |  | Composition | Physical properties after density adjustment | | |
|---|---|---|---|---|---|
|  |  | Mass mixing ratio (pulp:composite fiber) | Actual basis weight (g/m²) | Thickness (mm) | Density |
| Density-increased absorbent body | A2 | 9:1 | 210 | 2.63 | 0.0798 |
|  | A3 | 8:2 | 197 | 2.46 | 0.0801 |
|  | A4 | 6.5:3.5 | 206 | 2.55 | 0.0808 |
|  | A5 | 5:5 | 215 | 2.71 | 0.0793 |
|  | A6 | 3.5:6.5 | 219 | 2.74 | 0.0799 |
|  | A7 | 2:8 | 223 | 2.79 | 0.0799 |
|  | A8 | 0:10 | 222 | 2.77 | 0.0801 |
|  | B1 | 10:0 | — | — | — |
|  | B2 | 9:1 | 205 | 2.54 | 0.0807 |
|  | B3 | 8:2 | 206 | 2.52 | 0.0817 |
|  | B4 | 6.5:3.5 | 215 | 2.63 | 0.0817 |
|  | B5 | 5:5 | 214 | 2.63 | 0.0814 |
|  | B6 | 3.5:6.5 | 222 | 2.73 | 0.0813 |
|  | B7 | 2:8 | 223 | 2.76 | 0.0808 |
|  | B8 | 0:10 | 218 | 2.74 | 0.0796 |

Test Example 1

Measurement of Gurley Bending Resistance of Absorbent Articles A (A1 to A5) and B (B1 to B5)

(1) Measuring Method

A No. 311 Gurley flexibility tester (product of Yasuda Seiki Seisakusho Co., Ltd.) was used for measurement of the Gurley bending resistance. The tester is one that measures the flexibility (bending repulsion) of a sample piece according to JIS-L1096, the sample piece being mounted on a moving arm chuck and rotated at a fixed speed in the left-right direction, with the scale being read when the bottom edge of the sample piece separates from the pendulum, and the bending resistance S (mN) being calculated by the following formula.

$$S = R \times (D_1 W_1 + D_2 W_2 + D_3 W_3) \times (L - 12.7)^2 / b \times 3.375 \times 10^{-5}$$

wherein R is the value read from the scale pointer, $D_1$, $D_2$ and $D_3$ are the distances from the pendulum fulcrum to the weight mounting positions (25.4 mm (1 in.), 50.8 mm (2 in.), 101.6 mm (4 in.)), $W_1$, $W_2$ and $W_3$ are the masses (g) of the weights mounted at holes of $D_1$, $D_2$ and $D_3$, L is the length (mm) of the sample piece, and b is the width (mm) of the sample piece.

Each of the absorbent articles A1 to A5 and B1 to B5 produced in Production Example 2 was cut perpendicular to the embossed section to create five sample pieces (40 mm length×12.5 mm width), and the Gurley bending resistance (mN) per 12.5 mm width in the lengthwise direction (MD direction) of the sample piece was measured.

For measurement of the dry Gurley bending resistance, a standard sample piece was used (environment temperature: 20° C., humidity: 60%), and for measurement of the wet Gurley bending resistance, there was used a sample piece that had been dipped in ion-exchanged water until it sunk under its own weight, or a sample piece that had been immersed in water for 1 hour or longer.

(3) Results and Observations

The measurement results are shown in Table 4.

TABLE 4

|  |  | Absorbent body composition | Gurley bending resistance (mN/12.5 mm) | | |
|---|---|---|---|---|---|
|  |  | Mass mixing ratio (pulp:composite fiber) | Dry | Wet | Difference between dry and wet |
| Absorbent article | A1 | 9.5:0.5 | 4.44 | 2.27 | 2.17 |
|  | A2 | 9:1 | 4.82 | 2.32 | 2.50 |
|  | A3 | 8:2 | 4.92 | 2.68 | 2.24 |
|  | A4 | 6.5:3.5 | 5.24 | 3.36 | 1.88 |
|  | A5 | 5:5 | 6.09 | 3.98 | 2.11 |
|  | B1 | 10:0 | 4.39 | 1.54 | 2.85 |
|  | B2 | 9:1 | 3.22 | 1.50 | 1.72 |
|  | B3 | 8:2 | 3.36 | 1.68 | 1.68 |
|  | B4 | 6.5:3.5 | 3.48 | 2.18 | 1.31 |
|  | B5 | 5:5 | 3.56 | 2.55 | 1.01 |

The following observations are made based on Table 4.

When the absorbent body contains only pulp, the difference between the dry Gurley bending resistance and wet Gurley bending resistance is 2.85 N/12.5 mm, but when the absorbent body contains pulp and composite fibers A, the difference between the dry Gurley bending resistance and the wet Gurley bending resistance is 2.5 mN/12.5 mm or less, regardless of the mass mixing ratio. Thus, it is advantageous for the absorbent body to contain pulp and composite fibers A, from the viewpoint of maintaining a difference of 2.5 mN/12.5 mm or less between the dry Gurley bending resistance and the wet Gurley bending resistance. Furthermore, if the mass mixing ratio of the composite fibers A with respect to the pulp in the absorbent body is 1/9 or greater, it will be possible to achieve a dry Gurley bending resistance of at least 4.82 mN/12.5 mm for the embossed sections and a wet Gurley bending resistance of at least 2.32 mN/12.5 mm for the embossed sections. Furthermore, if the mass mixing ratio of the composite fibers A with respect to the pulp in the absorbent body is 1/9 to 5/5, it will be possible to achieve a dry Gurley bending resistance of 4.82 to 6.09 mN/12.5 mm for the embossed sections and a wet Gurley bending resistance of 2.32 to 3.98 mN/12.5 mm for the embossed sections.

Test Example 2

Measurement of Embossed Section Bonding Strengths of Absorbent Articles A (A1 to A5) and B (B2 to B5)

(1) Measuring Method

Each of the absorbent articles A1 to A5 and B2 to B5 produced in Production Example 2 was cut perpendicular to the embossed section to create five sample pieces (50 mm length×25 mm width), and used for measurement of the embossed section bonding strength (N/25 mm).

[Dry Embossed Section Bonding Strength (N/25 mm)]

Standard (20° C. temperature, 60% humidity environment) sample pieces were mounted in a tensile tester (AG-1kNI by Shimadzu Corp.) with a grip spacing of 20 mm, and with the absorbent body on the upper grip and the nonwoven fabric on the lower grip. A load (maximum point load) was applied at a pull rate of 100 mm/min until complete detachment of the nonwoven fabric and absorbent body, and the bonding strength (N) of the embossed sections per 25 mm width of the sample piece was measured using the lengthwise direction of the sample piece as the direction of tension.

[Wet Embossed Section Bonding Strength (N/25 mm)]

The bonding strength (N) of the embossed sections per 25 mm width of the sample piece was measured in the same manner as above, using the lengthwise direction of the sample piece as the direction of tension, after dipping the sample piece in ion-exchanged water until it sunk under its own weight, or after immersing the sample piece in water for 1 hour or longer.

Any measuring conditions not specified for measurement of the dry and wet embossed section bonding strengths were the measuring conditions described in ISO 9073-3 or JIS L 1913 6.3.

(3) Results and Observations

The measurement results are shown in Table 5.

TABLE 5

| Absorbent body composition | | Embossed section bonding strength (N/25 mm) | | |
|---|---|---|---|---|
| | Mass mixing ratio (pulp:composite fiber) | Dry | Wet | Difference between dry and wet |
| Absorbent article | A1 | 9.5:0.5 | 0.99 | 0.73 | 0.26 |
| | A2 | 9:1 | 1.53 | 0.95 | 0.58 |
| | A3 | 8:2 | 3.95 | 2.24 | 1.71 |
| | A4 | 6.5:3.5 | 4.51 | 2.91 | 1.60 |
| | A5 | 5:5 | 7.65 | 4.34 | 3.31 |
| | B2 | 9:1 | 0.96 | 0.75 | 0.21 |
| | B3 | 8:2 | 1.76 | 1.71 | 0.05 |
| | B4 | 6.5:3.5 | 2.37 | 1.99 | 0.38 |
| | B5 | 5:5 | 3.69 | 3.24 | 0.45 |

The following observations are made based on Table 5.

When the embossed section bonding strength is less than 0.75 N/25 mm, this may lead to interfacial peeling between the top sheet and the absorbent body during use of the absorbent article. Therefore, if the condition is that the dry and wet embossed section bonding strengths are both at least 0.75 N/25 mm, absorbent articles A2 to A5 satisfy this condition. Thus, it is advantageous for the mass mixing ratio of the composite fibers A with respect to the pulp in the absorbent body to be at least 1/9 from the viewpoint of increasing the dry and wet embossed section bonding strengths, which makes it possible to obtain a dry embossed section bonding strength of 1.53 N/25 mm or group and a wet embossed section bonding strength of 0.95 N/or greater.

In addition, upon comparing the absorbent articles having the same mass mixing ratios of composite fibers A and B with respect to the pulp in the absorbent body (that is, A2 and B2, A3 and B3, A4 and B4, and A5 and B5), the dry and wet embossed section bonding strengths were larger with absorbent articles A than with absorbent articles B, at all mass mixing ratios. Thus, when the mass mixing ratios of composite fibers A and B with respect to the pulp in the absorbent body are the same, the dry and wet embossed section bonding strengths can be increased more when using composite fibers A than when using composite fibers B. Furthermore, when given dry and wet embossed section bonding strengths have been obtained, it is possible obtain a lower mass mixing ratio of composite fiber with respect to pulp in the absorbent body when using composite fibers A than when using composite fibers B (that is, the mass mixing ratio of pulp is greater, allowing the absorption performance of the absorbent body to be increased).

Test Example 3

Measurement of Maximum Tensile Strengths of Absorbent Bodies A (A2 to A8) and B (B1 to B8)

(1) Measuring Method

Each of the absorbent bodies A2 to A8 and B1 to B8 produced in Production Example 1 was cut to create five sample pieces (150 mm length×25 mm width), and used for measurement of the maximum tensile strength.

[Dry Maximum Tensile Strength (N/25 mm)]

A sample piece was mounted on a tensile tester (AG-1kNI by Shimadzu Corp.) under standard conditions (environment temperature: 20° C., humidity: 60%), with a grip spacing of 100 mm, a load (maximum point load) was applied at a pull rate of 100 mm/min until the sample piece was severed, and the maximum tensile strength per 25 mm width was measured in the lengthwise direction (MD direction) of the sample piece.

[Wet Maximum Tensile Strength (N/25 mm)]

A sample piece was dipped in ion-exchanged water until it sank under its own weight, or the sample piece was immersed in water for 1 hour or longer, and then measurement was performed in the same manner as above to determine the maximum tensile strength per 25 mm width in the lengthwise direction (MD direction) of the sample piece.

Any measuring conditions not specified for measurement of the dry and wet maximum tensile strengths were the measuring conditions described in ISO 9073-3 or JIS L 1913 6.3.

(2) Results and Observations

The measurement results are shown in Table 6.

TABLE 6

| Absorbent body | | Maximum tensile strength (N/25 mm) | | | |
|---|---|---|---|---|---|
| | composition Mass mixing ratio (pulp:composite fiber) | Dry | Wet | Difference between dry and wet | WEB state |
| Absorbent body | A2 | 9:1 | 3.42 | 2.02 | 1.4 | 0.049 |
| | A3 | 8:2 | 9.59 | 5.10 | 4.49 | 0.043 |
| | A4 | 6.5:3.5 | 20.80 | 15.09 | 5.72 | 0.055 |
| | A5 | 5:5 | 40.89 | 33.72 | 7.17 | 0.153 |
| | A6 | 3.5:6.5 | 67.47 | 54.39 | 13.09 | 0.140 |

TABLE 6-continued

| Absorbent body composition Mass mixing ratio (pulp:composite fiber) | Maximum tensile strength (N/25 mm) | | | |
|---|---|---|---|---|
| | | Dry | Wet | Difference between dry and wet | WEB state |
| A7 | 2:8 | 83.19 | 81.25 | 1.94 | 0.095 |
| A8 | 0:10 | 133.64 | 129.06 | 4.58 | 0.060 |
| B1 | 10:0 | 0.375 | 0.01 | 0.37 | 0.375 |
| B2 | 9:1 | 0.46 | 0.35 | 0.11 | 0.032 |
| B3 | 8:2 | 2.33 | 2.04 | 0.30 | 0.190 |
| B4 | 6.5:3.5 | 7.58 | 6.69 | 0.89 | 0.150 |
| B5 | 5:5 | 15.70 | 14.70 | 1.00 | 0.025 |
| B6 | 3.5:6.5 | 27.89 | 25.62 | 2.27 | 0.033 |
| B7 | 2:8 | 41.52 | 37.88 | 3.64 | 0.017 |
| B8 | 0:10 | 67.23 | 61.76 | 5.47 | 0.038 |

The following observations are made based on Table 6.

For absorbent body A, a mass mixing ratio of lower than 1/9 for the composite fibers A with respect to the pulp (composite fibers A/pulp) is expected to result in a wet maximum tensile strength of less than 2 N/25 mm, which may make it impossible to guarantee strength when wet. From the viewpoint of ensuring strength for absorbent body A, therefore, the mass mixing ratio of the composite fibers A with respect to the pulp is preferably at least 1/9.

For absorbent body B, a mass mixing ratio of lower than 2/8 for the composite fibers B with respect to the pulp (composite fibers B/pulp) is expected to result in a wet maximum tensile strength of less than 2 N/25 mm, which may make it impossible to guarantee strength when wet. From the viewpoint of ensuring strength for absorbent body B, therefore, the mass mixing ratio of the composite fibers B with respect to the pulp is preferably at least 2/8.

In addition, upon comparing the absorbent bodies having the same mass mixing ratios of composite fibers A and B with respect to the pulp (for example, A2 and B2), the maximum tensile strengths (dry and wet) were larger with absorbent bodies A than with absorbent bodies B, at all mass mixing ratios. Also, when the mass mixing ratio of the composite fibers A and B with respect to pulp is in the range of 1/9 to 6.5/3.5 (absorbent bodies A2 to A6 and B2 to B6), the difference between the dry maximum tensile strength and the wet maximum tensile strength (dry maximum tensile strength–wet maximum tensile strength) is larger with absorbent bodies A than with absorbent bodies B.

This difference in strength is attributed to the fact that with absorbent bodies A, hydrogen bonds are formed between the oxygen atoms of the acyl and ether bonds of maleic anhydride and the OH groups of cellulose, whereas such hydrogen bonds are not formed with absorbent bodies B.

This is also supported by the maximum tensile strength of each sample in the web state. In other words, the maximum tensile strengths of the samples in the web state were measured to be less than 0.4 N/25 mm for all of the samples (see Table 6), suggesting that the difference in strength is due not to differences in the degree of entangling but rather to the presence or absence of hydrogen bond formation. The sample in the web state is a sample without any treatment after layering of the fiber material on the base material, and it has not been subjected to any treatment including entangling treatment, such as needle punching, heat treatment, such as hot air, embossing, energy waves or the like, or adhesive treatment.

Also, as shown in Table 7 below, since the composite fibers A have a larger heat of fusion than the composite fibers B, the composite fibers A have a higher degree of crystallinity than the composite fibers B, and therefore the difference in strength is believed to be due to the difference in the degrees of crystallinity of the composite fibers A and B (the bonding strength between the fibers themselves).

TABLE 7

| | | Tim (° C.) | Tpm (° C.) | ΔH (J/g) |
|---|---|---|---|---|
| | | 1st heating | | |
| Heat sealable composite fibers | A | 128/213.6 | 131.0/200.3 | 125.7/34.3 |
| | B | 125.6/249.0 | 128.3/251.4 | 86.9/27.6 |
| | | 2nd heating | | |
| Heat sealable composite fibers | A | 123.9/239.2 | 129.8/254.6 | 129.7/28.1 |
| | B | 122.8/241.8 | 129.1/253.6 | 96.5/18.4 |

Incidentally, although Japanese Unexamined Patent Publication No. 2004-270041 teaches that with a maleic anhydride graft-polymerized modified polyolefin, the carboxylic anhydride groups of the maleic anhydride are split and form covalent bonds with hydroxyl groups on the cellulose fiber surfaces, and that adhesion with the cellulose fibers is satisfactory, no increase in strength due to formation of covalent bonds was observed in this result.

Test Example 4

Measurement of Absorption Properties and Maximum Tensile Strengths of Density-Increased Absorbent Bodies A (A2 to A8) and B (B1 to B8)

(1) Measuring Method

[Measurement of Absorption Properties (Penetration Time, Liquid Drain Time)]

A front sheet (front sheet of Sofy Hadaomoi (trade name)) was placed on each density-increased absorbent body A2 to A8 and B1 to B8 produced in Production Example 3, and a perforated acrylic board (40 mm×10 mm hole at the center, 200 mm (length)×100 mm (width)) was layered over it. An autoburette (MultiDojimat Model E725-1, product of Sibata Kagaku Kikai Kogyo Co., Ltd.) was used to inject 3 ml of artificial menstrual blood (a mixture of 80 g glycerin, 8 g carboxymethyl cellulose sodium, 10 g sodium chloride, 4 g sodium hydrogencarbonate, 8 g Red #102, 2 g Red #2 and 2 g Yellow #5 thoroughly stirred with 1 L of ion-exchanged water) toward the hole of the acrylic board at 90 ml/min. The time from the start of injection until the artificial menstrual blood pooled in the acrylic board hole disappeared was recorded as the penetration time (sec), and the time from the start of injection until the artificial menstrual blood disappeared from the front sheet interior was recorded as the drain time (sec).

[Measurement of Dry and Wet Maximum Tensile Strengths]

The dry and wet maximum tensile strengths of density-increased absorbent bodies A2 to A8 and B1 to B8 were measured in the same manner as Test Example 3.

(2) Results and Observations

The measurement results are shown in Table 8.

TABLE 8

|  |  | Absorbent body composition | Maximum tensile strength (N/25 mm) | | | Permeation rate (sec) | Surface drain rate (sec) |
| --- | --- | --- | --- | --- | --- | --- | --- |
|  |  | Mass mixing ratio (pulp:composite fiber) | Dry | Wet | Difference between dry and wet | | |
| Density-increased absorbent body | A2 | 9:1 | 3.69 | 2.17 | 1.52 | 4.54 | 15.34 |
| | A3 | 8:2 | 8.9 | 5.77 | 3.13 | 4.84 | 17.22 |
| | A4 | 6.5:3.5 | 19.37 | 14.75 | 4.62 | 5.52 | 17.95 |
| | A5 | 5:5 | 35.59 | 31.03 | 4.56 | 5.27 | 31.18 |
| | A6 | 3.5:6.5 | 63.22 | 49.36 | 13.86 | 7.73 | ≥300 |
| | A7 | 2:8 | 81.11 | 79.36 | 1.75 | 10.03 | ≥300 |
| | A8 | 0:10 | 130.39 | 125.94 | 4.45 | 10.33 | ≥300 |
| | B1 | 10:0 | 0.375 | 0.01 | 0.37 | — | — |
| | B2 | 9:1 | 0.77 | 0.57 | 0.20 | 4.59 | 16.87 |
| | B3 | 8:2 | 3.67 | 3.08 | 0.59 | 4.89 | 30.98 |
| | B4 | 6.5:3.5 | 8.24 | 7.34 | 0.90 | 5.28 | 40.56 |
| | B5 | 5:5 | 17.6 | 16.3 | 1.30 | 8.25 | ≥300 |
| | B6 | 3.5:6.5 | 29.31 | 27.25 | 2.06 | 9.13 | ≥300 |
| | B7 | 2:8 | 43.73 | 40.10 | 3.63 | 9.82 | ≥300 |
| | B8 | 0:10 | 68.66 | 62.36 | 6.30 | 4.33 | 14.82 |

The following observations are made based on Table 8.

When the mass mixing ratio of composite fibers A with respect to pulp (composite fibers A/pulp) was within the range of 1/9 to 5/5 (density-increased absorbent bodies A2 to A5), the absorption properties were adequate, but when the mass mixing ratio of composite fibers A with respect to pulp (composite fibers A/pulp) was 6.5/3.5 or greater (density-increased absorbent bodies A6 to A8), the absorption property was significantly reduced.

For the density-increased absorbent bodies A, a mass mixing ratio of lower than 1/9 for the composite fibers A with respect to the pulp (composite fibers A/pulp) is expected to result in a wet maximum tensile strength of less than 2 N/25 mm, which may make it impossible to guarantee strength when wet. From the viewpoint of ensuring strength for density-increased absorbent bodies A, therefore, the mass mixing ratio of the composite fibers A with respect to the pulp (composite fibers A/pulp) is preferably at least 1/9.

For density-increased absorbent bodies B, a mass mixing ratio of lower than 2/8 for the composite fibers B with respect to the pulp (composite fibers B/pulp) is expected to result in a wet maximum tensile strength of less than 2 N/25 mm, which may make it impossible to guarantee strength when wet. From the viewpoint of ensuring strength for density-increased absorbent bodies B, therefore, the mass mixing ratio of the composite fibers B with respect to the pulp (composite fibers B/pulp) is preferably at least 2/8.

When the density of the absorbent body is approximately 0.08 g/cm$^3$ (0.0793 to 0.0817 g/cm$^3$), the absorbent body can have both sufficient strength and absorption properties if the mass mixing ratio of the composite fibers A with respect to pulp (composite fibers A/pulp) is in the range of 1/9 to 5/5. This is because the composite fibers A can guarantee strength for the absorbent body even when present in a smaller amount than the composite fibers B (which avoids inhibiting the absorption property).

Test Example 5

The optimal range for the mass mixing ratio of the composite fibers A with respect to pulp was investigated from the viewpoint of strength and absorption property, for a system according to Test Example 4, with the density fixed at approximately 0.08 g/cm$^3$ (0.0793 to 0.0817 g/cm$^3$).

In this test example, the optimal range for the density was investigated from the viewpoint of the absorption property.

Using a blended layer of pulp (NB416 by Warehouser) and composite fibers A in the mass ratio shown in Table 9 (basis weight: 200 g/m$^2$), density-increased absorbent bodies 1 to 9 were produced with different densities (0.05, 0.06, 0.07, 0.08, 0.09, 0.1, 0.12, 0.13, 0.14 g/cm$^3$), and their absorption properties (liquid drain times) measured, in the same manner as Test Example 4.

The measurement results are shown in Table 9.

TABLE 9

|  |  | Mass mixing ratio (pulp:composite fiber A) | Density (g/cm$^3$) | | | | | | | | |
| --- | --- | --- | --- | --- | --- | --- | --- | --- | --- | --- | --- |
|  |  |  | 0.05 | 0.06 | 0.07 | 0.08 | 0.09 | 0.1 | 0.12 | 0.13 | 0.14 |
| Density-increased absorbent body | 1 | 9:1 | 300 | 32.91 | 21.22 | 16.55 | 16.73 | 16.89 | 19.64 | 25 | 27 |
| | 2 | 8:2 | 300 | 36.98 | 23.06 | 17.05 | 17.22 | 17.82 | 21.29 | 29 | 32 |
| | 3 | 6.5:3.5 | 300 | 40.75 | 25.31 | 17.58 | 17.95 | 19.45 | 25.28 | 49.3 | 55.19 |
| | 4 | 5:5 | 300 | 50.81 | 35.46 | 30.79 | 31.18 | 45.66 | 58.36 | 70 | 85 |
| | 5 | 4:6 | 300 | 250 | 250 | 250 | 250 | 250 | 250 | 300 | 300 |
| | 6 | 3.5:6.5 | 300 | 300 | 300 | 300 | 300 | 300 | 300 | 300 | 300 |
| | 7 | 2:8 | 300 | 300 | 300 | 300 | 300 | 300 | 300 | 300 | 300 |
| | 8 | 0:10 | 300 | 300 | 300 | 300 | 300 | 300 | 300 | 300 | 300 |
| | 9 | 10:0 | 250 | 20.33 | 15.11 | 14.72 | 14.82 | 15.21 | 14.53 | 13.77 | 15.48 |

The following observations are made based on Table 9.

When the mass mixing ratio of the composite fibers A with respect to pulp (composite fibers A/pulp) is in the range of 1/9 to 5/5, the density range in which sufficient liquid drain performance (specifically, the liquid drain time after dropping 3 cc of artificial menstrual blood is no longer than 90 seconds) is 0.06 to 0.14 g/cm$^3$.

If the density is below 0.06 g/cm$^3$, the liquid drain time exceeds 90 seconds for all mass mixing ratios. It is believed that when the density is below 0.06 g/cm$^3$, the distance between fibers increases and capillary force no longer acts.

If the mass mixing ratio of the composite fibers A with respect to pulp (composite fibers A/pulp) is in the range of 1/9 to 3.5/6.5 when the density is greater than 0.12 g/cm$^3$, the liquid drain time is within 60 seconds, but it exceeds 60 seconds if it is outside of this range. If the density is greater than 0.12 g/cm$^3$, capillary action will take place but the liquid mobility space will decrease, resulting in increased resistance to liquid mobility and thus reduced liquid drain performance.

These test examples suggest that the optimal range for the mass mixing ratio of composite fibers A with respect to pulp (composite fibers A/pulp) is 1/9 to 5/5, and the optimal density is 0.06 to 0.14 g/cm$^3$.

Test Example 6

(1) Method of Measuring the Embossed Section Bonding Strength (N/25 mm) Under Standard Conditions (Temperature 20° C., Relative Humidity 50%)

Each of the absorbent articles A1 to A5 and B2 to B5 produced in Production Example 2 was cut perpendicular to the embossed section to create ten sample pieces (50 mm length×25 mm width). Five of the sample pieces were coated with PANACET 810S (see Test Example 7) as a compound of a blood slipping agent (basis weight: 5 g/m$^2$), and five of the sample pieces were not coated with a blood slipping agent.

Each sample piece was used for measurement of the embossed section bonding strength (N/25 mm) after storage for at least 24 hours at a temperature of 20° C. and a relative humidity of 50%. The measurement was carried out in indoors at a temperature of 20° C. and a relative humidity of 50%.

[Dry Embossed Section Bonding Strength (N/25 mm)]

The sample piece was mounted in a tensile tester (AG-1kNI by Shimadzu Corp.) with a grip spacing of 20 mm, and with the absorbent body on the upper grip and the nonwoven fabric on the lower grip. A load (maximum point load) was applied at a pull rate of 100 mm/min until complete detachment of the nonwoven fabric and absorbent body, and the bonding strength (N) of the embossed sections per 25 mm width of the sample piece was measured using the lengthwise direction of the sample piece as the direction of tension.

[Wet Embossed Section Bonding Strength (N/25 mm)]

The bonding strength (N) of the embossed sections per 25 mm width of the sample piece was measured in the same manner as above, using the lengthwise direction of the sample piece as the direction of tension, after dipping the sample piece in ion-exchanged water until it sunk under its own weight, or after immersing the sample piece in water for 1 hour or longer.

Any measuring conditions not specified for measurement of the dry and wet embossed section bonding strengths were the measuring conditions described in ISO 9073-3 or JIS L 1913 6.3.

(2) Method of Measuring Embossed Section Bonding Strength (N/25 mm) after Accelerated Aging Test After preparing sample pieces coated with a blood slipping agent and sample pieces not coated with a blood slipping agent, similar to (1) above, each sample piece was supplied to an accelerated aging test by storage for 4 weeks at a temperature of 50° C. and a relative humidity of 0%. After the accelerated aging test, each sample piece was used for measurement of the embossed section bonding strength (N/25 mm) after storage for at least 24 hours at a temperature of 20° C. and a relative humidity of 50%. Measurements of the dry embossed section bonding strength (N/25 mm) and the wet embossed section bonding strength (N/25 mm) were carried out in the same manner as (1) above, indoors at a temperature of 20° C. and a relative humidity of 50%.

(3) Results and Observations

The measurement results are shown in Table 10.

TABLE 10

| | | Absorbent body composition | Embossed section bonding strength under standard conditions (N/25 mm) | | | | Embossed section bonding strength after accelerated aging test (N/25 mm) | | | |
|---|---|---|---|---|---|---|---|---|---|---|
| | | Mass mixing ratio (pulp:composite | Without blood slipping agent | | With blood slipping agent | | Without blood slipping agent | | With blood slipping agent | |
| | | fiber A) | Dry | Wet | Dry | Wet | Dry | Wet | Dry | Wet |
| Absorbent article | A1 | 9.5:0.5 | 1.51 | 0.94 | 0.97 | 0.35 | 1.49 | 0.91 | 0.77 | 0.24 |
| | A2 | 9:1 | 2.35 | 1.22 | 1.34 | 0.95 | 2.19 | 1.19 | 1.18 | 0.74 |
| | A3 | 8:2 | 4.12 | 3.33 | 3.23 | 2.14 | 3.68 | 3.03 | 2.38 | 1.40 |
| | A4 | 6.5:3.5 | 5.43 | 4.17 | 4.98 | 3.54 | 5.15 | 4.05 | 4.48 | 3.98 |
| | A5 | 5:5 | 7.65 | 5.34 | 5.14 | 4.18 | 7.21 | 4.11 | 4.98 | 4.09 |
| | B2 | 9:1 | 1.42 | 0.83 | 1.10 | 0.67 | 1.34 | 0.83 | 0.89 | 0.61 |
| | B3 | 8:2 | 3.20 | 1.92 | 2.25 | 1.44 | 3.31 | 1.86 | 1.86 | 1.69 |
| | B4 | 6.5:3.5 | 4.37 | 3.22 | 3.39 | 3.07 | 4.11 | 3.05 | 2.85 | 2.22 |
| | B5 | 5:5 | 4.58 | 3.86 | 3.69 | 3.24 | 4.27 | 3.27 | 3.02 | 2.43 |

The following observations are made based on Table 10.

The embossed section bonding strengths were reduced by the presence of a blood slipping agent, both after testing under standard conditions and in an accelerated aging test. Because of this, it is thought that the adhesive force of the HMA is reduced by mixing of the oil component of the blood slipping agent and the oil component of the HMA. This suggests that the embossed section bonding strength is reduced more after the accelerated aging test, compared to after standard conditions.

Absorbent articles A2 to A5 have embossed section bonding strengths of 0.75 N/25 mm or greater under standard conditions, both when dry and when wet, even in the presence of a blood slipping agent, and can therefore prevent interfacial peeling between the top sheet and absorbent body that can potentially occur during use of absorbent articles. Thus, even when the top sheet has been coated with a blood slipping agent, it is advantageous for the mass mixing ratio of the composite fibers A with respect to the pulp in the absorbent body to be at least 1/9 from the viewpoint of increasing the dry and wet embossed section bonding strengths, which makes it possible to obtain a dry embossed section bonding strength of 1.34 N/25 mm or greater and a wet embossed section bonding strength of 0.95 N/or greater.

Furthermore, when comparing the absorbent articles having identical mass mixing ratios of composite fibers A and B with respect to pulp in the absorbent bodies (that is, A2 and B2, A3 and B3, A4 and B4, and A5 and B5), the dry and wet embossed section bonding strengths were greater with absorbent articles A than with absorbent articles B at all mass mixing ratios, regardless of the presence of a blood slipping agent. Thus, when the mass mixing ratios of composite fibers A and B with respect to the pulp in the absorbent body are the same, the dry and wet embossed section bonding strengths can be increased more when using composite fibers A than when using composite fibers B. Furthermore, when given dry and wet embossed section bonding strengths have been obtained, it is possible obtain a lower mass mixing ratio of composite fiber with respect to pulp in the absorbent body when using composite fibers A than when using composite fibers B (that is, the mass mixing ratio of pulp is greater, allowing the absorption performance of the absorbent body to be increased).

Test Example 7

The blood slipping agents used for the test examples are listed below.
[($a_1$) Ester of a Chain Hydrocarbon Tetraol and at Least One Fatty Acid]
UNISTAR H-408BRS, product of NOF Corp.
Pentaerythritol tetra(2-ethylhexanoate), weight-average molecular weight: approximately 640
UNISTAR H-2408BRS-22, product of NOF Corp.
Mixture of pentaerythritol tetra(2-ethylhexanoate) and neopentylglycol di(2-ethylhexanoate) (58:42 as weight ratio), weight-average molecular weight: approximately 520
[($a_2$) Ester of a Chain Hydrocarbon Triol and at Least One Fatty Acid]
Cetiol SB45DEO, Cognis Japan
Glycerin and fatty acid triester, with oleic acid or stearylic acid as the fatty acid.
SOY42, product of NOF Corp.
Glycerin and fatty acid triester with $C_{14}$ fatty acid: $C_{16}$ fatty acid: $C_{18}$ fatty acid:$C_{20}$ fatty acid (including both saturated fatty acids and unsaturated fatty acids) at a mass ratio of about 0.2:11:88:0.8, weight-average molecular weight: 880
Tri-C2L oil fatty acid glyceride, product of NOF Corp.
Glycerin and fatty acid triester with $C_8$ fatty acid:$C_{10}$ fatty acid:$C_{12}$ fatty acid at a weight ratio of about 37:7:56, weight-average molecular weight: approximately 570
Tri-CL oil fatty acid glyceride, product of NOF Corp.
Glycerin and fatty acid triester with $C_8$ fatty acid:$C_{12}$ fatty acid at a weight ratio of about 44:56, weight-average molecular weight: approximately 570
PANACET 810s, product of NOF Corp.
Glycerin and fatty acid triester with $C_8$ fatty acid:$C_{10}$ fatty acid at a weight ratio of about 85:15, weight-average molecular weight: approximately 480
PANACET 800, product of NOF Corp.
Glycerin and fatty acid triester with octanoic acid ($C_8$) as the entire fatty acid portion, weight-average molecular weight: approximately 470
PANACET 800B, product of NOF Corp.
Glycerin and fatty acid triester with 2-ethylhexanoic acid ($C_8$) as the entire fatty acid portion, weight-average molecular weight: approximately 470
NA36, product of NOF Corp.
Glycerin and fatty acid triester with $C_{16}$ fatty acid:$C_{18}$ fatty acid:$C_{20}$ fatty acid (including both saturated fatty acids and unsaturated fatty acids) at a weight ratio of about 5:92:3, weight-average molecular weight: approximately 880
Tri-coconut fatty acid glyceride, product of NOF Corp.
Glycerin and fatty acid triester with $C_8$ fatty acid:$C_{10}$ fatty acid:$C_{12}$ fatty acid: $C_{14}$ fatty acid:$C_{16}$ fatty acid (including both saturated fatty acids and unsaturated fatty acids) at a weight ratio of about 4:8:60:25:3, weight-average molecular weight: 670
Caprylic acid diglyceride, product of NOF Corp.
Glycerin and fatty acid diester with octanoic acid as the fatty acid, weight-average molecular weight: approximately 340
[($a_3$) Ester of a Chain Hydrocarbon Diol and at Least One Fatty Acid]
UNISTAR H-208BRS, product of NOF Corp.
Neopentyl glycol di(2-ethylhexanoate), weight-average molecular weight: approximately 360
COMPOL BL, product of NOF Corp.
Dodecanoic acid ($C_{12}$) monoester of butylene glycol, weight-average molecular weight: approximately 270
COMPOL BS, product of NOF Corp.
Octadecanoic acid ($C_{18}$) monoester of butylene glycol, weight-average molecular weight: approximately 350
[($c_2$) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]
Tributyl O-acetylcitrate, product of Tokyo Kasei Kogyo Co., Ltd.
Weight-average molecular weight: approximately 400
Tributyl citrate, product of Tokyo Kasei Kogyo Co., Ltd.
Weight-average molecular weight: approximately 360
[($c_3$) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]
Dioctyl adipate, product of Wako Pure Chemical Industries, Ltd.
Weight-average molecular weight: approximately 380
[($d_3$) Ester of a Fatty Acid and an Aliphatic Monohydric Alcohol]

ELECTOL WE20, product of NOF Corp.
Ester of dodecanoic acid ($C_{12}$) and dodecyl alcohol ($C_{12}$), weight-average molecular weight: approximately 360
ELECTOL WE40, product of NOF Corp.
Ester of tetradecanoic acid ($C_{14}$) and dodecyl alcohol ($C_{12}$), weight-average molecular weight: approximately 390
[($e_1$) Polyoxy $C_3$-$C_6$ Alkylene Glycol]
UNIOL PB500, product of NOF Corp.
Polybutylene glycol, weight-average molecular weight: approximately 500
UNIOL PB700, product of NOF Corp.
Polyoxybutylene polyoxypropylene glycol, weight-average molecular weight: approximately 700
[($f_1$) Chain Alkane]
PARLEAM 6, product of NOF Corp.
Branched chain hydrocarbon, produced by copolymerization of liquid isoparaffin, isobutene and n-butene followed by hydrogen addition, polymerization degree: approximately 5-10, weight-average molecular weight: approximately 330

[Other Materials]
NA50, product of NOF Corp.
Glycerin and fatty acid triester obtained by addition of hydrogen to NA36 for reduced proportion of double bonds from unsaturated fatty acid starting material, weight-average molecular weight: approximately 880
(Caprylic acid/capric acid) monoglyceride, product of NOF Corp.
Glycerin and fatty acid monoester, with octanoic acid ($C_8$) and decanoic acid ($C_{10}$) at a weight ratio of about 85:15, weight-average molecular weight: approximately 220
Monomuls 90-L2 lauric acid monoglyceride, product of Cognis Japan
Isopropyl citrate, product of Tokyo Kasei Kogyo Co., Ltd. Weight-average molecular weight: approximately 230
Diisostearyl malate
Weight-average molecular weight: approximately 640
UNIOL PB1000R, product of NOF Corp.
Polybutylene glycol, weight-average molecular weight: approximately 1,000
UNIOL D-250, product of NOF Corp.
Polypropylene glycol, weight-average molecular weight: approximately 250
UNIOL D-400, product of NOF Corp.
Polypropylene glycol, weight-average molecular weight: approximately 400
UNIOL D-700, product of NOF Corp.
Polypropylene glycol, weight-average molecular weight: approximately 700
UNIOL D-1000, product of NOF Corp.
Polypropylene glycol, weight-average molecular weight: approximately 1,000
UNIOL D-1200, product of NOF Corp.
Polypropylene glycol, weight-average molecular weight: approximately 1,160
UNIOL D-2000, product of NOF Corp.
Polypropylene glycol, weight-average molecular weight: approximately 2,030
UNIOL D-3000, product of NOF Corp.
Polypropylene glycol, weight-average molecular weight: approximately 3,000
UNIOL D-4000, product of NOF Corp.
Polypropylene glycol, weight-average molecular weight: approximately 4,000
PEG1500, product of NOF Corp.
Polyethylene glycol, weight-average molecular weight: approximately 1,500-1,600
WILBRITE cp9, product of NOF Corp.
Polybutylene glycol compound with OH groups at both ends esterified by hexadecanoic acid ($C_{16}$), weight-average molecular weight: approximately 1,150
UNILUBE MS-70K, product of NOF Corp.
Stearyl ether of polypropylene glycol, approximately 15 repeating units, weight-average molecular weight: approximately 1,140
NONION S-6, product of NOF Corp.
Polyoxyethylene monostearate, approximately 7 repeating units, weight-average molecular weight: approximately 880
UNILUBE 5TP-300 KB
Polyoxyethylenepolyoxypropylene pentaerythritol ether, produced by addition of 5 mol of ethylene oxide and 65 mol of propylene oxide to 1 mol of pentaerythritol, weight-average molecular weight: 4,130
WILBRITE s753, product of NOF Corp.
Polyoxyethylenepolyoxypropylene polyoxybutylene glycerin, weight-average molecular weight: approximately 960
UNIOL TG-330, product of NOF Corp.
Glyceryl ether of polypropylene glycol, approximately 6 repeating units, weight-average molecular weight: approximately 330
UNIOL TG-1000, product of NOF Corp.
Glyceryl ether of polypropylene glycol, approximately 16 repeating units, weight-average molecular weight: approximately 1,000
UNIOL TG-3000, product of NOF Corp.
Glyceryl ether of polypropylene glycol, approximately 16 repeating units, weight-average molecular weight: approximately 3,000
UNIOL TG-4000, product of NOF Corp.
Glyceryl ether of polypropylene glycol, approximately 16 repeating units, weight-average molecular weight: approximately 4,000
UNILUBE DGP-700, product of NOF Corp.
Diglyceryl ether of polypropylene glycol, approximately 9 repeating units, weight-average molecular weight: approximately 700
UNIOX HC60, product of NOF Corp.
Polyoxyethylene hydrogenated castor oil, weight-average molecular weight: approximately 3,570
Vaseline, product of Cognis Japan
Petroleum-derived hydrocarbon, semi-solid Test Example 7-1

Menstrual Blood Surface Residue Rate A, with Absorption of Large Amount of Blood A test was conducted to evaluate the absorption property of a sanitary napkin after one-time absorption of a large amount of blood.
There were prepared a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150 to 450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The top sheet was a top sheet produced by the method described in Japanese Unexamined Patent Publication No. 2008-2034, having a ridge-furrow structure, with a ridge thickness of approximately 1.5 mm and a furrow thickness of approximately 0.4 mm, and the pitch of the ridge-furrow structure (ridge width+furrow width) was approximately 4 mm and open holes were formed in the furrows at an open area of approximately 15%.

UNISTAR H-408BRS (product of NOF Corp., tetraester of pentaerythritol and fatty acid) was selected as the blood slipping agent, and it was coated onto the skin contact surface (ridge-furrow side) of the top sheet from a control seam HMA gun at room temperature, to a basis weight of 5.0 g/m². With an electron microscope it was confirmed that the H-408BRS was adhering onto the fiber surfaces as fine particulates.

A back sheet, an absorbent body, a second sheet, and a top sheet with the ridge-furrow side facing upward, were stacked in that order to form sanitary napkin No. 1-1.

Sanitary napkins No. 1-2 to No. 1-49 were produced, changing the blood slipping agent from UNISTAR H-408BRS to the ones listed in Table 11. Each blood slipping agent was used directly, when it was liquid at room temperature, or when the blood slipping agent was solid at room temperature it was heated to its melting point +20° C., and then a control seam HMA gun was used for atomization of the blood slipping agent and coating onto the skin contact surface of the top sheet to a basis weight of about 5 g/m².

The blood slipping agent was coated onto essentially the entire skin contact surface of the top sheet, and on both the ridges and furrows.

[Test Methods]

After measuring the mass $W_2$ (g) of the top sheet (the mass of the top sheet before the test), an acrylic board with an opened hole (200 mm×100 mm, 125 g, with a 40 mm×10 mm hole opened at the center) was placed on the top sheet, at the center section in the lengthwise direction and widthwise direction of the absorbent article, and 4.0 g of horse EDTA blood at 37±1° C. (obtained by adding ethylenediaminetetraacetic acid (hereunder, "EDTA") to horse blood to prevent coagulation) was dropped through the hole using a pipette.

After dropping the horse EDTA blood, the acrylic board was immediately removed, the top sheet was taken off, the mass $W_3$ (g) (mass of the top sheet after the test) was measured and the "surface residue rate A (mass %)" was calculated by the following formula.

$$\text{Surface residue rate } A \text{ (mass \%)} = 100 \times [W_3(g) - W_2(g)]/4.0(g)$$

Figure 5:
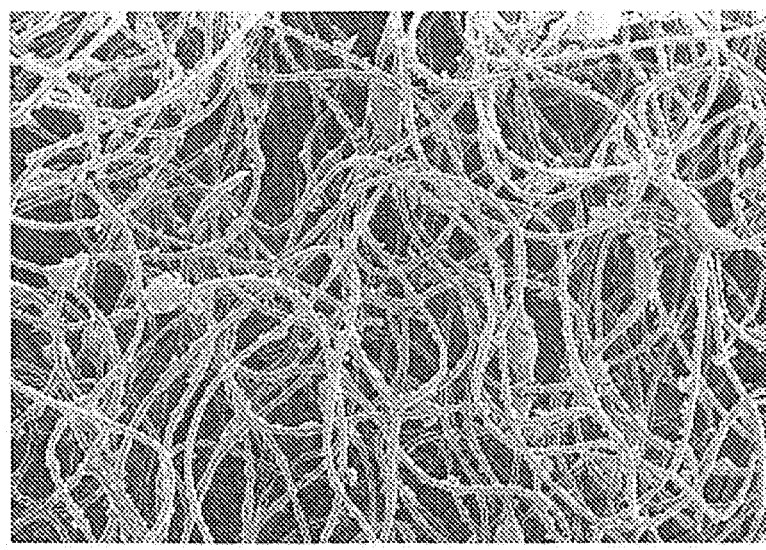
FIG. 5 is an electron micrograph of the skin contact surface of a top sheet in a sanitary napkin wherein the top sheet comprises tri-C2L oil fatty acid glycerides.

The tack on the skin contact surface of the top sheet was measured at 35° C., and evaluated on the following scale.
G: No tack
F: Slight tack
P: Tack The surface residue rate A and tack of each absorbent article, and the properties of each blood slipping agent, are shown below in Table 11. FIG. 5 is an electron micrograph of the skin contact surface of a top sheet in a sanitary napkin wherein the top sheet comprises tri-C2L oil fatty acid glycerides.

TABLE 11

| No. | Blood slipping agent | Kinematic viscosity (mm²/s, 40° C.) | Water holding percentage (mass %) | Weight-average molecular weight | IOB | Melting point (° C.) | Surface residue rate A (mass %) | Tack |
|---|---|---|---|---|---|---|---|---|
| 1-1 | H-408 BRS | 45 | 0.7 | 640 | 0.13 | <−5 | 0.8 | G |
| 1-2 | H-2408 BRS-22 | 22 | 0.8 | 520 | 0.18 | <−5 | 0.8 | G |
| 1-3 | Tri-C2L oil fatty acid glyceride | 20 | <1.0 | 570 | 0.27 | 37 | | G |
| 1-4 | Tri-CL oil fatty acid glyceride | 15 | <1.0 | 570 | 0.28 | 38 | | G |
| 1-5 | PANACET 810s | 9 | 0.3 | 480 | 0.32 | −5 | 0.8 | G |
| 1-6 | PANACET 800 | 15 | 0.5 | 470 | 0.33 | −5 | 1.8 | G |
| 1-7 | PANACET 800B | 20 | <1.0 | 470 | 0.33 | −5 | | G |
| 1-8 | NA36 | 40 | <1.0 | 880 | 0.16 | 37 | | G |
| 1-9 | Tri-coconut oil fatty acid glyceride | 25 | <1.0 | 670 | 0.28 | 30 | | G |
| 1-10 | Caprylic acid diglyceride | 25 | 2.7 | 340 | 0.58 | <45 | 1.0 | G |
| 1-11 | UNISTAR H-208 BRS | 8 | 0.7 | 360 | 0.24 | <−5 | 0.5 | G |
| 1-12 | COMPOL BL | 10 | 1.6 | 270 | 0.50 | 2 | 1.3 | G |
| 1-13 | COMPOL BS | 35 | 0.3 | 350 | 0.36 | 37 | 2.5 | G |
| 1-14 | Tributyl O-acetylcitrate | 15 | 0.9 | 400 | 0.60 | <45 | 0.5 | G |
| 1-15 | Tributyl citrate | 12 | 0.6 | 360 | 0.78 | <45 | 1.8 | G |
| 1-16 | Dioctyl adipate | 7 | 0.4 | 380 | 0.27 | <45 | 1.5 | G |
| 1-17 | ELECTOL WE20 | 10 | 0.3 | 360 | 0.13 | 29 | 0.5 | G |
| 1-18 | ELECTOL WE40 | 15 | 0.5 | 390 | 0.12 | 37 | 2.3 | G |
| 1-19 | UNIOL PB500 | 40 | 3.6 | 500 | 0.44 | <45 | 2.5 | G |
| 1-20 | UNIOL PB700 | 50 | 2.3 | 700 | 0.49 | −5 | 1.3 | G |
| 1-21 | PARLEAM 6 | 5 | 0.06 | 330 | 0.00 | −5 | 2.0 | G |
| 1-22 | NA50 | 80<< | — | 880 | 0.18 | 52 | 4.3 | G |
| 1-23 | (Caprylic acid/capric acid) monoglyceride | 70 | 4.0<< | 220 | 1.15 | <45 | 5.0 | G |
| 1-24 | 90-L2 lauric acid monoglyceride | 80<< | 4.0<< | <1,000 | 0.87 | 58 | 5.0 | G |
| 1-25 | Isopropyl citrate | 120 | 4.0<< | 230 | 1.56 | <45 | 4.8 | F |
| 1-26 | Diisostearyl malate | 450 | 4.0<< | 640 | 0.28 | <45 | 3.3 | F |
| 1-27 | UNIOL PB1000R | 70 | 5.5 | 1000 | 0.40 | <45 | 2.5 | F |
| 1-28 | UNIOL D-250 | 20 | 4.0<< | 250 | | <45 | 3.8 | G |

TABLE 11-continued

| No. | Blood slipping agent | Kinematic viscosity (mm²/s, 40° C.) | Water holding percentage (mass %) | Weight-average molecular weight | IOB | Melting point (° C.) | Surface residue rate A (mass %) | Tack |
|---|---|---|---|---|---|---|---|---|
| 1-29 | UNIOL D-400 | 30 | 4.0<< | 400 | 0.76 | <45 | 4.8 | G |
| 1-30 | UNIOL D-700 | 50 | 34.6 | 700 | 0.58 | <45 | 4.8 | G |
| 1-31 | UNIOL D-1000 | 70 | 26.7 | 1,000 | 0.51 | <45 | 3.8 | F |
| 1-32 | UNIOL D-1200 | 90 | 16.2 | 1,160 | 0.48 | <45 | 3.0 | F |
| 1-33 | UNIOL D-2000 | 160 | | 2,030 | | <45 | | P |
| 1-34 | UNIOL D-3000 | | 0.6 | 3,000 | 0.39 | <45 | 3.0 | P |
| 1-35 | UNIOL D-4000 | 450 | 0.5 | 4,000 | 0.38 | <45 | 2.5 | P |
| 1-36 | PEG 1500 | 120 | 4.0<< | 1,500-1,600 | 0.78 | 40 | 5.5 | P |
| 1-37 | WILBRITE CP9 | 120 | 0.6 | 1,150 | 0.21 | 35 | 6.8 | P |
| 1-38 | UNILUBE MS-70K | 50 | 2.8 | 1,140 | 0.30 | <−10 | 1.5 | F |
| 1-39 | NONION S-6 | 65 | 4.0<< | 880 | 0.44 | 37 | | G |
| 1-40 | UNILUBE 5TP-300KB | 310 | 3.9 | 4,130 | 0.39 | <45 | 2.0 | P |
| 1-41 | WILBRITE s753 | 120 | 27.3 | 960 | 0.67 | −5 | 3.5 | F |
| 1-42 | UNIOL TG-330 | 30 | | 330 | 1.27 | <45 | | G |
| 1-43 | UNIOL TG-1000 | 100 | 21.2 | 1,000 | 0.61 | <45 | 3.5 | G |
| 1-44 | UNIOL TG-3000 | 230 | 4.3 | 3,000 | 0.42 | <45 | 1.0 | P |
| 1-45 | UNIOL TG-4000 | 300 | 2.4 | 4,000 | 0.40 | <45 | 2.0 | P |
| 1-46 | UNILUBE DGP-700 | 200 | 4.0<< | 700 | 0.91 | <0 | 3.5 | F |
| 1-47 | UNIOX HC60 | 1150 | | 3,570 | 0.46 | 33 | | P |
| 1-48 | Vaseline | 80<< | 0.0 | <1,000 | 0.00 | 55 | 4.0 | P |
| 1-49 | None | — | — | — | — | — | 7.5 | G |

*High viscosity, unmeasurable.

With sanitary napkin No. 1-49, which had no blood slipping agent, the surface residue rate A was 7.5 mass %, but with sanitary napkins No. 1-1 to No. 1-21 wherein the kinematic viscosity and water holding percentage were within the prescribed ranges, the surface residue rate A was 2.5 mass % or lower.

With sanitary napkins No. 1-1 to No. 1-21, it was observed that the horse EDTA blood that was dropped onto the ridges of the top sheet slid down from the ridges into the furrows, and was rapidly absorbed from the furrows into the absorbent body. However, with sanitary napkin No. 1-49 which had no blood slipping agent, the dropped horse EDTA blood did not slip down into the furrows but slowly dripped down into the furrows, most of it remaining on the ridges of the top sheet. Also, with the absorbent articles with high a water holding percentage, as with No. 1-30, for example, the horse EDTA blood that was dropped onto the ridges of the top sheet did not slip down into the furrows but slowly dripped while partially remaining on the top sheet, and a portion thereof remained on the ridges.

This suggests that sanitary napkins No. 1-1 to No. 1-21 allow rapid migration of menstrual blood from the top sheet into the absorbent body, when a large amount of menstrual blood has reached the top sheet at once.

Next, several volunteer subjects were asked to wear sanitary napkins Nos. 1-1 to 1-49, and most of the obtained responses indicated that with the sanitary napkins comprising blood slipping agents Nos. 1-1 to 1-21, the top sheets had no sticky feel and the top sheets were smooth, even after absorption of menstrual blood.

Test Example 7-2

Menstrual Blood Surface Residue Rate B, with Absorption of Small Amount of Blood A test was conducted to evaluate the absorption property of a sanitary napkin after absorption of a small amount of blood.

There were prepared a top sheet, formed of a hydrophilic agent-treated air-through nonwoven fabric (composite fiber composed of polyester and polyethylene terephthalate, basis weight: 35 g/m²) (hereunder also referred to as "top sheet with ridge-furrows"), a second sheet formed of an air-through nonwoven fabric (composite fibers composed of polyester and polyethylene terephthalate, basis weight: 30 g/m²), an absorbent body comprising pulp (basis weight: 150 to 450 g/m², increased at the center section), an acrylic super-absorbent polymer (basis weight: 15 g/m²) and tissue as a core wrap, a water-repellent agent-treated side sheet, and a back sheet composed of a polyethylene film.

The top sheet was a top sheet produced by the method described in Japanese Unexamined Patent Publication No. 2008-2034, having a ridge-furrow structure, with a ridge thickness of approximately 1.5 mm and a furrow thickness of approximately 0.4 mm, and the pitch of the ridge-furrow structure (ridge width+furrow width) was approximately 4 mm and open holes were formed in the furrows at an open area of approximately 15%.

UNISTAR H-408BRS (product of NOF Corp., tetraester of pentaerythritol and fatty acid) was selected as the blood slipping agent, and it was coated onto the skin contact surface (ridge-furrow side) of the top sheet from a control seam HMA gun at room temperature, to a basis weight of 5.0 g/m². With an electron microscope it was confirmed that the H-408BRS was adhering onto the fiber surfaces as fine particulates.

A back sheet, an absorbent body, a second sheet, and a top sheet with the ridge-furrow side facing upward, were stacked in that order to form sanitary napkin No. 2-1(i).

A sanitary napkin No. 2-1(ii) was formed in the same manner as the sanitary napkin No. 2-1(i), except that the top sheet was changed to a top sheet formed of a flat hydrophilic agent-treated air-through nonwoven fabric (composite fiber composed of polyester and polyethylene terephthalate, basis weight: 35 g/m²), without a ridge-furrow structure (hereunder also referred to as "flat top sheet").

Sanitary napkins No. 2-2(i) to No. 2-11(i) and No. 2-2(ii) to No. 2-11(ii) were produced, changing the blood slipping agent from UNISTAR H-408BRS to the ones listed in Table 12. Each blood slipping agent was used directly, when it was liquid at room temperature, or when the blood slipping agent was solid at room temperature it was heated to its melting point +20° C., and then a control seam HMA gun was used for atomization of the blood slipping agent and coating onto the skin contact surface of the top sheet to a basis weight of about 5 g/m².

The blood slipping agent was coated over essentially the entire skin contact surface of the top sheet, and on both the ridges and furrows of the top sheets with a ridge-furrow structure.

[Test Methods]

After measuring the mass $W_4$ (g) of the top sheet (the mass of the top sheet before the test), approximately 0.25 g (2 drops) of horse EDTA blood at 37±1° C. was added dropwise through a pipette, on the top sheet at the center in the lengthwise direction and widthwise direction of the absorbent article. The horse EDTA blood was dropped onto the top parts of the ridges, in the top sheets with ridge-furrows.

At 30 seconds after dropping, the top sheet was taken off, the mass $W_5$ (g) (mass of top sheet after the test) was measured and the "surface residue rate B (mass %)" was calculated by the following formula.

Surface residue rate $B$ (mass %)=100×($W_5$(g)−$W_4$(g))/$W_6$(g)

$W_6$ (g) is the mass of the dropped horse EDTA blood, calculated from the mass of the pipette before and after dropping.

The results are shown in Table 12 below.

TABLE 12

| No. | Blood slipping agent | Surface residue rate B (mass %) | |
| --- | --- | --- | --- |
| | | Top sheet with ridge-furrows | Flat top sheet |
| 2-1 | H-408 BRS | 4% | 32% |
| 2-2 | PANACET 810S | 8% | 40% |
| 2-3 | Capric acid diglyceride | 8% | 24% |
| 2-4 | COMPOL BL | 4% | 32% |
| 2-5 | Tributyl O-acetylcitrate | 8% | 44% |
| 2-6 | Dioctyl adipate | 8% | 32% |
| 2-7 | ELECTOL WE40 | 8% | 24% |
| 2-8 | UNIOL PB500 | 4% | 68% |
| 2-9 | PARLEAM 6 | 4% | 100% |
| 2-10 | UNIOL D-250 | 16% | 48% |
| 2-11 | None | 28% | 28% |

Table 12 shows that when the blood slipping agent was H-408BRS, PANACET 810S, capric acid diglyceride, COMPOL BL, tributyl O-acetylcitrate, dioctyl adipate, ELECTOL WE40, UNIOL PB500 or PARLEAM 6, the surface residue rate B of the top sheet with ridge-furrows was low. This suggests that blood slipping agents having the prescribed properties cause rapid migration of small amounts of blood from the ridges to the furrows and into the absorbent body.

Test Example 7-3

Viscosity of Blood Containing Blood Slipping Agent

The viscosity of the blood slipping agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate, due to the parallel plate, but the average shear rate indicated by the device was 10 s$^{-1}$.

The viscosity of the horse defibrinated blood containing 2 mass % PANACET 810s was 5.9 mPa·s, while the viscosity of the horse defibrinated blood containing no blood slipping agent was 50.4 mPa·s. Thus, the horse defibrinated blood containing 2 mass % PANACET 810s clearly had an approximately 90% lower viscosity than the blood containing no blood slipping agent.

It is known that blood contains components, such as blood cells and has a thixotropic nature, and it is believed that the blood slipping agent of the present disclosure has an effect of lowering the viscosity of blood, such as menstrual blood in the low viscosity range. Lowering the blood viscosity presumably allows absorbed menstrual blood to more easily migrate rapidly from the top sheet to the absorbent body.

Test Example 7-4

Photomicrograph of Blood Slipping Agent-Containing Blood

Menstrual blood was sampled from healthy volunteers onto food storage wrap film, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood slipping agent is shown in FIG. 6(a), and a photomicrograph of menstrual blood containing PANACET 810s is shown in FIG. 6(b).

As shown in FIG. 6, the erythrocytes formed aggregates, including a rouleaux structure, in the menstrual blood containing no blood slipping agent, while the erythrocytes were stably dispersed in the menstrual blood containing PANACET 810s. This suggests that the blood slipping agent has the function of stabilizing erythrocytes in blood.

Test Example 7-5

Surface Tension of Blood Containing Blood Slipping Agent

The surface tension of blood containing a blood slipping agent was measured by the pendant drop method, using a Drop Master500 contact angle meter by Kyowa Interface Science Co., Ltd. The surface tension was measured after adding a prescribed amount of blood slipping agent to sheep defibrinated blood, and thoroughly shaking.

Figure 7:
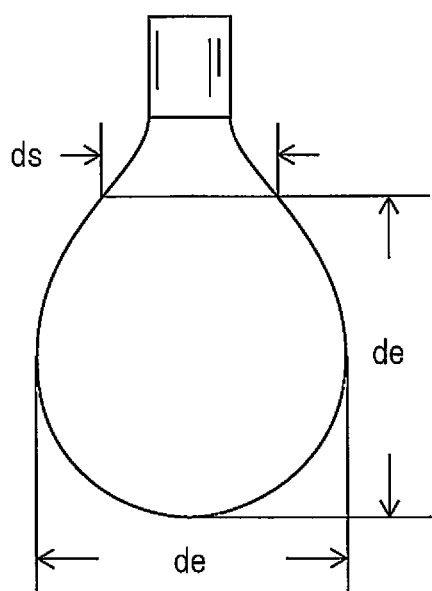
FIG. 7 is a diagram illustrating a method of measuring surface tension.

The measurement was accomplished automatically with the apparatus, and the surface tension γ was determined by the following formula (see FIG. 7).

$$\gamma = g \times \rho \times (de)^2 \times 1/H$$

g: Gravitational constant
1/H: Correction factor determined from ds/de
ρ: Density
de: Maximum diameter
ds: Diameter at location of increase by de from dropping edge The density ρ was measured at the temperatures listed in Table 13, according to JIS K 2249-1995, "Density test methods and density/mass/volume conversion tables", 5. Vibrating density test method.

The measurement was performed using a DA-505 by Kyoto Electronics Co., Ltd.

The results are shown in Table 13 below.

TABLE 13

| No. | Blood slipping agent Type | Amount (mass %) | Measuring temperature (° C.) | Surface tension (mN/m) |
|-----|---------------------------|-----------------|------------------------------|------------------------|
| 1 | — | — | 35 | 62.1 |
| 2 | PANACET 810s | 0.01 | 35 | 61.5 |
| 3 | | 0.05 | 35 | 58.2 |
| 4 | | 0.10 | 35 | 51.2 |
| 5 | ELECTOL WE20 | 0.10 | 35 | 58.8 |
| 6 | PARLEAM 6 | 0.10 | 35 | 57.5 |
| 7 | — | — | 50 | 56.3 |
| 8 | WILBRITE cp9 | 0.10 | 50 | 49.1 |

Based on Table 13 it is seen that the blood slipping agent has an effect of lowering the surface tension of blood.

Lowering the surface tension of blood presumably allows absorbed blood to rapidly migrate from the top sheet to the absorbent body without being retained between the top sheet fibers.

REFERENCE SIGNS LIST

1 Sanitary napkin (absorbent article)
2 Top sheet (liquid-permeable layer)
3 Back sheet (liquid-impermeable layer)
4 Absorbent body
5 Compressed section (joining section)

The invention claimed is:

1. An absorbent article comprising:
a liquid-permeable layer,
a liquid-impermeable layer,
an absorbent body provided between the liquid-permeable layer and the liquid-impermeable layer, and
a joining section that joins the liquid-permeable layer and the absorbent body, wherein
the absorbent body contains, as constituent fibers, cellulose-based water-absorbent fibers, and
hydrophobic thermoplastic resin fibers that include an unsaturated carboxylic acid, an unsaturated carboxylic anhydride or a mixture thereof as the monomer component,
the difference between the dry Gurley bending resistance and the wet Gurley bending resistance of the joining section is 2.5 mN/12.5 mm or less,
the joining section dry bonding strength of the joining section is 1.53 to 7.65 N/25 mm, and
the joining section wet bonding strength of the joining section is 0.95 to 4.34 N/25 mm.

2. The absorbent article according to claim 1, wherein the mass ratio of the hydrophobic thermoplastic resin fibers is 1/9 to 5/5 with respect to the water-absorbent fibers present in the absorbent body.

3. The absorbent article according to claim 2, wherein the dry Gurley bending resistance of the joining section is 4.82 to 6.09 mN/12.5 mm, and the wet Gurley bending resistance of the joining section is 2.32 to 3.98 mN/12.5 mm.

4. The absorbent article according to claim 2, wherein the density of the absorbent body is 0.06 to 0.14 g/cm$^3$.

5. The absorbent article according to claim 4, wherein the absorbent body is obtained by spraying high-pressure steam onto a mixed material comprising the cellulose-based water-absorbent fibers and the hydrophobic thermoplastic resin fibers, to increase the density.

6. The absorbent article according to claim 4, wherein the basis weight of the absorbent body is 40 to 900 g/m$^2$.

7. The absorbent article according to claim 1, wherein
the joining section includes a section extending in a lengthwise direction of the absorbent article, and
the dry Gurley bending resistance and wet Gurley bending resistance of the joining section are the dry Gurley bending resistance and wet Gurley bending resistance of the section extending in the lengthwise direction of the absorbent article.

8. The absorbent article according to claim 1, wherein the joining section is a compressed section in which the liquid-permeable layer and the absorbent body are integrated in a thickness direction of the absorbent article.

9. The absorbent article according to claim 1, wherein the constituent fibers of the absorbent body are bonded to each other.

10. The absorbent article according to claim 1, further comprising a through-hole passing through the liquid-permeable layer and having an open area of 5% to 70% of an entire area of the liquid-permeable layer.

11. The absorbent article according to claim 1, further comprising a through-hole running through the liquid-permeable layer and the absorbent body.

12. The absorbent article according to claim 1, wherein
the hydrophobic thermoplastic resin fibers are core-sheath composite fibers having as the sheath component,
a modified polyolefin that has been graft-polymerized with a vinyl monomer comprising the unsaturated carboxylic acid, unsaturated carboxylic anhydride or mixture thereof, or
a polymer blend of the modified polyolefin with another resin, and as the core component a resin with a higher melting point than the modified polyolefin.

13. The absorbent article according to claim 1, wherein the unsaturated carboxylic acid, unsaturated carboxylic anhydride or mixture thereof is maleic acid or its derivative, maleic anhydride or its derivative, or a mixture thereof.

14. The absorbent article according to claim 1, wherein the absorbent body further comprises a high-water-absorbing material other than the water-absorbent fibers.

15. The absorbent article according to claim 1, wherein the hydrophobic thermoplastic resin fibers in the absorbent body are colored.

16. The absorbent article according to claim 1, wherein
the liquid-permeable layer and the absorbent body are bonded by an adhesive,
the liquid-permeable layer includes a skin contact surface configured to contact a wearer's skin, and
the liquid-permeable layer includes a blood slipping agent having a 40° C. kinematic viscosity of 0.01 to 80 mm$^2$/s, a water holding percentage of 0.01 to 4.0 mass % and a weight-average molecular weight of less than 1,000, at least in an excretory opening contact region on the skin contact surface.

17. The absorbent article according to claim 16, wherein the blood slipping agent has an IOB (Inorganic Organic Balance) of 0.00 to 0.60.

18. The absorbent article according to claim 16, wherein the blood slipping agent is selected from the group consisting of following items (i) to (iii), and any combination thereof:

(i) a hydrocarbon;
(ii) a compound having (ii-1) a hydrocarbon moiety and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—CO—) and oxy group (—O—), inserted between a C—C single bond of the hydrocarbon moiety, and (iii-3) one or more, same or different groups selected from the group consisting of carboxyl group (—COOH) and hydroxyl group (—OH), substituting a hydrogen on the hydrocarbon moiety;

with the proviso that when two or more oxy groups are inserted in the compound of (ii) or (iii), the oxy groups are not adjacent.

19. The absorbent article according to claim 16, wherein the blood slipping agent is selected from the group consisting of following items (i') to (iii'), and any combination thereof:
(i') a hydrocarbon;
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
(iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety;

with the proviso that when two or more same or different bonds are inserted in the compound of (ii') or (iii'), the bonds are not adjacent.

20. The absorbent article according to claim 16, wherein the blood slipping agent is selected from the group consisting of following items (A) to (F), as well as any combination thereof:
(A) an ester of (A1) a compound having a chain hydrocarbon moiety and 2-4 hydroxyl groups substituting hydrogens on the chain hydrocarbon moiety, and (A2) a compound having a chain hydrocarbon moiety and one carboxyl group substituting a hydrogen on the chain hydrocarbon moiety;
(B) an ether of (B1) a compound having a chain hydrocarbon moiety and 2-4 hydroxyl groups substituting hydrogens on the chain hydrocarbon moiety, and (B2) a compound having a chain hydrocarbon moiety and one hydroxyl group substituting a hydrogen on the chain hydrocarbon moiety;
(C) an ester of (C1) a carboxylic acid, hydroxy acid, alkoxy acid or oxoacid containing a chain hydrocarbon moiety and 2-4 carboxyl groups substituting hydrogens on the chain hydrocarbon moiety, and (C2) a compound having a chain hydrocarbon moiety and one hydroxyl group substituting a hydrogen on the chain hydrocarbon moiety;
(D) a compound having a chain hydrocarbon moiety, and one bond selected from the group consisting of ether bond (—O—), carbonyl bond (—CO—), ester bond (—COO—) and carbonate bond (—OCOO—), inserted between a C—C single bond of the chain hydrocarbon moiety;
(E) a polyoxy $C_3$-$C_6$ alkylene glycol, or alkyl ester or alkyl ether thereof; and
(F) a chain hydrocarbon.

21. The absorbent article according to claim 16, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycol and at least one fatty acid, ($e_3$) an ether of a polyoxy $C_3$-$C_6$ alkylene glycol and at least one aliphatic monohydric alcohol, and ($f_1$) a chain alkane, as well as any combination thereof.

* * * * *

UNITED STATES PATENT AND TRADEMARK OFFICE
CERTIFICATE OF CORRECTION

PATENT NO. : 9,492,333 B2  
APPLICATION NO. : 14/430447  
DATED : November 15, 2016  
INVENTOR(S) : Masashi Uda et al.

Page 1 of 1

It is certified that error appears in the above-identified patent and that said Letters Patent is hereby corrected as shown below:

(72) Inventors:
Change "Takashi Maruyama, Kononji (JP)" to --Takashi Maruyama, Kanonji (JP)--.

Signed and Sealed this  
Ninth Day of May, 2017

Michelle K. Lee  
*Director of the United States Patent and Trademark Office*